US012734143B2

(12) United States Patent
Peterson et al.

(10) Patent No.: US 12,734,143 B2
(45) **Date of Patent: *Sep. 15, 2026**

(54) TREATMENT FOR INTERSTITIAL LUNG DISEASE

(71) Applicant: United Therapeutics Corporation, Silver Spring, MD (US)

(72) Inventors: Leigh Peterson, Hillsborough, NC (US); Peter Smith, Durham, NC (US); Chunqin Deng, Chapel Hill, NC (US)

(73) Assignee: United Therapeutics Corporation, Silver Spring, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/400,227

(22) Filed: Nov. 25, 2025

(65) Prior Publication Data

US 2026/0076929 A1 Mar. 19, 2026

Related U.S. Application Data

(63) Continuation of application No. 18/586,056, filed on Feb. 23, 2024, which is a continuation of application No. 18/219,944, filed on Jul. 10, 2023, now abandoned, which is a continuation of application No. 17/233,061, filed on Apr. 16, 2021, now Pat. No. 11,826,327.

(60) Provisional application No. 63/160,611, filed on Mar. 12, 2021, provisional application No. 63/011,810, filed on Apr. 17, 2020.

(51) Int. Cl.

| | |
|---|---|
| ***A61K 31/192*** | (2006.01) |
| ***A61K 9/00*** | (2006.01) |
| ***A61P 9/12*** | (2006.01) |

(52) U.S. Cl.
CPC .......... *A61K 31/192* (2013.01); *A61K 9/0075* (2013.01); *A61K 9/0078* (2013.01); *A61P 9/12* (2018.01)

(58) Field of Classification Search
CPC .................................................. A61K 31/192
See application file for complete search history.

(56) References Cited

U.S. PATENT DOCUMENTS

| | | | |
|---|---|---|---|
| 3,664,337 | A | 5/1972 | Lindsey et al. |
| 4,001,650 | A | 1/1977 | Romain |
| 4,007,238 | A | 2/1977 | Glenn |
| 4,281,113 | A | 7/1981 | Axen et al. |
| 4,306,075 | A | 12/1981 | Aristoff |
| 4,306,076 | A | 12/1981 | Nelson |
| 4,349,689 | A | 9/1982 | Aristoff |
| 4,473,296 | A | 9/1984 | Shofner et al. |
| 4,486,598 | A | 12/1984 | Aristoff |
| 4,495,944 | A | 1/1985 | Brisson et al. |
| 4,635,647 | A | 1/1987 | Choksi |
| 4,668,814 | A | 5/1987 | Aristoff |
| 4,677,975 | A | 7/1987 | Edgar et al. |
| 4,683,330 | A | 7/1987 | Aristoff |
| 4,692,464 | A | 9/1987 | Skuballa et al. |
| 4,708,963 | A | 11/1987 | Skuballa et al. |
| 4,976,259 | A | 12/1990 | Higson et al. |
| 4,984,158 | A | 1/1991 | Hillsman |
| 5,063,922 | A | 11/1991 | Hakkinen |
| 5,080,093 | A | 1/1992 | Raabe et al. |
| 5,153,222 | A | 10/1992 | Tadepalli et al. |
| 5,234,953 | A | 8/1993 | Crow et al. |
| 5,322,057 | A | 6/1994 | Raabe et al. |
| 5,361,989 | A | 11/1994 | Merchat et al. |
| 5,363,842 | A | 11/1994 | Mishelevich et al. |
| 5,497,763 | A | 3/1996 | Lloyd et al. |
| 5,551,416 | A | 9/1996 | Stimpson et al. |
| 5,727,542 | A | 3/1998 | King |
| 5,865,171 | A | 2/1999 | Cinquin |
| 5,881,715 | A | 3/1999 | Shibasaki |
| 5,908,158 | A | 6/1999 | Cheiman |
| 6,054,486 | A | 4/2000 | Crow et al. |
| 6,123,068 | A | 9/2000 | Lloyd et al. |
| 6,242,482 | B1 | 6/2001 | Shorr et al. |
| 6,357,671 | B1 | 3/2002 | Cewers |
| 6,441,245 | B1 | 8/2002 | Moriarty et al. |
| 6,521,212 | B1 | 2/2003 | Cloutier et al. |
| 6,528,688 | B2 | 3/2003 | Moriarty et al. |
| 6,626,843 | B2 | 9/2003 | Hillsman |
| 6,700,025 | B2 | 3/2004 | Moriarty et al. |
| 6,756,033 | B2 | 6/2004 | Cloutier et al. |
| 6,756,117 | B1 | 6/2004 | Barnes |
| 6,765,117 | B2 | 7/2004 | Moriarty et al. |
| 6,803,386 | B2 | 10/2004 | Shorr et al. |
| 6,809,223 | B2 | 10/2004 | Moriarty et al. |
| 7,172,557 | B1 | 2/2007 | Parker et al. |
| 7,199,157 | B2 | 4/2007 | Wade et al. |
| 7,261,102 | B2 | 8/2007 | Barney et al. |
| 7,384,978 | B2 | 6/2008 | Phares et al. |
| 7,417,070 | B2 | 8/2008 | Phares et al. |
| 7,544,713 | B2 | 6/2009 | Phares et al. |
| 7,726,303 | B2 | 6/2010 | Tyvoll et al. |
| 7,879,909 | B2 | 2/2011 | Wade et al. |
| 7,999,007 | B2 | 8/2011 | Jeffs et al. |
| 8,232,316 | B2 | 7/2012 | Phares et al. |
| 8,242,305 | B2 | 8/2012 | Batra et al. |
| 8,252,839 | B2 | 8/2012 | Phares et al. |

(Continued)

FOREIGN PATENT DOCUMENTS

| | | |
|---|---|---|
| AU | 1999959533 B2 | 2/2000 |
| CN | 109260182 A | 1/2019 |

(Continued)

OTHER PUBLICATIONS

Transcript of Bench Trial, vol. I, Jun. 23, 2025, *United Therapeutics Corporation*, Plaintiff, v. *Liquidia Technologies, Inc.*, Defendant, C.A. No. 23-CV-00975-RGA, 109 pages.

(Continued)

*Primary Examiner* — Paul V Ward
(74) *Attorney, Agent, or Firm* — Foley & Lardner LLP

(57) ABSTRACT

Methods of treating of interstitial lung disease, reducing pulmonary function decline in a subject with interstitial lung disease (ILD), and increasing forced vital capacity (FVC) in a subject suffering from ILD are provided, wherein the methods include administration of treprostinil.

24 Claims, 15 Drawing Sheets

(56) References Cited

U.S. PATENT DOCUMENTS

| | | | |
|---|---|---|---|
| 8,349,892 | B2 | 1/2013 | Phares |
| 8,350,079 | B2 | 1/2013 | Walsh |
| 8,410,169 | B2 | 4/2013 | Phares et al. |
| 8,461,393 | B2 | 6/2013 | Sharma |
| 8,481,782 | B2 | 7/2013 | Batra et al. |
| 8,497,393 | B2 | 7/2013 | Batra et al. |
| 8,536,363 | B2 | 9/2013 | Phares et al. |
| 8,563,614 | B2 | 10/2013 | Wade et al. |
| 8,609,728 | B2 | 12/2013 | Rothblatt et al. |
| 8,653,137 | B2 | 2/2014 | Jeffs et al. |
| 8,658,694 | B2 | 2/2014 | Jeffs et al. |
| 8,747,897 | B2 | 6/2014 | Kidane et al. |
| 8,765,813 | B2 | 7/2014 | Wade et al. |
| 8,940,930 | B2 | 1/2015 | Batra et al. |
| 9,029,607 | B2 | 5/2015 | Mcgowan et al. |
| 9,050,311 | B2 | 6/2015 | Phares et al. |
| 9,155,846 | B2 | 10/2015 | Kern |
| 9,156,786 | B2 | 10/2015 | Batra et al. |
| 9,199,908 | B2 | 12/2015 | Phares et al. |
| 9,255,064 | B2 | 2/2016 | Malinin et al. |
| 9,278,901 | B2 | 3/2016 | Phares et al. |
| 9,278,902 | B2 | 3/2016 | Tang et al. |
| 9,278,903 | B2 | 3/2016 | Tang et al. |
| 9,339,507 | B2 | 5/2016 | Olschewski et al. |
| 9,346,738 | B2 | 5/2016 | Jain et al. |
| 9,358,240 | B2 | 6/2016 | Olschewski et al. |
| 9,371,264 | B2 | 6/2016 | Becker et al. |
| 9,388,154 | B2 | 7/2016 | Yiannikouros et al. |
| 9,394,227 | B1 | 7/2016 | Zhang et al. |
| 9,422,223 | B2 | 8/2016 | Phares et al. |
| 9,469,600 | B2 | 10/2016 | Malinin et al. |
| 9,505,737 | B2 | 11/2016 | Becker et al. |
| 9,624,156 | B2 | 4/2017 | Phares et al. |
| 9,643,911 | B2 | 5/2017 | Zhang et al. |
| 9,701,616 | B2 | 7/2017 | Zhang et al. |
| 9,713,599 | B2 | 7/2017 | Wade |
| 9,758,465 | B2 | 9/2017 | Laing |
| 9,776,982 | B2 | 10/2017 | Becker et al. |
| 9,845,305 | B2 | 12/2017 | Becker et al. |
| 9,878,972 | B2 | 1/2018 | Phares et al. |
| 9,957,200 | B2 | 5/2018 | Beall et al. |
| 10,010,518 | B2 | 7/2018 | Malinin et al. |
| 10,053,414 | B2 | 8/2018 | Zhang et al. |
| 10,076,505 | B2 | 9/2018 | Wade |
| 10,246,403 | B2 | 4/2019 | Zhang et al. |
| 10,343,979 | B2 | 7/2019 | Malinin et al. |
| 10,344,012 | B2 | 7/2019 | Becker et al. |
| 10,376,525 | B2 | 8/2019 | Olschewski et al. |
| 10,450,290 | B2 | 10/2019 | Becker et al. |
| 10,464,877 | B2 | 11/2019 | Zhang et al. |
| 10,464,878 | B2 | 11/2019 | Zhang et al. |
| 10,494,327 | B2 | 12/2019 | Laing |
| 10,526,274 | B2 | 1/2020 | Malinin et al. |
| 10,695,308 | B2 | 6/2020 | Wade |
| 10,703,706 | B2 | 7/2020 | Zhang et al. |
| 10,716,793 | B2 | 7/2020 | Olschewski et al. |
| 10,752,733 | B2 | 8/2020 | Ishihara |
| 11,357,782 | B2 | 6/2022 | Olschewski et al. |
| 11,826,327 | B2 * | 11/2023 | Peterson .................. A61P 9/12 |
| 2003/0192532 | A1 | 10/2003 | Hopkins |
| 2004/0063912 | A1 | 4/2004 | Blumberg et al. |
| 2004/0105819 | A1 | 6/2004 | Hale et al. |
| 2004/0149282 | A1 | 8/2004 | Hickle |
| 2004/0265238 | A1 | 12/2004 | Chaudry |
| 2005/0080140 | A1 | 4/2005 | Hatae et al. |
| 2005/0165111 | A1 | 7/2005 | Wade et al. |
| 2005/0166913 | A1 | 8/2005 | Sexton et al. |
| 2005/0183719 | A1 | 8/2005 | Wuttke et al. |
| 2005/0282901 | A1 | 12/2005 | Phares et al. |
| 2006/0104913 | A1 | 5/2006 | Chaudry |
| 2006/0147520 | A1 | 7/2006 | Ruegg |
| 2006/0201500 | A1 | 9/2006 | Von Hollen et al. |
| 2008/0200449 | A1 | 8/2008 | Olschewski et al. |
| 2008/0280986 | A1 | 11/2008 | Wade et al. |
| 2009/0005394 | A1 | 1/2009 | Harbeson |
| 2009/0036465 | A1 | 2/2009 | Roscigno et al. |
| 2009/0124697 | A1 | 5/2009 | Cloutier et al. |
| 2009/0281189 | A1 | 11/2009 | Walsh |
| 2010/0076083 | A1 | 3/2010 | Olschewski et al. |
| 2010/0236545 | A1 | 9/2010 | Kern |
| 2010/0282622 | A1 | 11/2010 | Phares |
| 2012/0129941 | A1 | 5/2012 | Wade et al. |
| 2012/0177693 | A1 | 7/2012 | Cipolla et al. |
| 2012/0197041 | A1 | 8/2012 | Batra et al. |
| 2012/0216801 | A1 | 8/2012 | Olschewski et al. |
| 2013/0096200 | A1 | 4/2013 | Wade et al. |
| 2013/0184295 | A1 | 7/2013 | Sprague et al. |
| 2013/0331593 | A1 | 12/2013 | McGowan et al. |
| 2014/0018431 | A1 | 1/2014 | Wade et al. |
| 2014/0024856 | A1 | 1/2014 | Giust et al. |
| 2014/0271923 | A1 | 9/2014 | Reid |
| 2014/0275262 | A1 | 9/2014 | Phares et al. |
| 2014/0275616 | A1 | 9/2014 | Batra et al. |
| 2014/0323567 | A1 | 10/2014 | Laing |
| 2015/0126589 | A1 | 5/2015 | Geiger et al. |
| 2015/0148414 | A1 | 5/2015 | Malinin et al. |
| 2015/0299091 | A1 | 10/2015 | Batra et al. |
| 2015/0315114 | A1 | 11/2015 | Hering et al. |
| 2015/0328232 | A1 | 11/2015 | Malinin et al. |
| 2015/0376106 | A1 | 12/2015 | Batra et al. |
| 2016/0030355 | A1 | 2/2016 | Kidane et al. |
| 2016/0030371 | A1 | 2/2016 | Phares et al. |
| 2016/0045470 | A1 | 2/2016 | Reddy et al. |
| 2016/0051505 | A1 | 2/2016 | Phares et al. |
| 2016/0107973 | A1 | 4/2016 | Batra et al. |
| 2016/0129087 | A1 | 5/2016 | Christe et al. |
| 2016/0143868 | A1 | 5/2016 | Olschewski et al. |
| 2016/0152548 | A1 | 6/2016 | Gao et al. |
| 2016/0175319 | A1 | 6/2016 | Freissmuth et al. |
| 2017/0095432 | A1 | 4/2017 | Phares et al. |
| 2018/0153847 | A1 | 6/2018 | Phares et al. |
| 2018/0221447 | A1 | 8/2018 | Kumar et al. |
| 2019/0290597 | A1 | 9/2019 | Zhang et al. |
| 2019/0321290 | A1 | 10/2019 | Guarneri et al. |
| 2019/0336461 | A1 | 11/2019 | Kan et al. |
| 2019/0365778 | A1 | 12/2019 | Olschewski et al. |
| 2020/0085741 | A1 | 3/2020 | Kan et al. |
| 2020/0093830 | A1 | 3/2020 | Weers et al. |
| 2020/0171044 | A1 | 6/2020 | Olschewski et al. |
| 2020/0188322 | A1 | 6/2020 | Zhang et al. |
| 2021/0054009 | A1 | 2/2021 | Phares et al. |
| 2021/0177787 | A1 | 6/2021 | Wade |
| 2021/0205253 | A1 | 7/2021 | Song et al. |
| 2022/0008436 | A1 | 1/2022 | Olschewski et al. |
| 2022/0218720 | A1 | 7/2022 | Olschewski et al. |
| 2022/0323459 | A1 | 10/2022 | Olschewski et al. |
| 2023/0062605 | A1 | 3/2023 | Olschewski et al. |

FOREIGN PATENT DOCUMENTS

| | | | |
|---|---|---|---|
| CN | 109734580 | A | 5/2019 |
| CN | 110585205 | A | 12/2019 |
| DE | 19838711 | C1 | 6/2000 |
| DE | 19934582 | A1 | 1/2001 |
| DE | 19934582 | C2 | 9/2003 |
| FR | 2783431 | A1 | 3/2000 |
| JP | 2003-522003 | A | 7/2003 |
| JP | 2004-512101 | A | 4/2004 |
| JP | 2005-034341 | A | 2/2005 |
| WO | WO-93/00951 | A1 | 1/1993 |
| WO | WO-00/57701 | A1 | 10/2000 |
| WO | WO-01/58514 | A1 | 8/2001 |
| WO | WO-01/85241 | A1 | 11/2001 |
| WO | WO-02/34318 | A2 | 5/2002 |
| WO | WO-2005/007081 | A3 | 1/2005 |
| WO | WO-2007/134292 | A2 | 11/2007 |
| WO | WO-2008/098196 | A1 | 8/2008 |
| WO | WO-2012/009097 | A1 | 1/2012 |
| WO | WO-2014/085813 | A1 | 6/2014 |
| WO | WO-2015/138423 | A1 | 9/2015 |
| WO | WO-2016/038532 | A1 | 3/2016 |
| WO | WO-2016/055819 | A1 | 4/2016 |
| WO | WO-2016/081658 | A1 | 5/2016 |
| WO | WO-2016/105538 | A1 | 6/2016 |

(56) References Cited

FOREIGN PATENT DOCUMENTS

WO WO-2016/176399 A1 11/2016
WO WO-2016/205202 A1 12/2016
WO WO-2017/161387 A1 9/2017
WO WO-2017/192993 A1 11/2017
WO WO-2018/058124 A1 3/2018
WO WO-2019/157337 A1 8/2019
WO WO-2019/237028 A1 12/2019

OTHER PUBLICATIONS

Transcript of Bench Trial, vol. II, Jun. 24, 2025, *United Therapeutics Corporation*, Plaintiff, v. *Liquidia Technologies, Inc*., Defendant, C.A. No. 23-CV-00975-RGA, 115 pages.
Transcript of Bench Trial, vol. III, Jun. 25, 2025, *United Therapeutics Corporation*, Plaintiff, v. *Liquidia Technologies, Inc*., Defendant, C.A. No. 23-CV-00975-RGA, 133 pages.
Transcript of Bench Trial, vol. IV, Jun. 26, 2025, *United Therapeutics Corporation*, Plaintiff, v. *Liquidia Technologies, Inc*., Defendant, C.A. No. 23-CV-00975-RGA, 54 pages.
*United Therapeutics Corporation* (Plaintiff) v. *Liquidia Technologies, Inc*. (Defendant), Defendant's Answer to Complaint and Counterclaims, United States District Court for the Middle District of North Carolina, Civil Action No. 1:25-cv-00368-TDS-JLW, Jan. 23, 2026, 26 pages.
*United Therapeutics Corporation* (Plaintiff) v. *Liquidia Technologies, Inc*. (Defendant), Memorandum Opinion and Order, United States District Court for the Middle District of North Carolina, Civil Action No. 1:25-cv-00368, Dec. 23, 2025, 21 pages.
Copeland et al., Management of Progressive Fibrosing Interstitial Lung Diseases (PF-ILD), Frontiers in Medicine, Oct. 13, 2021, 8(743977):1-5.
Lawrence et al., "Converging Pathways: A Review of Pulmonary Hypertension in Interstitial Lung Disease," Life, Sep. 23, 2024, 14:1203, 1-17.
U.S. Appl. No. 17/486,721, filed Sep. 27, 2021.
U.S. Appl. No. 63/036,561, filed Jun. 9, 2020.
U.S. Appl. No. 63/125,145, filed Dec. 14, 2020, Phares et al.
'793 IPR Patent Owner Response, IPR2021-00406, Nov. 10, 2021, 75 pages.
Abe et al., "Effects of inhaled prostacyclin analogue on chronic hypoxic pulmonary hypertension," J. Cardiovascular Pharmacology, 2001, 37, 239 251.
AccuNeb label, Jun. 2005, 2 pages.
Agarwal et al., "Inhaled Treprostinil in Group-3 Pulmonary Hypertension," J. Heart Lung Transplant., 2015 34(Suppl S343):959, abstract.
Agnew JE, Bateman RM, Pavia D, Clarke SW. (1984) Radionuclide demonstration of ventilatory abnormalities in mild asthma. Clinical Science; 66: 525-531.
Anderson, Paula J. M.D., "History of Aerosol Therapy: Liquid Nebulization to MDIs to DPIs," Respiratory Care, Sep. 2005, 50(9):1139-1150.
Annals of the International Commission on Radiological Protection (ICRP) vol. 28, No. 3, 1998, Publication 80, Radiation Dose to Patients from Radiopharmaceuticals.
Aradigm Corporation Form 10-Q for the quarterly period ended Jun. 30, 2009, 37 pages.
Aradigm Corporation news release Oct. 24, 2005, "Aradigm and United Therapeutics Sign Development and Commercialization Agreement Targeting Pulmonary Hypertension," Red Orbit News, http://www.redorbit.com/modules/news/tools.php?tool=print&id=281787, 2 pages.
Aristoff et al., "Synthesis of benzopyran prostaglandins, potent stable prostacyclin analogs, via an intermolecular mitsunobu reaction," Tetrahedron Letters, 1984, 25(36): 3955-3958.
Atkins, Paul J., Ph.D., "Dry Powder Inhalers: An Overview," Respiratory Care, Oct. 2005, 50(10):1304-1312.
ATS 2020 Virtual Preview: Clinical Trials Session, Jun. 24, 2020, conference.thoracic.org/program/session-information/virtual-clinical-trials.php.
AZMACORT label, May 2003, 16 pages.
Badesch et al., "Prostanoid Therapy for Pulmonary Arterial Hypertension," Journal of the American College of Cardiology, 2004, 43(12:SupplS):56S-61S.
Bajwa et al., "The safety and tolerability of inhaled treprostinil in patients with pulmonary hypertension and chronic obstructive pulmonary disease," Pulmonary Circulation, 2017, 7(1):82-88.
Beasley et al., "Preservatives in Nebulizer Solutions: Risks without Benefit," Pharmacotherapy, 1998, 18(1):130-139.
Bein et al., "Cardiovascular and pulmonary effects of aerosolized prostacyclin administration in severe respiratory failure using a ventilator nebulization system," J. Cardiovascular Pharmacology, 1996, 27, 583-586.
Bender et al,. "Nonadherence in asthmatic patients: is there a solution to the problem?", Ann. Allergy Asthma Immunol., 1997, 79:177-186.
Benedict et al., "Evidence-based pharmacologic management of pulmonary arterial hypertension," Clinical Therapeutics, 2007, 29, 2134-2153.
Bindl et al., "Aerosolised prostacyclin for pulmonary hypertension in neonates," Archives of disease in childhood, Fetal and neonatal edition, 1994, 71(3), F214-6.
Blanchard, J.D., Cipolla, D., Liu, K., Morishige, R., Mudumba, S., Thipphawong, J., Taylor, G., Warren, S., Radhakrishnan, R., Van Vlasselaer, R., Visor , G. and Starko, K. (2003) Lung Deposition of Interferon Gamma-1b following Inhalation via AERx® System vs. Respirgard II™ Nebulizer Proc. ATS Annual Meeting (Abstract A373), Seattle.
Bonner et al., "Susceptibility of Cyclooxygenase-2-Deficient Mice to Pulmonary Fibrogenesis," American Journal of Pathology, Aug. 2002, 161(2):459-470.
Booke et al., "Prostaglandins in Patients with Pulmonary Hypertension: The Route of Administration," Anesth. Analg., 1998, 86:917, Letter to the Editor.
Boyd, B., Noymer, P., Liu, K., Okikawa, J., Hasegawa, D., Warren, S., Taylor, G., Ferguson, E., Schuster, J., Farr, S., and Gonda, I. (2004) Effect of Gender and Device Mouthpiece Shape on Bolus Insulin Aerosol Delivery Using the AERx Pulmonary Delivery System. Pharmaceutical Research. 21 (10) 1776-1782.
Boyle et al., "So Many Drugs, So Little Time: The Future Challenge of Cystic Fibrosis Care," Chest, Jan. 2003, 123(1):3-5.
Burger et al., "Inhaled treprostinil vs iloprost: Comparison of adherence, persistence, and health care resource utilization in patients with pulmonary arterial hypertension," J. Manag. Care Spec. Pharm., 2023, 29(1):101-108.
Byron, Peter R. "Drug Delivery Devices, Issues in Drug Development," Proc. Am. Thorac. Soc., 2004, 1:321-328.
Channick et al., "Safety and efficacy of inhaled treprostinil as add-on therapy to bosentan in pulmonary arterial hypertension," J. American College of Cardiology, 2006, 48, 1433-1437.
Chattaraj, Sarat C., "Treprostinil sodium Pharmacia," Current Opinion in Investigational Drugs, Apr. 2002, 3(4):582-586.
Chew et al., "Pharmaceutical Dry Powder Aerosol Delivery," KONA, 2001, 19:46-56.
Claim Construction Order, Oct. 21, 2024, in *United Therapeutics Corporation* (Plaintiff) v. *Liquidia Technologies, Inc*. (Defendant), C.A. No. 23-975-RGA, 2 pages.
Clark, A.R., "Medical Aerosol Inhalers: Past, Present, and Future," Aerosol Science and Technology, Jun. 12, 2007, 22(4):374-391.
Collard et al., "Acute Exacerbation of Idiopathic Pulmonary Fibrosis: An International Working Group Report," Am. J. Respir. Crit. Care Med., Aug. 1, 2016, 194(3):265-275.
Colthorpe P, Taylor G, Farr SJ. (1997) A comparison of two non-invasive methods for quantifying aerosol deposition in the lungs of rabbits. J. Aerosol Med.; 10:255.
Dalby et al., "A review of the development of Respimat Soft Mist Inhaler," International Journal of Pharmaceutics, 2004, 283:1-9.
De Wet et al., "Inhaled prostacyclin is safe, effective and affordable in patients with pulmonary hypertension, right heart dysfunction,

(56) References Cited

OTHER PUBLICATIONS and refractory hypoxemia after cardiothoracic surgery," J. Thoracic Cardiovasc. Surg., 2004, 127:1058-1067.
Decision Granting Institution of Inter Partes Review, IPR2021-00406, U.S. Pat. No. 10,716,793, *Liquidia Technologies, Inc.* (Petitioner) v. *United Therapeutics Corp.* (Patent Owner), Aug. 11, 2021, 44 pages.
Decision in CAFC 2023-1805, Dec. 20, 2023, *United Therapeutics Corporation* (Appellant) v. *Liquidia Technologies, Inc.* (Appellee), 13 pages.
Declaration of Douglas Kidder with Exhibits 1 and 2, *United Therapeutics Corporation* (Plaintiff) v. *Liquidia Technologies, Inc.* (Defendant), C.A. No. 23-975 (RGA)(SRF), filed Apr. 18, 2024, 73 pages.
Declaration of Dr. Aaron Waxman, Exhibit 2001, May 17, 2021, 21 pages, *Liquidia Technologies, Inc.* (Petitioner) v. *United Therapeutics Corporation* (Patent Owner), IPR2021-00406.
Declaration of Dr. Aaron Waxman, M.D., Ph.D, Exhibit 2052, Nov. 10, 2021, 56 pages, *Liquidia Technologies, Inc.* (Petitioner) v. *United Therapeutics Corporation* (Patent Owner), IPR2021-00406.
Declaration of Dr. Richard Channick with Appendix A and B, *United Therapeutics Corporation* (Plaintiff) v. *Liquidia Technologies, Inc.* (Defendant), C.A. No. 23-975 (RGA)(SRF), filed Apr. 19, 2024, 111 pages.
Declaration of Dr. Werner Seeger, Exhibit 2003, May 10, 2021, 16 pages, *Liquidia Technologies, Inc.* (Petitioner) v. *United Therapeutics Corporation* (Patent Owner), IPR2021-00406.
Declaration of Frederic Selck, Ph.D. in Support of Plaintiff's Motion for Preliminary Injunction with Attachments A-1-C-1, *United Therapeutics Corporation* (Plaintiff) v. *Liquidia Technologies, Inc.* (Defendant), C.A. No. 23-975 (RGA)(SRF), filed Mar. 4, 2024, 124 pages.
Declaration of Michael J. Flynn in Support of Plaintiff's Motion for Preliminary Injunction with Exhibits 1-7, *United Therapeutics Corporation* (Plaintiff) v. *Liquidia Technologies, Inc.* (Defendant), C.A. No. 23-975 (RGA), filed Mar. 4, 2024, 99 pages.
Declaration of Michael J. Flynn in Support of Plaintiff's Reply Brief in Support of its Motion for Preliminary Injunction with Exhibits 8-20, *United Therapeutics Corporation* (Plaintiff) v. *Liquidia Technologies, Inc.* (Defendant), C.A. No. 23-975 (RGA)(SRF), filed Apr. 22, 2024, 519 pages.
Declaration of Steven Nathan, M.D. in Support of Plaintiff's Motion for Preliminary Injunction with Attachments A-C, *United Therapeutics Corporation* (Plaintiff) v. *Liquidia Technologies, Inc.* (Defendant), C.A. No. 23-975 (RGA), filed Mar. 4, 2024, 150 pages.
Defendant Liquidia Technologies, Inc.'s Answering Brief in Opposition to Plaintiff's Motion for Preliminary Injunction, *United Therapeutics Corporation* (Plaintiff) v. *Liquidia Technologies, Inc.* (Defendant), C.A. No. 23-975 (RGA), Apr. 18, 2024, 32 pages.
Defendant Liquidia Technologies, Inc.'s Appendix of Exhibits in Support of its Answering Brief in Opposition to Plaintiff's Motion for Preliminary Injunction with Exhibits 1-39, *United Therapeutics Corporation* (Plaintiff) v. *Liquidia Technologies, Inc.* (Defendant), C.A. No. 23-975 (RGA)(SRF), filed Apr. 29, 2024, 1047 pages.
Defendant Liquidia Technologies, Inc.'s Appendix of Exhibits in Support of its Answering Brief in Opposition to Plaintiff's Motion for Preliminary Injunction, with exhibits 1-39, *United Therapeutics Corporation* (Plaintiff) v. *Liquidia Technologies, Inc.* (Defendant), C.A. No. 23-975 (RGA)(SRF), filed Apr. 19, 2024, 1048 pages.
Defendant Liquidia Technologies, Inc.'s First Amended Invalidity Contentions, *United Therapeutics Corporation*, Plaintiff, v. *Liquidia Technologies, Inc.*, Defendant, C.A. No. 1-23-cv-00975-RGA, Jul. 16, 2024, 194 pages.
Defendant Liquidia Technologies, Inc.'s Motion for Leave to Submit a 1-Page Brief Responding to the Court's Questions at the Preliminary Injunction Hearing, *United Therapeutics Corporation* (Plaintiff) v. *Liquidia Technologies, Inc.* (Defendant), C.A. No. 23-975 (RGA)(SRF), filed Apr. 26, 2024, 6 pages.
Defendant Liquidia Technologies, Inc.'s Response Regarding bond Figures, *United Therapeutics Corporation* (Plaintiff) v. *Liquidia Technologies, Inc.* (Defendant), C.A. No. 23-975 (RGA)(SRF), filed May 3, 2024, 11 pages.
Defendant Watson Laboratories, Inc.'s Invalidity Contentions for U.S. Pat. Nos. 9,339,507 and 9,358,240, in The United States District Court for the District of New Jersey, Civil Action No. 3.15:cv- 05723-PGS-LHG, Aug. 5, 2016, 56 pages.
Defendant's Answer to First Amended Complaint and Counterclaims, Jan. 8, 2024, in *United Therapeutics Corporation* (Plaintiff) v. *Liquidia Technologies, Inc.* (Defendant), C.A. No. 23-975-RGA, 46 pages.
Denyer et al., "The Adaptive Aerosol Delivery (AAD) Technology: Past, Present, and Future," Journal of Aerosol Medicine and Pulmonary Drug Delivery, 2010, 23(Suppl):S1-S10.
Dernaika et al., "Iloprost Improves Gas Exchange and Exercise Tolerance in Patients with Pulmonary Hypertension and Chronic Obstructive Pulmonary Disease," Respiration, 2010, 79:377-382.
District court '793 infringement Trial Opinion, *United Therapeutics Corporation* (Plaintiff) v. *Liquidia Technologies, Inc.* (Defendant), Civil Action No. 20-755-RGA, Aug. 31, 2022, 55 pages.
Dolovich et al., "Device Selection and Outcomes of Aerosol Therapy: Evidence-Based Guidelines," Chest, Jan. 2005, 127(1):335-371.
Doyle et al., "Inhaled prostacyclin as a selective pulmonary vasodilator," Anaesthesia and Intensive Care, Aug. 1996, 24(4):514-515.
Dr. Hill's trial court testimony, Mar. 29, 2022, 5 pages, in *United Therapeutics Corporation* (Plaintiff) v. *Liquidia Technologies, Inc.* (Defendant), C.A. No. 20-755-RGA-JLM vol. II.
Du Bois et al., "Six-Minute-Walk Test in Idiopathic Pulmonary Fibrosis," Am. J. Respir. Crit. Care Med., 2011, 183:1231-1237.
Dumas et al.,. "Hypoxic pulmonary vasoconstriction," General Pharmacology, 1999, 33, 289-297.
Dworetz et al., "Survival of infants with persistent pulmonary hypertension without extracorporeal membrane oxygenation," Pediatrics, 1989, 84, 1-6.
Eli Lilly Press Release, "Eli Lilly and Company Licenses U.S. Rights for Tadalafil PAH Indication to United Therapeutics Corporation," Nov. 17, 2008, 4 pages.
English translation of OptiNeb User Manual, 2005, 33 pages.
EPA Integrated Risk Information System (IRIS): data sheet for 3-methylphenol (m-cresol). Accessed at http://www.epa.gov/iris/subst/0301/htm on Mar. 9, 2014.
Espacenet European Patent Office machine translation of Buff et al. DE19934582 (A1), Translation provided on Mar. 8, 2013.
Espacenet European Patent Office machine translation of Gessler et al. DE19838711 (C1), Translation provided on Mar. 8, 2013.
EU Community Register, Annexes to Commission Decision C(2005)3436, Sep. 5, 2005, http://ec.europa.eu/health/documents/communityregister/2005/2005090510259/anx_10259_en.pdf (Annex III—Ventavis® Labelling and Package Leaflet), 30 pages.
Ewert et al., "Aerosolized iloprost for primary pulmonary hypertension," New England Journal of Medicine, 2000, 343, 1421-1422.
Ewert et al., "Iloprost als inhalative bzw. Intravenose langzeitbehandlung von patienten mit primarer pulmonaler hypertonie," Z. Kardiol., 2000, 89, 987-999, English summary on first page.
Exhibit 1002, IPR2021-00406.
Exhibit 1003, IPR2021-00406.
Exhibit 1004, IPR2021-00406.
Exhibit 1005, IPR2021-00406.
Exhibit 1036, IPR2021-00406.
Exhibit 2036, 7 pages, *Liquidia Technologies, Inc.* (Petitioner) v. *United Therapeutics Corporation* (Patent Owner), IPR2021-00406.
Exhibit 2084, 9 pages, *Liquidia Technologies, Inc.* (Petitioner) v. *United Therapeutics Corporation* (Patent Owner), IPR2021-00406.
Exhibit 2085, 9 pages, *Liquidia Technologies, Inc.* (Petitioner) v. *United Therapeutics Corporation* (Patent Owner), IPR2021-00406.
Exhibit 2088, 37 pages, *Liquidia Technologies, Inc.* (Petitioner) v. *United Therapeutics Corporation* (Patent Owner), IPR2021-00406.
Exhibit 2089, 260 pages, *Liquidia Technologies, Inc.* (Petitioner) v. *United Therapeutics Corporation* (Patent Owner), IPR2021-00406.

(56) References Cited

OTHER PUBLICATIONS

Exhibits 1-42 of Defendant's Answer to First Amended Complaint and Counterclaims, Jan. 8, 2024, in *United Therapeutics Corporation* (Plaintiff) v. *Liquidia Technologies, Inc*. (Defendant), C.A. No. 23-975-RGA, 997 pages.
Exhibits 1087-1110 and 1112-1131 to Petitioner's Reply, Feb. 10, 2022, 1,337 pages, *Liquidia Technologies, Inc*. (Petitioner) v. *United Therapeutics Corporation* (Patent Owner), IPR2021-00406.
Exhibits 2001-2035 to Patent Owner Preliminary Response, May 17, 2021, 614 pages, IPR2021-00406, U.S. Pat. No. 10,716,793, *Liquidia Technologies, Inc*.(Petitioner) v. *United Therapeutics Corp*. (Patent Owner).
Farber et al., "Pulmonary Arterial Hypertension," The New England Journal of Medicine, 2004, 351:1655-1665.
Faria-Urbina et al., "Inhaled Treprostinil in Pulmonary Hypertension Associated with Lung Disease," Lung, 2018, 196:139-146.
Farr et al., "Comparison of in vitro and in vivo efficiencies of a novel unit-dose liquid aerosol generator and a pressurized metered dose inhaler," International Journal of Pharmaceutics, 2000, 198:63-70.
Federal Circuit's Dec. 20, 2023 decision of invalidity for the '793 patent, *United Therapeutics Corporation* (Appellant)_ v. *Liquidia Technologies, Inc*. (Appellee). CAFC 2023-1805, 13 pages.
Federal Circuit's Mar. 12, 2024 decision denying rehearing re '793 patent, *United Therapeutics Corporation* (Appellant)_ v. *Liquidia Technologies, Inc*. (Appellee). CAFC 2023-1805, 2 pages.
Federal Circuit's Jul. 24, 2023 decision affirming infringement of the '793 patent.
Findlay et al., "Radioimmunoassay for the Chemical Stable Prostacyclin Analog, 15AU81: a Preliminary Pharmacokinetics Study in the Dog," Prostaglandins Leukot. Essent. Fatty Acids, Feb. 1993, 48(2):167-174.
Fink et al., "Use of Prostacyclin and its Analogues in the Treatment of Cardiovascular Disease," Heart Disease, 1999, 1:29-40.
Flolan label, Sep. 2002, 24 pages.
Frijlink et al., "Dry Powder inhalers for pulmonary drug delivery," Expert Opin. Drug Deliv., 2004, 1(1):67-86.
Geller et al., "Bolus Inhalation of rhDNase with the AERx System in Subjects with Cystic Fibrosis," Journal of Aerosol Medicine, 2003, 16(2):175-182.
Geller, David E., M.D., "Comparing Clinical Features of the Nebulizer, Metered-Dose Inhaler, and Dry Powder Inhaler," Respir. Care, 2005, 50(10):1313-1321.
Gessler et al., "Ultrasonic versus jet nebulization of iloprost in severe pulmonary hypertension," Eur. Respir. J., 2001, 17, 14-19.
Ghofrani et al., "New therapies in the treatment of pulmonary hypertension," HERZ (Heart), Jun. 2005, 30(4):296-302, with English translation.
Ghofrani et al., "Hypoxia- and non-hypoxia-related pulmonary hypertension—Established and new therapies," Cardiovascular Research, 2006, 72:30-40.
Goldsmith et al., "Inhaled Iloprost In Primary Pulmonary Hypertension," Drugs, 2004, 64(7):763-773.
Gonda, Igor, "A semi-empirical model of aerosol deposition in the human respiratory tract for mouth inhalation," J. Pharm. Pharmacol., 1981, 33:692-696.
Gonda, Igor, "Study of the effects of polydispersity of aerosols on regional deposition in the respiratory tract," J. Pharm. Pharmacol., 1981, 33(Supp):52P.
Hache et al., "Inhaled epoprostenol (prostacyclin) and pulmonary hypertension before cardiac surgery," The Journal of Thoracic and Cardiovascular Surgery, Mar. 2003, 125:642-649.
Hallioglu et al., "Comparison of Acute Hemodynamic Effects of Aerosolized and Intravenous Iloprost in Secondary Pulmonary Hypertension in Children With Congenital Heart Disease," Am. J. Cardiol., 2003, 92:1007-1009.
Haraldsson et al., "Comparison of inhaled nitric oxide and inhaled aerosolized prostacyclin in the evaluation of heart transplant candidates with elevated pulmonary vascular resistance," Chest, 1998, 114, 780-786.
Hill et al., "Inhaled Therapies for Pulmonary Hypertension," Respiratory Care, Jun. 2015, 60(6):794-805.
Hindle et al., The Drug Delivery Companies Report, Autumn/ Winter 2004, 31-34.
Hoeper et al., "Long-term Treatment of Primary Pulmonary Hypertension with Aerosolized Iloprost, a Prostacyclin Analogue," The New England Journal of Medicine, Jun. 22, 2000, 342:1866-1870.
Hoeper et al., "A comparison of the acute hemodynamic effects of inhaled nitric oxide and aerosolized iloprost in primary hypertension," J. American College of Cardiology, 2000, 35, 176-182.
Hoeper et al., "Effects of inhaled nitric oxide and aerosolized iloprost in pulmonary veno-occlusive disease," Respiratory Medicine, 1999, 93, 62-70.
Horn et al., "Treprostinil therapy for pulmonary artery hypertension," Expert Opinion on Investigational Drugs, 2002, 11(11):1615-1622.
Howarth, P.H., "Why particle size should affect clinical response to inhaled therapy," Journal of Aerosol Medicine, 2001, 14 Supp. 1, S-27-S-34.
Ichida et al., "Additive effects of beraprost on pulmonary vasodilation by inhaled nitric oxide in children with pulmonary hypertension," American Journal of Cardiology, 1997, 80, 662-664.
IPR2021-00406 Final Decision Jul. 2022, 49 pages.
Keerthisingham et al., "Cyclooxygenase-2 Deficiency Results in a Loss of the Anti-Proliferative Response to Transforming Growth Factor-Beta in Human Fibrotic Lung Fibroblasts and Promotes Bleomycin-Induced Pulmonary Fibrosis in Mice," American Journal of Pathology, Apr. 2001, 158(4):1411-1422.
King et al., "The Trouble With Group 3 Pulmonary Hypertension in Interstitial Lung Disease," Chest, 2020, 158(4):1651-1664.
Konorza et al., "Klinisch-pharmakologische Austestung bei pulmonaler Hypertonie zur Therapiefuehrung," Herz, 2005, 30:286-295, English abstract on first page.
Krause et al., "Pharmacokinetics and pharmacodynamics of the prostacyclin analogue iloprost in man," Eur. J. Clin. Pharmacol., 1986, 30, 61-68.
Labiris et al., "Pulmonary drug delivery. Part II: The role of inhalant delivery devices and drug formulations in therapeutic effectiveness of aerosolized medications," Br. J. Clin. Pharmacol., 2003, 56(6):600-612.
Laliberte et al., "Pharmacokinetics and Steady-State Bioequivalence of Treprostinil Sodium (Remodulin) Administered by the Intravenous and Subcutaneous Route to Normal Volunteers," J. Cardiovasc. Pharmacol, Aug. 2004, 44(2):209-214.
Lee et al., "Current strategies for pulmonary arterial hypertension," J. Internal Medicine, 2005, 258, 199-215.
Letter from Michael J. Flynn to Judge Andrews, *United Therapeutics Corporation* (Plaintiff) v. *Liquidia Technologies, Inc*. (Defendant), C.A. No. 23-975 (RGA)(SRF), filed May 3, 2024, 4 pages.
Lettieri et al., "The distance-saturation product predicts mortality in idiopathic pulmonary fibrosis," Respiratory Medicine, 2006, 100:1734-1741.
Liquidia Notice of Supplemental Authority with Exhibit 1, *United Therapeutics Corporation* (Plaintiff) v. *Liquidia Technologies, Inc*. (Defendant), C.A. No. 23-975 (RGA)(SRF), filed May 10, 2024, 5 pages.
Liquidia Notice of Supplemental Authority with Exhibit 1, *United Therapeutics Corporation* (Plaintiff) v. *Liquidia Technologies, Inc*. (Defendant), C.A. No. 23-975 (RGA)(SRF), filed May 13, 2024, 10 pages.
Liquidia Technologies Press Release, "Liquidia Announces FDA Acceptance of New Drug Application for LIQ861 (treprostinil) Inhalation Powder for the Treatment of Pulmonary Arterial Hypertension," Apr. 8, 2020, 3 pages.
Liquidia Technologies Press Release, "Liquidia Submits New Drug Application for LIQ861 (treprostinil) Inhalation Powder to U.S. Food and Drug Administration for the Treatment of Pulmonary Arterial Hypertension (PAH)," Jan. 27, 2020, 3 pages.
Martin, John C., "Inhaled Form of Remodulin in the Pipeline," http://www.phneighborhood.com/content/in_the_news/archive_2320, aspx, ph Neighborhood, Oct. 28, 2005, 2 pages.
Max et al., "Inhaled prostacyclin in the treatment of pulmonary hypertension," Eur. J. Pediatr., 1999, 158 Suppl 1, S23-S26.

(56) References Cited

OTHER PUBLICATIONS

McLaughlin et al., "Addition of Inhaled Treprostinil to Oral Therapy for Pulmonary Arterial Hypertension," Journal of the American College of Cardiology, 2010, 55(18):1915-1922.
McNulty et al., "The Pharmacokinetics and Pharmacodynamics of the Prostacyclin Analog 15AU81 in the Anesthetized Beagle Dog," Prostaglandins Leukot. Essent. Fatty Acids, Feb. 1993, 48(2):159-166.
Memorandum Opinion, Jun. 18, 2025, in *United Therapeutics Corporation* (Plaintiff) v. *Liquidia Technologies, Inc*. (Defendant), C.A. No. 23-975-RGA, 12 pages.
Memorandum Opinion, *United Therapeutics Corporation* (Plaintiff) v. *Liquidia Technologies, Inc*. (Defendant), C.A. No. 23-975-RGA, Oct. 16, 2024, 11 pages.
Memorandum Order denying Motion for Preliminary Injunction, *United Therapeutics Corporation* (Plaintiff) v. *Liquidia Technologies, Inc*. (Defendant), C.A. No. 23-975 (RGA)(SRF), filed May 31, 2024, 30 pages.
Meyer et al., "Role of pirfenidone in the management of pulmonary fibrosis," Therapeutics and Clinical Risk Management, 2017, 13:427-437.
Miller et al., "Standardisation of spirometry. Series ATS/ERS Task Force: Standardisation of Lung Function Testing" Eur Respir J 2005; 26: 319-338.
Mueller et al., "Inhaled iloprost in the management of pulmonary hypertension in infants undergoing congenital heart surgery," European Journal of Anesthesiology, Jun. 2004, 21(Suppl.33):3, Abstract No. 084.
Nathan et al., "Pulmonary Hypertension due to Lung Disease and/or Hypoxia," Clin. Chest Med., 2013, 34:695-705.
Nathan et al., "Pulmonary hypertension in interstitial lung disease," Int. J. Clin. Pract., Jul. 2008, 62(Suppl. 160):21-28.
Nathan et al., "Riociguat for idiopathic interstitial pneumonia-associated pulmonary hypertension (RISE-IIP): a randomised, placebo-controlled phase 2b study," Lancet Respir. Med., 2019, 7:780-790.
Nathan et al., "Validation of test performance characteristics and minimal clinically important difference of the 6-minute walk test in patients with idiopathic pulmonary fibrosis," Respiratory Medicine, 2015, 109:914-922.
National Radiological Protection Board. Doses to Patients from Medical Radiological Examinations in Great Britain. (1986) Radiological Protection Bulletin No. 77.
Nauser et al., "Pulmonary Hypertension: New Perspectives," CHF, 2003, 9:155-162.
NCT02630316, Safety and Efficacy of Inhaled Treprostinil in Adult PH with ILD Including CPFE, ClinicalTrials.gov, 10 pages, Dec. 19, 2016.
NCT02630316, Safety and Efficacy of Inhaled Treprostinil in Adult PH with ILD Including CPFE, ClinicalTrials.gov, 10 pages, Dec. 7, 2016.
NCT02630316, Safety and Efficacy of Inhaled Treprostinil in Adult PH with ILD Including CPFE, ClinicalTrials.gov, 11 pages, Feb. 1, 2017.
NCT02630316, Safety and Efficacy of Inhaled Treprostinil in Adult PH with ILD Including CPFE, ClinicalTrials.gov, 11 pages, Jan. 12, 2017.
NCT02630316, Safety and Efficacy of Inhaled Treprostinil in Adult PH with ILD Including CPFE, ClinicalTrials.gov, 11 pages, Mar. 1, 2017.
NCT02630316, Safety and Efficacy of Inhaled Treprostinil in Adult PH with ILD Including CPFE, ClinicalTrials.gov, 11 pages, Mar. 17, 2017.
NCT02630316, Safety and Efficacy of Inhaled Treprostinil in Adult PH with ILD Including CPFE, ClinicalTrials.gov, 11 pages, Mar. 9, 2017.
NCT02630316, Safety and Efficacy of Inhaled Treprostinil in Adult PH with ILD Including CPFE, ClinicalTrials.gov, 12 pages, Apr. 13, 2017.
NCT02630316, Safety and Efficacy of Inhaled Treprostinil in Adult PH with ILD Including CPFE, ClinicalTrials.gov, 12 pages, Feb. 9, 2017.
NCT02630316, Safety and Efficacy of Inhaled Treprostinil in Adult PH with ILD Including CPFE, ClinicalTrials.gov, 12 pages, Jul. 13, 2017.
NCT02630316, Safety and Efficacy of Inhaled Treprostinil in Adult PH with ILD Including CPFE, ClinicalTrials.gov, 12 pages, Jul. 19, 2017.
NCT02630316, Safety and Efficacy of Inhaled Treprostinil in Adult PH with ILD Including CPFE, ClinicalTrials.gov, 12 pages, Jul. 31, 2017.
NCT02630316, Safety and Efficacy of Inhaled Treprostinil in Adult PH with ILD Including CPFE, ClinicalTrials.gov, 12 pages, Jul. 5, 2017.
NCT02630316, Safety and Efficacy of Inhaled Treprostinil in Adult PH with ILD Including CPFE, ClinicalTrials.gov, 12 pages, Jun. 19, 2017.
NCT02630316, Safety and Efficacy of Inhaled Treprostinil in Adult PH with ILD Including CPFE, ClinicalTrials.gov, 12 pages, Jun. 2, 2017.
NCT02630316, Safety and Efficacy of Inhaled Treprostinil in Adult PH with ILD Including CPFE, ClinicalTrials.gov, 12 pages, Mar. 27, 2017.
NCT02630316, Safety and Efficacy of Inhaled Treprostinil in Adult PH with ILD Including CPFE, ClinicalTrials.gov, 12 pages, May 19, 2017.
NCT02630316, Safety and Efficacy of Inhaled Treprostinil in Adult PH with ILD Including CPFE, ClinicalTrials.gov, 13 pages, Aug. 16, 2017.
NCT02630316, Safety and Efficacy of Inhaled Treprostinil in Adult PH with ILD Including CPFE, ClinicalTrials.gov, 13 pages, Oct. 13, 2017.
NCT02630316, Safety and Efficacy of Inhaled Treprostinil in Adult PH with ILD Including CPFE, ClinicalTrials.gov, 13 pages, Sep. 1, 2017.
NCT02630316, Safety and Efficacy of Inhaled Treprostinil in Adult PH with ILD Including CPFE, ClinicalTrials.gov, 13 pages, Sep. 12, 2017.
NCT02630316, Safety and Efficacy of Inhaled Treprostinil in Adult PH with ILD Including CPFE, ClinicalTrials.gov, 13 pages, Sep. 14, 2017.
NCT02630316, Safety and Efficacy of Inhaled Treprostinil in Adult PH with ILD Including CPFE, ClinicalTrials.gov, 13 pages, Sep. 20, 2017.
NCT02630316, Safety and Efficacy of Inhaled Treprostinil in Adult PH with ILD Including CPFE, ClinicalTrials.gov, 13 pages, Sep. 8, 2017.
NCT02630316, Safety and Efficacy of Inhaled Treprostinil in Adult PH with ILD Including CPFE, ClinicalTrials.gov, 14 pages, Nov. 14, 2017.
NCT02630316, Safety and Efficacy of Inhaled Treprostinil in Adult PH with ILD Including CPFE, ClinicalTrials.gov, 14 pages, Oct. 25, 2017.
NCT02630316, Safety and Efficacy of Inhaled Treprostinil in Adult PH with ILD Including CPFE, ClinicalTrials.gov, 15 pages, Dec. 20, 2019.
NCT02630316, Safety and Efficacy of Inhaled Treprostinil in Adult PH with ILD Including CPFE, ClinicalTrials.gov, 15 pages, Mar. 6, 2018.
NCT02630316, Safety and Efficacy of Inhaled Treprostinil in Adult PH with ILD Including CPFE, ClinicalTrials.gov, 15 pages, Oct. 10, 2019.
NCT02630316, Safety and Efficacy of Inhaled Treprostinil in Adult PH with ILD Including CPFE, ClinicalTrials.gov, 15 pages, Oct. 23, 2019.
NCT02630316, Safety and Efficacy of Inhaled Treprostinil in Adult PH with ILD Including CPFE, ClinicalTrials.gov, 15 pages, Oct. 28, 2019.
NCT02630316, Safety and Efficacy of Inhaled Treprostinil in Adult PH with ILD Including CPFE, ClinicalTrials.gov, 15 pages, Oct. 8, 2019.

(56) References Cited

OTHER PUBLICATIONS

NCT02630316, Safety and Efficacy of Inhaled Treprostinil in Adult PH with ILD Including CPFE, ClinicalTrials.gov, 16 pages, Apr. 15, 2019.
NCT02630316, Safety and Efficacy of Inhaled Treprostinil in Adult PH with ILD Including CPFE, ClinicalTrials.gov, 16 pages, Apr. 19, 2019.
NCT02630316, Safety and Efficacy of Inhaled Treprostinil in Adult PH with ILD Including CPFE, ClinicalTrials.gov, 16 pages, Apr. 24, 2018.
NCT02630316, Safety and Efficacy of Inhaled Treprostinil in Adult PH with ILD Including CPFE, ClinicalTrials.gov, 16 pages, Aug. 13, 2018.
NCT02630316, Safety and Efficacy of Inhaled Treprostinil in Adult PH with ILD Including CPFE, ClinicalTrials.gov, 16 pages, Aug. 14, 2018.
NCT02630316, Safety and Efficacy of Inhaled Treprostinil in Adult PH with ILD Including CPFE, ClinicalTrials.gov, 16 pages, Aug. 17, 2018.
NCT02630316, Safety and Efficacy of Inhaled Treprostinil in Adult PH with ILD Including CPFE, ClinicalTrials.gov, 16 pages, Aug. 3, 2018.
NCT02630316, Safety and Efficacy of Inhaled Treprostinil in Adult PH with ILD Including CPFE, ClinicalTrials.gov, 16 pages, Aug. 7, 2019.
NCT02630316, Safety and Efficacy of Inhaled Treprostinil in Adult PH with ILD Including CPFE, ClinicalTrials.gov, 16 pages, Dec. 13, 2018.
NCT02630316, Safety and Efficacy of Inhaled Treprostinil in Adult PH with ILD Including CPFE, ClinicalTrials.gov, 16 pages, Dec. 17, 2018.
NCT02630316, Safety and Efficacy of Inhaled Treprostinil in Adult PH with ILD Including CPFE, ClinicalTrials.gov, 16 pages, Dec. 20, 2018.
NCT02630316, Safety and Efficacy of Inhaled Treprostinil in Adult PH with ILD Including CPFE, ClinicalTrials.gov, 16 pages, Feb. 14, 2019.
NCT02630316, Safety and Efficacy of Inhaled Treprostinil in Adult PH with ILD Including CPFE, ClinicalTrials.gov, 16 pages, Feb. 4, 2019.
NCT02630316, Safety and Efficacy of Inhaled Treprostinil in Adult PH with ILD Including CPFE, ClinicalTrials.gov, 16 pages, Jan. 24, 2019.
NCT02630316, Safety and Efficacy of Inhaled Treprostinil in Adult PH with ILD Including CPFE, ClinicalTrials.gov, 16 pages, Jan. 8, 2019.
NCT02630316, Safety and Efficacy of Inhaled Treprostinil in Adult PH with ILD Including CPFE, ClinicalTrials.gov, 16 pages, Jan. 9, 2019.
NCT02630316, Safety and Efficacy of Inhaled Treprostinil in Adult PH with ILD Including CPFE, ClinicalTrials.gov, 16 pages, Jul. 11, 2018.
NCT02630316, Safety and Efficacy of Inhaled Treprostinil in Adult PH with ILD Including CPFE, ClinicalTrials.gov, 16 pages, Jul. 20, 2018.
NCT02630316, Safety and Efficacy of Inhaled Treprostinil in Adult PH with ILD Including CPFE, ClinicalTrials.gov, 16 pages, Jun. 14, 2018.
NCT02630316, Safety and Efficacy of Inhaled Treprostinil in Adult PH with ILD Including CPFE, ClinicalTrials.gov, 16 pages, Jun. 14, 2019.
NCT02630316, Safety and Efficacy of Inhaled Treprostinil in Adult PH with ILD Including CPFE, ClinicalTrials.gov, 16 pages, Jun. 18, 2018.
NCT02630316, Safety and Efficacy of Inhaled Treprostinil in Adult PH with ILD Including CPFE, ClinicalTrials.gov, 16 pages, Jun. 21, 2019.
NCT02630316, Safety and Efficacy of Inhaled Treprostinil in Adult PH with ILD Including CPFE, ClinicalTrials.gov, 16 pages, Jun. 25, 2018.
NCT02630316, Safety and Efficacy of Inhaled Treprostinil in Adult PH with ILD Including CPFE, ClinicalTrials.gov, 16 pages, Mar. 13, 2019.
NCT02630316, Safety and Efficacy of Inhaled Treprostinil in Adult PH with ILD Including CPFE, ClinicalTrials.gov, 16 pages, Mar. 29, 2019.
NCT02630316, Safety and Efficacy of Inhaled Treprostinil in Adult PH with ILD Including CPFE, ClinicalTrials.gov, 16 pages, May 16, 2018.
NCT02630316, Safety and Efficacy of Inhaled Treprostinil in Adult PH with ILD Including CPFE, ClinicalTrials.gov, 16 pages, May 24, 2019.
NCT02630316, Safety and Efficacy of Inhaled Treprostinil in Adult PH with ILD Including CPFE, ClinicalTrials.gov, 16 pages, Nov. 2, 2018.
NCT02630316, Safety and Efficacy of Inhaled Treprostinil in Adult PH with ILD Including CPFE, ClinicalTrials.gov, 16 pages, Nov. 21, 2018.
NCT02630316, Safety and Efficacy of Inhaled Treprostinil in Adult PH with ILD Including CPFE, ClinicalTrials.gov, 16 pages, Nov. 7, 2018.
NCT02630316, Safety and Efficacy of Inhaled Treprostinil in Adult PH with ILD Including CPFE, ClinicalTrials.gov, 16 pages, Oct. 1, 2018.
NCT02630316, Safety and Efficacy of Inhaled Treprostinil in Adult PH with ILD Including CPFE, ClinicalTrials.gov, 16 pages, Oct. 11, 2018.
NCT02630316, Safety and Efficacy of Inhaled Treprostinil in Adult PH with ILD Including CPFE, ClinicalTrials.gov, 16 pages, Oct. 22, 2018.
NCT02630316, Safety and Efficacy of Inhaled Treprostinil in Adult PH with ILD Including CPFE, ClinicalTrials.gov, 16 pages, Sep. 24, 2018.
NCT02630316, Safety and Efficacy of Inhaled Treprostinil in Adult PH with ILD Including CPFE, ClinicalTrials.gov, 5 pages, Dec. 11, 2015.
NCT02630316, Safety and Efficacy of Inhaled Treprostinil in Adult PH with ILD Including CPFE, ClinicalTrials.gov, 5 pages, Feb. 24, 2016.
NCT02630316, Safety and Efficacy of Inhaled Treprostinil in Adult PH with ILD Including CPFE, ClinicalTrials.gov, 5 pages, Mar. 14, 2016.
NCT02630316, Safety and Efficacy of Inhaled Treprostinil in Adult PH with ILD Including CPFE, ClinicalTrials.gov, 6 pages, Aug. 15, 2016.
NCT02630316, Safety and Efficacy of Inhaled Treprostinil in Adult PH with ILD Including CPFE, ClinicalTrials.gov, 6 pages, Jun. 23, 2016.
NCT02630316, Safety and Efficacy of Inhaled Treprostinil in Adult PH with ILD Including CPFE, ClinicalTrials.gov, 6 pages, Jun. 6, 2016.
NCT02630316, Safety and Efficacy of Inhaled Treprostinil in Adult PH with ILD Including CPFE, ClinicalTrials.gov, 6 pages, Jun. 7, 2016.
NCT02630316, Safety and Efficacy of Inhaled Treprostinil in Adult PH with ILD Including CPFE, ClinicalTrials.gov, 6 pages, May 23, 2016.
NCT02630316, Safety and Efficacy of Inhaled Treprostinil in Adult PH with ILD Including CPFE, ClinicalTrials.gov, 6 pages, May 31, 2016.
NCT02630316, Safety and Efficacy of Inhaled Treprostinil in Adult PH with ILD Including CPFE, ClinicalTrials.gov, 6 pages, May 5, 2016.
NCT02630316, Safety and Efficacy of Inhaled Treprostinil in Adult PH with ILD Including CPFE, ClinicalTrials.gov, 7 pages, Aug. 26, 2016.
NCT02630316, Safety and Efficacy of Inhaled Treprostinil in Adult PH with ILD Including CPFE, ClinicalTrials.gov, 7 pages, Jul. 12, 2016.
NCT02630316, Safety and Efficacy of Inhaled Treprostinil in Adult PH with ILD Including CPFE, ClinicalTrials.gov, 7 pages, Jul. 21, 2016.

(56) References Cited

OTHER PUBLICATIONS

NCT02630316, Safety and Efficacy of Inhaled Treprostinil in Adult PH with ILD Including CPFE, ClinicalTrials.gov, 7 pages, Jul. 5, 2016.
NCT02630316, Safety and Efficacy of Inhaled Treprostinil in Adult PH with ILD Including CPFE, ClinicalTrials.gov, 7 pages, Sep. 9, 2016.
NCT02630316, Safety and Efficacy of Inhaled Treprostinil in Adult PH with ILD Including CPFE, ClinicalTrials.gov, 9 pages, Apr. 30, 2020.
NCT02630316, Safety and Efficacy of Inhaled Treprostinil in Adult PH with ILD Including CPFE, ClinicalTrials.gov, 9 pages, Feb. 26, 2020.
NCT02630316, Safety and Efficacy of Inhaled Treprostinil in Adult PH with ILD Including CPFE, ClinicalTrials.gov, 9 pages, Jan. 7, 2020.
NCT02630316, Safety and Efficacy of Inhaled Treprostinil in Adult PH with ILD Including CPFE, ClinicalTrials.gov, 9 pages, May 29, 2020.
NCT02630316, Safety and Efficacy of Inhaled Treprostinil in Adult PH with ILD Including CPFE, ClinicalTrials.gov, 9 pages, Nov. 1, 2016.
NCT02630316, Safety and Efficacy of Inhaled Treprostinil in Adult PH with ILD Including CPFE, ClinicalTrials.gov, 9 pages, Nov. 17, 2016.
NCT02630316, Safety and Efficacy of Inhaled Treprostinil in Adult PH with ILD Including CPFE, ClinicalTrials.gov, 9 pages, Nov. 9, 2016.
Nebu-Tec med. Produkte Eike Kern GmbH, VENTA-NEBR-ir A-I-C-I® Operating Instrutions, Sep. 2005.
Newman, S.P., "Aerosols," Chapter from Encyclopedia of Respiratory Medicine, 2006, 58-64.
Notes for Guidance on the Clinical Administration of Radiopharmaceuticals and Use of Sealed Radioactive Sources. Administration of Radioactive Substances Advisory Committee (ARSAC) (Mar. 2006). ARSAC Secretariat, Chilton, Didcot, Oxon. OX11 0rq.
Olin, Jeffrey W., D.O., "Thromboangiitis Obliterans (Buerger's Disease)," N. Engl. J. Med., 2000, 343:864-869.
Olschewski et al. for the German PPH Study Group, "Inhaled iloprost to treat severe pulmonary hypertension—An uncontrolled trial," Annals of Internal Medicine, 2000, 132, 435-443.
Olschewski et al., "Inhaled Iloprost for Severe Pulmonary Hypertension," The New England Journal of Medicine, Aug. 1, 2002, 347(5):322-329.
Olschewski et al., Aerosolized prostacyclin and iloprost in severe pulmonary hypertension,: Annals of Internal Medicine, 1996, 124, 820 824.
Olschewski et al., "Inhaled Iloprost for Severe Pulmonary Hypertension," N. Eng. J. Med., Aug. 1, 2002, 347(5):322-329.
Olschewski et al., "Inhaled prostacyclin and iloprost in severe pulmonary hypertension secondary to lung fibrosis," Am. Respir. Crit. Care Med., 1999, 160, 600-607.
Olschewski et al., "Pharmacodynamics and pharmacokinetics of inhaled iloprost, aerosolized by three different devices, in severe pulmonary hypertension," Chest, 2003, 124, 1294-1304.
Olschewski et al., "Prostacyclin and its analogues in the treatment of pulmonary hypertension," Pharmacology and Therapeutics, 2004, 102, 139-153.
Olschewski et al., "Recovery from circulatory shock in severe primary pulmonary hypertension (PPH) with aerosolization of iloprost," Intensive Care Med., 1998, 24, 631-634.
Olschewski, Horst, "Therapie der pulmonalen Hypertonie," Pneumologe, 2004, 1:95-101.
OPTINEB®-ir Operating Instructions, Unit Type ON-100/2-2.4 Mhz, 2005, 33 pages, verified English translation.
Order Terminating IPR2017-01621, *Watson Laboratories, Inc.* (Petitioner) v. *United Therapeutics, Inc.* (Patent Owner), Aug. 27, 2018, 3 pages.
Order Terminating IPR2017-01622, *Watson Laboratories, Inc.* (Petitioner) v. *United Therapeutics, Inc.* (Patent Owner), Aug. 27, 2018, 3 pages.
ORENITRAM label, Oct. 2019, 17 pages.
Osterweil, Neil, "Inhaled treprostinil improves walk distance in patients with ILD-associated pulmonary hypertension," Chest Physician, Jul. 6, 2020, 1-5.
Osterweil, Neil, "Treprostinil Improves Walk Distance in Pulmonary Hypertension," Jul. 9, 2020, 9 pages, www.medscape.com/viewarticle/933674.
Pappert et al., "Aerosolized Prostacyclin Versus Inhaled Nitric Oxide in Children with Severe Acute Respiratory Distress Syndrome," Anesthesiology, Jun. 1995, 82(6): 1507-1511.
Parikh et al., "Safety and Tolerability of High-dose Inhaled Treprostinil in Pulmonary Hypertension," J. Cardiovasc. Pharmacol., Apr. 2016, 67(4):322-325.
Patent Owner Preliminary Response, May 17, 2021, 67 pages, IPR2021-00406, Patent No. 10,716,793, *Liquidia Technologies, Inc.*(Petitioner) v. *United Therapeutics Corp.* (Patent Owner).
Patent Owner Response dated Nov. 10, 2021 in IPR2021-00406, 75 pages.
Petition for Inter Partes Review of U.S. Pat. No. 10,716,793, *Liquidia Technologies, Inc.* (petitioner) v. *United Therapeutics Corporation* (patent owner), IPR2021-00406, and Exhibits 1002, 1003, 1004, 1005 and 1036.
Petitioner's Reply, Feb. 10, 2022, 42 pages, *Liquidia Technologies, Inc.* (Petitioner) v. *United Therapeutics Corporation* (Patent Owner), IPR2021-00406.
Pharmacokinetics of Inhaled Drugs, Exhibit 2058, 3 pages, *Liquidia Technologies, Inc.* (Petitioner) v. *United Therapeutics Corporation* (Patent Owner), IPR2021-00406.
Pitcairn et al., "Deposition of Corticosteroid Aerosol in the Human Lung by Respimat Soft Mist Inhaler Compared to Deposition by Metered Dose Inhaler or by Turbuhaler Dry Powder Inhaler," Journal of Aerosol Medicine, 2005, 18(3):264-272.
Plaintiff UTC's Response to Defendant's Motion for Leave to Submit a 1-Page Supplemental Brief, *United Therapeutics Corporation* (Plaintiff) v. *Liquidia Technologies, Inc.* (Defendant), C.A. No. 23-975 (RGA)(SRF), filed May 7, 2024, 5 pages.
Plaintiff's Brief in Support of its Motion for Preliminary Injunction, *United Therapeutics Corporation* (Plaintiff) v. *Liquidia Technologies, Inc.* (Defendant), C.A. No. 23-975 (RGA), Mar. 4, 2024, 27 pages.
Plaintiff's Reply Brief in Support of its Motion for Preliminary Injunction, *United Therapeutics Corporation* (Plaintiff) v. *Liquidia Technologies, Inc.* (Defendant), C.A. No. 23-975 (RGA)(SRF), filed Apr. 22, 2024, 20 pages.
Plaintiff's Responses and Objections to Defendant's First Set of Interrogatories to Plaintiff (Nos. 1-6), *United Therapeutics Corporation*, Plaintiff v. *Liquidia Technologies, Inc.*, Defendant, C.A. No. 23-975 (RGA)(SRF), Jul. 5, 2024, 57 pages.
Prober et al., "Technical Report: Precautions Regarding the Use of Aerosolized Antibiotics," Pediatrics, Dec. 2000, 106(6):1-6.
Publications of the International Commission on Radiological Protection (ICRP) (1977) Recommendations of the International Commission on Radiological Protection 26.
Pulmonary Delivery, ONdrugDelivery, 2006, 5 pages.
Pulmozyme label, Apr. 2005, 2 pages.
Rau, Joseph L., "Determinants of Patient Adherence to an Aerosol Regimen," Respiratory Care, Oct. 2005, 50(10):1346-1359.
Remodulin label, Nov. 2004, 11 pages.
Rigby, Jonathan, Aradigm Corporation, "Technological advances for success: Product pipeline in targeted pulmonary delivery," Pulmonary Delivery Innovative Technologies Breathing New Life into Inhalable Therapeutics, ONdrugDelivery, http://www.ondrugdelivery.com/publications/Pulmonary.pdf, 2006, 17-19.
Ruan et al., "Prostacyclin therapy for pulmonary arterial hypertension," Texas Heart Institute Journal (2010) vol. 37, No. 4, pp. 391-399.
Rubin et al., "Evaluation and Management of the Patient with Pulmonary Arterial Hypertension," Ann. Intern. Med., 2005, 143:282-292.

(56) References Cited

OTHER PUBLICATIONS

Rubin et al., "Pulmonary Arterial Hypertension: A Look to the Future," Journal of the American College of Cardiology, Jun. 18, 2004, 43(12, Suppl.S):89S-90S.
Saini et al., "Effect of Electrostatic Charge and Size Distributions on Respirable Aerosol Deposition in Lung Model," Industry Applications Conference, 2004, 39th IAS Annual Meeting, Conference Record of the 2004 IEEE Seattle, WA, Oct. 3-7, 2004, 2:948-952.
Sandifer et al., "Effects of Aerosol vs IV UT-15 on Prostaglandin H2 Analog-Induced Pulmonary Hypertension in Sheep," Chest, 2005, 128:616S.
Sandifer et al., "Potent effects of aerosol compared with intravenous treprostinil on the pulmonary circulation," J. Appl. Physiol., 2005, 99:2363-2368.
Santak et al., "Prostacyclin aerosol in an infant with pulmonary hypertension," Eur. J. Pediatr., 1995, 154, 233-235.
Scientific discussion for the approval of Ventavis, European Medicines Agency (EMEA), Oct. 20, 2004, 30 pages.
Sene et al., "Preliminary Report: Aerosol-Mediated Delivery of Recombinant Adenovirus to the Airways of Nonhuman Primates," Human Gene Therapy, Dec. 1995, 6:1587-1593.
Simonneau et al., "Haemodynamic definitions and updated clinical classification of pulmonary hypertension," Eur. Respir. J., 2019, 53: 1801913, 13 pages.
Soditt et al., "Improvement of oxygenation induced by aerosolized prostacyclin in a preterm infant with persistent pulmonary hypertension of the newborn," Intensive Care Med., 1997, 23, 1275-1278.
Sorbera et al., "UT-15. Treatment of Pulmonary Hypertension Treatment of Peripheral Vascular Disease," Drug of the Future, 2001, 26(4):364-374.
Steffen et al., "The Effects of 15AU81, a Chemically Stable Prostacyclin Analog, on the Cardiovascular and Renin-Angiotensis Systems of Anesthetized Dogs," Prostaglandins, Leukotrienes and Essential Fatty Acids, 1991, 43:277-286.
Stein et al., "The History of Therapeutic Aerosols: A Chronological Review," Journal of Aerosol Medicine and Pulmonary Drug Delivery, 2017, 30(1):20-41.
Steven et al., "Pulmonary hypertension in chronic lung disease and hypoxia," Eur. Respir. J., Dec. 13, 2018, https://doi: 10.1183/13993003.01914-2018, 15 pages.
Stricker et al., "Sustained improvement of performance and haemodynamics with long-term aerosolized prostacyclin therapy in severe pulmonary hypertension," Schweiz Med. Wochenschr., 1999, 129, 923- 927.
Telko et al., "Dry Powder Inhalation Formulation," Respiratory Care, Sep. 2005, 50(9):1209-1227.
Testimony of Dr. Hill, Mar. 29, 2022, *United Therapeutics Corporation* (Plaintiff) v. *Liquidia Technologies, Inc., C.A.* No. 20-755-RGA-JLH vol. II, 5 pages.
Trammell et al., "Use of pulmonary arterial hypertension-approved therapy in the treatment of non-group 1 pulmonary hypertension at US referral centers," Pulm. Circ., 2015, 5(2):356-363.
Trial Opinion, Aug. 31, 2022, *United Therapeutics Corporation* (Plaintiff) v. *Liquidia Technologies, Inc.* (Defendant), C.A. 20-755-RGA, 55 pages.
Tyvaso label, 2009, 49 pages.
United Therapeutics Announces FDA Approval and Launch of Tyvaso? for the Treatment of Pulmonary Hypertension Associated with Interstitial Lung Disease, Apr. 1, 2021, 7 pages.
United Therapeutics Announces New England Journal of Medicine Publication in the INCREASE Study Evaluating Tyvaso? in Pulmonary Hypertension Associated with Interstitial Lung Disease, Jan. 13, 2021.
*United Therapeutics Corporation* (Plaintiff) v. *Liquidia Technologies, Inc.* (Defendant) Complaint, United States District Court for the Middle District of North Carolina, Civil Action No. 1:25-cv-00368-TDS-JLW, May 9, 2025, with exhibits, 127 pages.
*United Therapeutics Corporation* (Plaintiff) v. *Liquidia Technologies, Inc.* (Defendant), Defendant Liquidia Technologies, Inc.'s Opposition to Plaintiff's Motion for a Temporary Restraining Order, United States District Court for the Middle District of North Carolina, Civil Action No. 1:25-cv-00368-TDS-JLW, May 19, 2025, 35 pages.
*United Therapeutics Corporation* (Plaintiff) v. *Liquidia Technologies, Inc.* (Defendant), Memorandum Opinion and Order, United States District Court for the Middle District of North Carolina, Civil Action No. 1:25-cv-00368-TDS-JLW, May 30, 2025, 41 pages.
United Therapeutics INCREASE Study of Tyvaso® Meets Primary and All Secondary Endpoints, Feb. 24, 2020, 7 pages.
United Therapeutics Press Release,"United Therapeutics Announces FDA Approval of Third Generation Nebulizer for the Tyvaso Inhalation System," Oct. 23, 2017, 5 pages.
Vachiery et al., "Transitioning From IV Epoprostenol to Subcutaneous Treprostinil in Pulmonary Arterial Hypertension," Chest, 2002, 121:1561-1565.
Van Heerden et al., "Inhaled aerosolized prostacyclin as a selective pulmonary vasodilator for the treatment of severe hypertension," Anaesthesia and Intensive Care, 1996, 24, 87-90.
Van Heerden et al., "Re: Delivery of inhaled aerosolized prostacyclin (IAP)," Anaesthesia and Intensive Care, 1996, 24, 624-625.
VENTAVIS (iloprost) Inhalation Solution product information, Dec. 2004, 15 pages.
Voswinckel et al., "Acute effects of the combination of sildenafil and inhaled treprostinil on haemodynamics and gas exchange in pulmonary hypertension," Pulmonary Pharmacology & Therapeutics, 2008, 21, 824-832.
Voswinckel et al., "Favorable Effects of Inhaled Treprostinil in Severe Pulmonary Hypertension: Results from Randomized Controlled Pilot Studies" J. Am. Coll. Cardiol., 2006, 48(8):1672-1681.
Voswinckel et al., "Inhaled Treprostinil for Treatment of Chronic Pulmonary Arterial Hypertension," Annals of Internal Medicine, Jan. 17, 2006, 144(2):149-150.
Voswinckel et al., "Inhaled treprostinil is a potent pulmonary vasodilator in severe pulmonary hypertension," European Heart Journal, Journal of the European Society of Cardiology, ESC Congress, Aug. 28-Sep. 1, 2004, Munich, Germany, p. 22, abstract 218.
Voswinckel et al., "Inhaled Treprostinil Sodium (TRE) for the Treatment of Pulmonary Hypertension," Circulation, Oct. 26, 2004, Supplement, 110(17):295, abstract 1414.
Voswinckel et al., Abstract 1414, "Inhaled Treprostinil Sodium (TRE) for the Treatment of Pulmonary Hypertension," Abstracts from the 2004 Scientific Sessions of the American Heart Association, Circulation, Oct. 26, 2004, 110(17Supp):III-295.
Voswinckel et al., Abstract 218, "Inhaled treprostinil is a potent pulmonary vasodilator in severe pulmonary hypertension," European Heart Journal, 2004, 25:22.
Walmrath et al., "Aerosolized prostacyclin in adult respiratory distress syndrome," Lancet, 1993, 342:961-962.
Walmrath et al., "Direct Comparison of Inhaled Nitric Oxide and Aerosolized Prostacyclin in Acute Respiratory Distress Syndrome," Am. J. Respir. Crit. Care Med., 1996, 153:991-996.
Walmrath et al., "Effects of inhaled versus intravenous vasodilators in experimental pulmonary hypertension," Eur. Respir. J., 1997, 10, 1084-1092.
Wang et al., "Hemodynamic and gas exchange effects of inhaled iloprost in patients with COPD and pulmonary hypertension," International Journal of COPD, 2017, 12:3353-3360.
Wasserman et al., "Bronchodilator effects of prostacyclin (PGI2) in dogs and guinea pigs," European Journal of Pharmacology, 1980, 66, 53-63.
*Watson Laboratories, Inc.* (Petitioner) v. *United Therapeutics Corp.* (Patent Owner), Decision Granting Institution of Inter Partes Review 37 C.F.R. 42.108, IRP2017-01621, U.S. Pat. No. 9,358,240, Jan. 11, 2018.
*Watson Laboratories, Inc.* (Petitioner) v. *United Therapeutics Corp.* (Patent Owner), Decision Granting Institution of Inter Partes Review 37 C.F.R. 42.108, IRP2017-01622, U.S. Pat. No. 9,339,507, Jan. 11, 2018.
*Watson Laboratories, Inc.* (Petitioner) v. *United Therapeutics, Inc.* (Patent Owner), Petition for Inter Partes Review, IRP2017-01621, U.S. Pat. No. 9,358,240, with only Exhibits 1002, 1059, 1161 and 1164 and not including exhibits already provide with C2.

(56) References Cited

OTHER PUBLICATIONS

*Watson Laboratories, Inc.* (Petitioner) v. *United Therapeutics, Inc.* (Patent Owner), Petition for Inter Partes Review, IRP2017-01622, U.S. Pat. No. 9,339,507, with all Exhibits on exhibit list.
Waxman et al., "Inhaled Treprostinil in Pulmonary Hypertension Due to Interstitial Lung Disease," The New England Journal of Medicine, 2021, 284:325-334.
Webb et al., "The use of inhaled aerosolized prostacyclin (IAP) in the treatment of pulmonary hypertension secondary to pulmonary embolism," Intensive Care Med., 1996, 22, 353-355.
Welsh, Erin T., Ma, "Inhaled treprostinil improves outcomes in ILD-associated pulmonary hypertension," Jun. 30, 2020, 2 pages, www.healio.com/news/pulmonology/20200630/inhaled-treprostinil-improves-outcomes-in-ildassociated-pulmonary-hypertension.
Welsh, Erin T., Ma., FDA approves inhaled treprostinil for pulmonary hypertension associated with ILD, Apr. 5, 2021, www.healio.com/news/pulmonology/20210405/fda-approves-inhaled-treprostinil-for-pulmonary-hypertension-associated-with-ild.
Wensel et al., "Effects of iloprost inhalation on exercise capacity and ventilator efficiency in patients with primary pulmonary hypertension," Circulation, 2000, 101, 2388-2392.
Wetzel, R.C., "Aerosolized prostacyclin: in search of the ideal pulmonary vasodilator," Anesthesiology, 1995, 82, 1315-1317.
Whittle et al., "Binding and activity of the prostacyclin receptor (IP) agonists, treprostinil and iloprost, at human prostanoid receptors: Treprostinil is a potent DP1 and EP2 agonist," Biochemical Pharmacology, 2012, 84:68-75.
Wielosz et al., "Heart involvement in systemic sclerosis: analysis of four cases," Ann. Acad. Med. Stetin., 2012, 58(1):33-39, with English abstract.
Wittwer et al., "Inhalative Pre-Treatment of Donor Lungs Using the Aerosolized Prostacyclin Analog Iliprost Ameliorates Reperfusion Injury," J. Heart Lung Transplant, 2005, 24:1673-1679.
Zanen et al., "Optimal particle size for beta 2 agonist and anticholinergic aerosols in patients with severe airflow obstruction," Thorax, 1996, 51, 977-980.
Zanen et al., "The optimal particle size for β-adrenergic aerosols in mild asthmatics," International Journal of Pharmaceutics, 1994, 107, 211-217.
Ziegler et al., "Comparison of Cascade Impaction and Laser Diffraction for Particle Size Distribution Measurements," Journal of Aerosol Medicine, 2005, 18(3):311-324.
Zierenberg et al., "The Respimat, a New Soft Mist Inhaler for Delivering Drugs to the Lungs," Modified-Release Drug Delivery Technology, 2002, Chapter 78, 925-933.

* cited by examiner

Observed
MMRM
MCMC
Inhaled treprostinil
Placebo
148
132
125
121
148
131
121
120
Change from Baseline (m)
30
25
20
15
10
5
0
-5
-10
-15
-20
Week
0
4
8
12
16

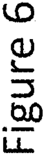
Figure 6
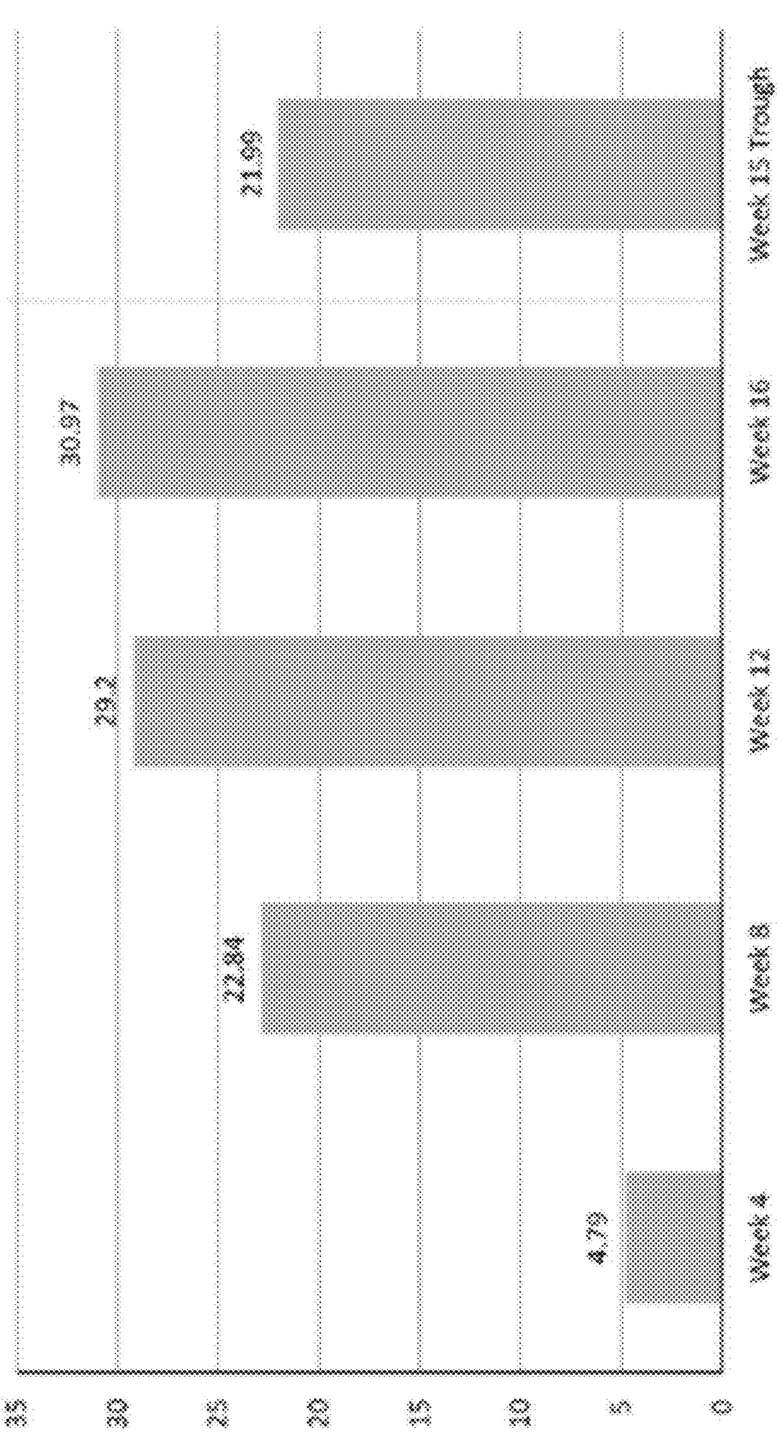

TREATMENT FOR INTERSTITIAL LUNG DISEASE

RELATED APPLICATIONS

The present application is a Continuation of U.S. Ser. No. 18/586,056, filed Feb. 23, 2024, which is a Continuation of U.S. application Ser. No. 18/219,944, filed Jul. 10, 2023, which is a Continuation of U.S. application Ser. No. 17/233,061, filed Apr. 16, 2021, now U.S. patent Ser. No. 11/826,327, which claims priority to U.S. provisional application No. 63/011,810 filed Apr. 17, 2020 and U.S. provisional application No. 63/160,611 filed Mar. 12, 2021, each of which is incorporated herein by reference in its entirety.

FIELD

The present application generally relates to methods of treating a disease with prostacyclins and more particularly, to treating a disease with treprostinil.

BACKGROUND

Interstitial lung disease (ILD), or diffuse parenchymal lung disease (DPLD), is a group of lung diseases affecting the interstitium (the tissue and space around the alveoli, including air sacs of the lungs). It concerns alveolar epithelium, pulmonary capillary endothelium, basement membrane, and perivascular and perilymphatic tissues. It may occur when an injury to the lungs triggers an abnormal healing response. Such abnormal response may result in idiopathic pulmonary fibrosis (IPF). Currently, two drugs are approved by FDA for treatment of IPF, which is the most common form of PF: nintedanib and pirfenidone. The average rate of survival for someone with interstitial lung disease is currently between 3 and 5 years (Meyer et al., 2017). There exists a need for the identification of new pharmaceutical treatments for ILD.

SUMMARY

In one aspect, a method of treating a pulmonary hypertension due to a condition which is selected from a chronic lung disease, hypoxia and a combination thereof, comprises administering to a subject having the pulmonary hypertension due to the condition selected from a chronic lung disease, hypoxia and a combination thereof an effective amount of treprostinil, a prodrug thereof or a pharmaceutically acceptable salt thereof.

In one aspect, a method of treating interstitial lung disease (ILD) in a subject in need thereof is provided, comprises administering to the subject a therapeutically effective amount of treprostinil, a prodrug, salt, or ester thereof. In an embodiment, the subject has pulmonary hypertension associated with ILD.

In one aspect, a method of reducing pulmonary function decline in a subject with ILD is provided, comprises administering to the subject treprostinil, a prodrug, salt, or ester thereof.

In one aspect, a method of increasing forced vital capacity (FVC) in a subject suffering from ILD is provided, comprises administering to the subject treprostinil, a prodrug, salt, or ester thereof.

In some embodiments, administration of treprostinil, a prodrug, salt, or ester thereof may result in an increase of FVC of at least 20%, at least 40%, at least 60%, at least 80%, at least 90%, or at least 100% compared to the FVC prior to the start of treatment. The FVC can be assessed prior to the start of treatment and at intervals after the start of treatment. For example, the pre-treatment FVC can be compared to the FVC measured at one week, four weeks, eight weeks, or sixteen weeks after the start of treatment.

In some embodiments, administering an effective amount of treprostinil, its prodrug, its pharmaceutically acceptable salt or a pharmaceutically acceptable salt of its prodrug may provide an improvement, which may be statistically significant, in forced vital capacity (FVC) in a subject with a condition selected from a chronic lung disease, such as an ILD or IPF and/or hypoxia. For example, the FVC may be higher in a patient subpopulation with the chronic lung disease and/or hypoxia, who was administered the effective amount of treprostinil, its prodrug, its pharmaceutically acceptable salt or a pharmaceutically acceptable salt of its prodrug for at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks or at least 16 weeks or at least 20 weeks or at least 24 weeks, or at least 28 weeks or at least 32 weeks, or at least 36 weeks or at least 40 weeks or at least 44 weeks or at least 48 weeks or at least 52 weeks, compared to a patient subpopulation with the same condition, which was administered a placebo instead of treprostinil. For example, the FVC value may be higher by at least 10 ml or at least 15 ml or at least 20 ml or at least 25 ml or at least 30 ml or at least 35 ml or at least 40 ml or at least 45 ml after at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks or at least 16 weeks of the administering in the patient subpopulation with the chronic lung disease and/or hypoxia, who was administered the effective amount of treprostinil, its prodrug, its pharmaceutically acceptable salt or a pharmaceutically acceptable salt of its prodrug compared to the patient subpopulation with the same condition, which was administered a placebo instead of treprostinil. In patients with a chronic lung disease, such as interstitial lung disease, and/or hypoxia, an FVC value usually decreases with time when untreated. Thus, administering the effective amount of treprostinil, its prodrug, its pharmaceutically acceptable salt or a pharmaceutically acceptable salt may increase an FVC value compared to an FVC value before the administering; maintain an FVC value within 5%, 10% or 20% within the FVC value prior to the administering; or reduce a decrease of an FVC value with time compared to a decrease in an FVC value with no administering the effective amount of treprostinil, its prodrug, its pharmaceutically acceptable salt or a pharmaceutically acceptable salt, such a decrease in an FVC value when placebo is administered instead of treprostinil, its prodrug, its pharmaceutically acceptable salt or a pharmaceutically acceptable salt.

In some embodiments, the ILD comprises one or more of idiopathic pulmonary fibrosis (IPF), desquamative interstitial pneumonia (DIP), acute interstitial pneumonia (AIP), nonspecific interstitial pneumonia (NSIP), respiratory bronchiolitis-associated interstitial lung disease (RB-ILD), cryptogenic organizing pneumonia (COP), lymphoid interstitial pneumonia (LIP), sarcoidosis, rheumatoid arthritis, systemic lupus erythematosus, systemic sclerosis, polymyositis, dermatomyositis, antisynthetase syndrome, silicosis, asbestosis, occupational lung disease, chronic hypersensitivity pneumonitis, idiopathic interstitial pneumonia (IIP), an autoimmune ILD, lymphangioleiomyomatosis (LAM), Langerhan's cell histiocytosis (LCH), drug associated ILD, vasculitis, granulomatosis, and berylliosis. In some embodiments, the ILD comprises IPF. In some embodiments, the ILD comprises systemic sclerosis-associated interstitial lung disease (SSc-ILD).

In some embodiments, the ILD was induced from antibiotics, chemotherapy, antiarrhythmic agents, coronavirus disease 2019 (COVID-19), atypical pneumonia, *pneumocystis* pneumonia, tuberculosis (TB), *Chlamydia trachomatis*, respiratory syncytial virus, or lymphangitic carcinomatosis.

In some embodiments, the subject has one or more of surfactant-protein-B deficiency, surfactant-protein-C deficiency, ABCA3-deficiency, brain lung thyroid syndrome, congenital pulmonary alveolar proteinosis, alveolar capillary dysplasia, mutations in telomerase reverse transcriptase, mutations in telomerase RNA component, mutations in the regulator of telomere elongation helicase 1, and mutations in poly(A)-specific ribonuclease.

In some embodiments, the subject has one or more symptoms of shortness of breath, fatigue, weight loss, dry cough, chest pain, and lung hemorrhage. In some embodiments, after administration the symptom is improved by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, as measured by a medically-recognized technique. In some embodiments, the medically-recognized technique comprises one or more of Modified Medical Research Council (MMRC) Dyspnoea Scale, Modified Borg Dyspnoea Scale (0-10), Chalder Fatigue Scale, weight measurement scale, visual analogue scale (VAS) for cough, King's Brief Interstitial Lung Disease Questionnaire, Leicester Cough Questionnaire (LCQ), Living with IPF (L-IPF, see e.g. Am J Respir Crit Care Med Vol 202, Iss 12, pp 1689-1697, Dec. 15, 2020), computed tomography (CT) scan, X-ray, multiple magnetic resonance imaging (MRI), pulmonary function testing (PFT), spirometry, lung volumes, maximal respiratory pressure, diffusing capacity, oxygen desaturation, and arterial blood gas evaluation.

In some embodiments, treprostinil, a prodrug, salt, or ester thereof is administered in a pharmaceutical composition comprising treprostinil, a prodrug, salt, or ester thereof and a pharmaceutically acceptable carrier or excipient.

In some embodiments, the administration comprises at least one of oral, inhalation, subcutaneous, nasal, intravenous, intramuscular, sublingual, buccal, rectal, vaginal, and transdermal administration. In some embodiments, the administration comprises inhalation. In some embodiments, one inhalation dosing event comprises from 1 to 20 breaths, wherein at least one inhalation dosing event per day is administered.

In some embodiments, the method comprises administration of at least one additional active agent to treat the ILD. In some embodiments, the at least one additional active agent comprises a corticosteroid, mycophenolic acid, mycophenolate mofetil, azathioprine, cyclophosphamide, rituximab, pirfenidone, or nintedanib. In some embodiments, the at least one additional active agent and treprostinil, a prodrug, salt, or ester thereof, are administered via a method selected from the group consisting of (a) concomitantly; (b) as an admixture; (c) separately and simultaneously or concurrently; and (d) separately and sequentially.

In some embodiments, administration is once, twice, thrice, four times, five times, or six times per day. In some embodiments, administration is for a period selected from the group consisting of about 1 day, about 1 day to about 3 days, about 3 days to about 6 days, about 6 days to about 9 days, about 9 days to about 12 days, about 12 days to about 15 days, about 15 days to about 18 days, about 18 days to about 21 days, about 21 days to about 24 days, about 24 days to about 27 days, about 27 days to about 30 days, or about greater than 30 days.

In some embodiments, a method of treating a pulmonary hypertension due to a condition which is selected from a chronic lung disease, hypoxia and a combination thereof, comprises administering to a subject having the pulmonary hypertension due to the condition selected from a chronic lung disease, hypoxia and a combination thereof an effective amount of treprostinil, a prodrug thereof or a pharmaceutically acceptable salt thereof.

In some embodiments, the subject is a human.

FIGURES

FIG. 1 shows a Kaplan-Meier plot of time to exacerbation of underlying lung disease over a 16-week period of treprostinil treatment. CI stands for confidence interval; HR stands for hazard ratio. Subjects who discontinued from the study early had their time to first clinical worsening event censored at their last visit. Subjects who did not experience a clinical worsening event had their time to first clinical worsening event censored at the study termination date. (1) P-value was calculated with log-rank test stratified by baseline 6-minute walk distance category. (2) Hazard ratio, 95% CI, and p-value were calculated with proportional hazards model with treatment and baseline 6-minute walk distance (continuous) as explanatory variables.

FIG. 2 outlines a plan for the clinical study presented in Example 3. Of 462 patients screened for eligibility, 326 patients underwent randomization and received at least one dose of the assigned treprostinil or placebo (included in the intention-to-treat and safety populations). Of the patients who underwent randomization, 40 patients in the treprostinil group and 38 in the placebo group discontinued the assigned regimen prematurely. These patients were not withdrawn from the trial but were encouraged to remain and complete assessments through week 16; 33 patients in the treprostinil group and 35 in the placebo group discontinued trial participation before week 16.

FIG. 3 shows mean change from baseline in peak 6-minute walking distance through week 16 in the clinical study presented in Example 3. Shown are mean (±SE) changes from baseline (dashed line) in peak 6-minute walk distance over the 16-week trial period. The data shown are for patients with available data (observed) as well as for the results of two analysis methods used to account for missing data. The values shown at each data point indicate the number of patients assessed at that time point. The primary analysis used mixed-model repeat-measurement (MMRM) methods, with the assumption that missing data were missing at random. The model included the change from baseline to peak 6-minute walk distance as the dependent variable, with treatment, week, and treatment-by-week interaction as fixed effects, and the baseline 6-minute walk distance as a covariate. A sensitivity analysis for the primary end point was performed with the use of a multiple imputation approach with a multivariate normal imputation model using the Markov chain Monte Carlo (MCMC) method. The imputation model included treatment group, all scheduled visits, patient's sex, and patient's age at randomization. The confidence intervals have not been adjusted for multiplicity and cannot be used to infer definitive treatment effects.

FIG. 4 shows 6-Minute Walk Distance Treatment Effect Using Mixed Model Repeated Measurement Through Week 16. A longitudinal data analysis using mixed model repeated measurement was also performed to estimate the treatment difference in change in peak 6-minute walk distance at Week 16. The mixed model repeated measurement includes the change from baseline in peak 6-minute walk distance as the dependent variable; treatment, week, and treatment by week interaction as fixed effects; and baseline 6-minute walk distance as a covariate. An unstructured variance/covariance structure shared across treatment groups was used to model the within-subject errors.

FIG. 5 shows Forest Plot on Subgroup Analyses of Peak 6-Minute Walk Distance (meter) at Week 16. 6MWD stands for 6-minute walk distance; CI stands for confidence interval; ILD stands for interstitial lung disease; PH stands for pulmonary hypertension; PVR stands for pulmonary vascular resistance; LS mean differences and their 95% confidence intervals, and p-values are from the mixed model repeated measures. The confidence intervals have not been adjusted for multiplicity and cannot be used to infer definitive treatment effects. For etiology, the "other" category includes chronic hypersensitivity pneumonitis and occupational lung disease.

FIG. 6 shows 6-Minute Walk Distance Treatment Effect Using Multiple Imputation Through Week 16. Multiple imputation approach using a multivariate normal imputation model with the Markov Chain Monte Carlo method. P-values are obtained from 100 multiple imputations using Markov Chain Monte Carlo estimation with ANCOVA model with change from Baseline in 6-minute walk distance as the dependent variable, treatment as fixed effect, and Baseline 6-minute walk distance measurement as a covariate.

FIG. 7 shows NT-proBNP Results by Study Visit (pg/mL). CI stands for confidence interval; IQR stands for interquartile range; NT-proBNP stands for N-terminal pro-brain natriuretic peptide. As displayed above, inhaled treprostinil was associated with a 42% reduction in NT-proBNP compared to placebo at Week 16 (Treatment Ratio 0.58; 95% CI: 0.47, 0.72; P<0.001). Only subjects with a Baseline NT-proBNP measurement are included in this analysis. P-values, estimated treatment ratio, and associated 95% CIs (LS Mean difference expressed as ratio) are obtained from the analysis of covariance with change from baseline in logtransformed data in NT-proBNP as the dependent variable, treatment as the fixed effect, and log-transformed baseline NT-proBNP as a covariate. The confidence intervals have not been adjusted for multiplicity and cannot be used to infer definitive treatment effects.

FIG. 8 shows Hodges-Lehmann Estimate of Treatment Effect for 6-Minute Walk Distance Through Week 16. For those subjects who withdrew early due to death, were too ill to walk, or had no 6-minute walk distance measurement due to a clinical worsening event, the 6-minute walk distance was set to 0; for all other withdrawals without a measurement, last observation carried forward was used for imputation. P-values are obtained from nonparametric ANCOVA adjusted for Baseline 6-minute walk distance category.

DETAILED DESCRIPTION

Figure 1:
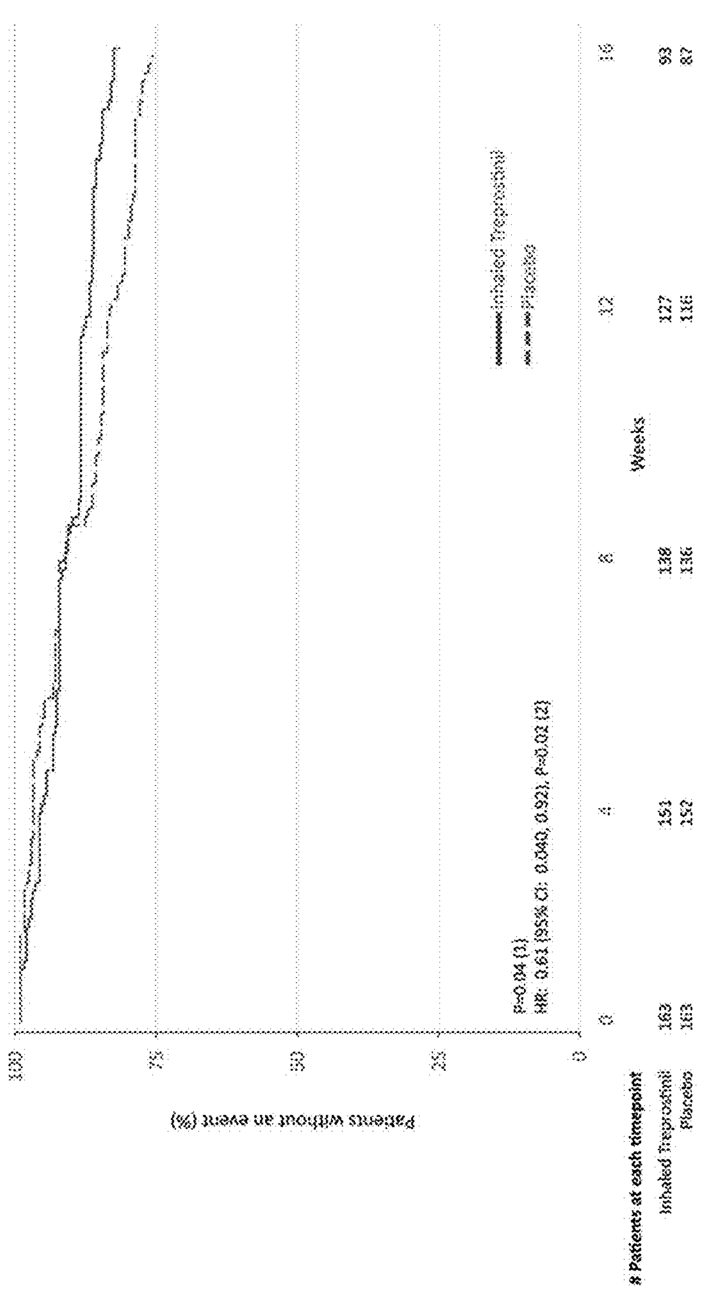

It is noted that, as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

As used herein, the term "comprising" or "comprises" is intended to mean that the compositions and methods include the recited elements, but do not exclude others. A composition or method "consisting essentially" of the elements as defined herein would not exclude other materials or steps that do not materially affect the basic and novel characteristic(s) of the claimed technology. "Consisting of" shall mean excluding more than trace elements of other ingredients and substantial method steps. Embodiments defined by each of these transition terms are within the scope of this technology. When an embodiment is defined by one of these terms (e.g., "comprising") it should be understood that this disclosure also includes alternative embodiments, such as "consisting essentially of" and "consisting of" for said embodiment.

"Subject" refers to an animal, such as a mammal (including a human), that has been or will be the object of treatment, observation or experiment. "Subject" and "patient" may be used interchangeably, unless otherwise indicated. The methods described herein may be useful in human therapy and/or veterinary applications. In some embodiments, the subject is a mammal. In some embodiments, the subject is a human.

The terms "therapeutically effective amount," "effective amount," and "pharmaceutically effective amount" are used interchangeably and refer to an amount of a compound that is sufficient to effect treatment as defined below, when administered to a patient (e.g., a human) in need of such treatment in one or more doses. The therapeutically effective amount will vary depending upon the patient, the disease being treated, the weight and/or age of the patient, the severity of the disease, or the manner of administration as determined by a qualified prescriber or care giver. The therapeutically effective amount can be determined by titrating the dose upwards from a starting dose, either in terms of dose by administration or frequency of administration. In some embodiments, the therapeutically effective dose is determined by titrating the dose upwards until the maximum tolerated dose for the individual subject is determined.

The term "treatment" or "treating" means administering a compound disclosed herein for the purpose of (i) delaying the onset of a disease, that is, causing the clinical symptoms of the disease not to develop or delaying the development thereof; (ii) inhibiting the disease, that is, arresting the development of clinical symptoms; and/or (iii) relieving the disease, that is, causing the regression of clinical symptoms or the severity thereof.

The term "pulmonary fibrosis" is a condition characterized by scarring and thickening of the lungs. Symptoms include shortness of breath, fatigue, weakness, chronic dry, hacking cough, loss of appetite, and discomfort in the chest. Eventually the scarring in the lung becomes replaced with fibrotic tissue resulting in loss of the lung's ability to transfer oxygen to the blood.

Unless defined otherwise, all technical and scientific terms used herein have the same meaning as commonly understood by one of ordinary skill in the art to which this present technology belongs. Although any methods and materials similar or equivalent to those described herein can also be used in the practice or testing of the present technology, representative illustrative methods and materials are described herein.

All numerical designations, e.g., pH, temperature, time, concentration, dose, and molecular weight, including ranges, are approximations which are varied (+) or (−) by increments of 0.05%, 1%, 2%, 5%, 10% or 20%. It is to be understood, although not always explicitly stated that all numerical designations are preceded by the term "about."

Where a range of values is provided, it is understood that each intervening value, to the tenth of the unit of the lower limit unless the context clearly dictates otherwise, between the upper and lower limit of that range and any other stated or intervening value in that stated range, is encompassed within the present technology. The upper and lower limits of these smaller ranges may independently be included in the smaller ranges and are also encompassed within the present technology, subject to any specifically excluded limit in the stated range. Where the stated range includes one or both of the limits, ranges excluding either or both of those included limits are also included in the present technology.

In an aspect, the present disclosure provides a method of treating interstitial lung disease (ILD) in a subject in need, comprising administering to the subject a therapeutically effective amount of treprostinil, a prodrug, salt, or ester thereof.

Treprostinil is used for the treatment of pulmonary arterial hypertension. Treprostinil is a synthetic analog of prostacyclin ($PGI_2$) having the structure:

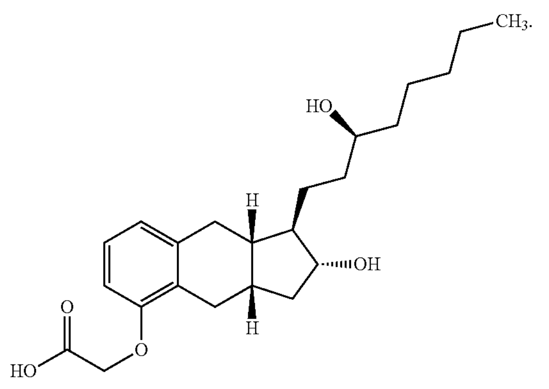 [SMILES: CCCCC[C@H](O)CC[C@@H]1[C@H]2Cc3cccc(OCC(=O)O)c3C[C@H]2C[C@H]1O]

Treprostinil, the active ingredient in Remodulin® (treprostinil) Injection, Tyvaso® (treprostinil) Inhalation Solution, and Orenitram® (treprostinil) Extended Release Tablets, was described in U.S. Pat. No. 4,306,075. Methods of making treprostinil and other prostacyclin derivatives are described, for example, in Moriarty, et al., J. Org. Chem. 2004, 69, 1890-1902, Drug of the Future, 2001, 26(4), 364-374, U.S. Pat. Nos. 6,441,245, 6,528,688, 6,700,025, 6,809,223, 6,756,117, 8,461,393, 8,481,782; 8,242,305, 8,497,393, 8,940,930, 9,029,607, 9,156,786 and 9,388,154 9,346,738; U.S. Published Patent Applications Nos. 2012-0197041, 2013-0331593, 2014-0024856, 2015-0299091, 2015-0376106, 2016-0107973, 2015-0315114, 2016-0152548, and 2016-0175319; PCT Publications No. WO2016/0055819 and WO2016/081658.

Various uses and/or various forms of treprostinil are disclosed, for example, in U.S. Pat. Nos. 5,153,222, 5,234, 953, 6,521,212, 6,756,033, 6,803,386, 7,199,157, 6,054,486, 7,417,070, 7,384,978, 7,879,909, 8,563,614, 8,252,839, 8,536,363, 8,410,169, 8,232,316, 8,609,728, 8,350,079, 8,349,892, 7,999,007, 8,658,694, 8,653,137, 9,029,607, 8,765,813, 9,050,311, 9,199,908, 9,278,901, 8,747,897, 9,358,240, 9,339,507, 9,255,064, 9,278,902, 9,278,903, 9,758,465; 9,422,223; 9,878,972; 9,624,156; U.S. Published Patent Applications Nos. 2009-0036465, 2008-0200449, 2008-0280986, 2009-0124697, 2014-0275616, 2014-0275262, 2013-0184295, 2014-0323567, 2016-0030371, 2016-0051505, 2016-0030355, 2016-0143868, 2015-0328232, 2015-0148414, 2016-0045470, 2016-0129087, 2017-0095432; 2018-0153847 and PCT Publications Nos. WO00/57701, WO20160105538, WO2016038532, WO2018/058124.

A "prodrug" of treprostinil may refer to compounds which are converted in vivo to treprostinil or its pharmaceutically active derivatives thereof, or to a compound described in PCT publication No. WO2005/007081; U.S. Pat. Nos. 7,384,978, 7,417,070, 7,544,713, 8,252,839, 8,410,169, 8,536,363, 9,050,311, 9,199,908, 9,278,901, 9,422,223; 9,624,156, 9,878,972, 9,371,264, 9,394,227, 9,505,737, 9,758,465, 9,643,911, 9,701,616, 9,776,982, 9,845,305, 9,957,200, 10,494,327, 10,053,414, 10,246,403, 10,344,012, 10,450,290, 10,464,877, 10,464,878, 10,703,706, 10,752,733, 9,255,064, 9,469,600, 10,010,518, 10,343,979, 10,526,274; U.S. Patent Application Publications Nos. 2018-0153847 and 2021-0054009; U.S. provisional patent application No. 63/036,561 filed Jun. 9, 2020; U.S. provisional patent application No. 63/125,145 filed Dec. 14, 2020, each of which is incorporated herein by reference in their entirety.

Prostacyclin is a small molecule that has been previously shown to cause dilation of large blood vessels, relaxation of smooth muscle, inhibition of smooth muscle proliferation, as well as inhibition of platelet aggregation, which is involved in the blood clotting process. Similar actions by treprostinil at the microvascular level and on capillaries near the skin are believed to help enhance cutaneous blood flow and heal and/or prevent ischemia lesions or ulcers associated with scleroderma, Buerger's disease, Raynaud's disease, Raynaud's phenomenon, and other conditions.

An "ester" of treprostinil may refer to a compound of formula:

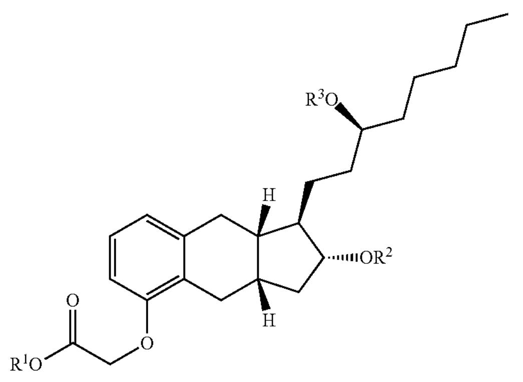

wherein $R^1$ is H, optionally substituted $C_1$-$C_{10}$ alkyl, optionally substituted $C_3$-$C_{10}$ cycloalkyl, optionally substituted $C_2$-$C_{10}$ alkenyl, optionally substituted $C_2$-$C_{10}$ alkynyl, optionally substituted aryl, optionally substituted heteroaryl, or optionally substituted heterocyclyl;

$R^2$ and $R^3$ are each independently —C(O)$R^4$; and each $R^4$ is independently optionally substituted $C_1$-$C_{10}$ alkyl, optionally substituted $C_3$-$C_{10}$ cycloalkyl, optionally substituted $C_2$-$C_{10}$ alkenyl, optionally substituted $C_2$-$C_{10}$ alkynyl, optionally substituted aryl, optionally substituted heteroaryl, or optionally substituted heterocyclyl;

wherein at least one of $R^1$, $R^2$, and $R^3$, is not H.

"Optionally substituted" refers to a group selected from that group and a substituted form of that group. Substituents may include any of the groups defined below. In one embodiment, substituents are selected from $C_1$-$C_{10}$ or $C_1$-$C_6$ alkyl, substituted $C_1$-$C_{10}$ or $C_1$-$C_6$ alkyl, $C_2$-$C_6$ alkenyl, $C_2$-$C_6$ alkynyl, $C_6$-$C_{10}$ aryl, $C_3$-$C_8$ cycloalkyl, $C_2$-$C_{10}$ heterocyclyl, $C_1$-$C_{10}$ heteroaryl, substituted $C_2$-$C_6$ alkenyl, substituted $C_2$-$C_6$ alkynyl, substituted $C_6$-$C_{10}$ aryl, substituted $C_3$-$C_8$ cycloalkyl, substituted $C_2$-$C_{10}$ heterocyclyl, substituted $C_1$-$C_{10}$ heteroaryl, halo, nitro, cyano, —$CO_2H$ or a $C_1$-$C_6$ alkyl ester thereof.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl ($(CH_3)_2CH$—), n-butyl ($CH_3CH_2CH_2CH_2$—), isobutyl ($(CH_3)_2CHCH_2$—), sec-butyl ($(CH_3)(CH_3CH_2)CH$—), t-butyl ($(CH_3)_3C$—), n-pentyl ($CH_3CH_2CH_2CH_2CH_2$), and neopentyl ($(CH_3)_3CCH_2$—).

"Alkenyl" refers to monovalent straight or branched hydrocarbyl groups having from 2 to 10 carbon atoms and preferably 2 to 6 carbon atoms or preferably 2 to 4 carbon atoms and having at least 1 and preferably from 1 to 2 sites of vinyl (>C═C<) unsaturation. Such groups are exemplified, for example, by vinyl, allyl, and but 3-en-1-yl. Included within this term are the cis and trans isomers or mixtures of these isomers.

"Alkynyl" refers to straight or branched monovalent hydrocarbyl groups having from 2 to 10 carbon atoms and preferably 2 to 6 carbon atoms or preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—$CH_2$C≡CH).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxyl, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein and with the proviso that any hydroxyl or thiol substitution is not attached to a vinyl (unsaturated) carbon atom.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein and with the proviso that any hydroxyl or thiol substitution is not attached to an acetylenic carbon atom.

"Alkoxy" refers to the group O alkyl wherein alkyl is defined herein. Alkoxy includes, by way of example, methoxy, ethoxy, n propoxy, isopropoxy, n butoxy, t butoxy, sec butoxy, and n pentoxy.

"Substituted alkoxy" refers to the group O (substituted alkyl) wherein substituted alkyl is defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Acyl includes the "acetyl" group $CH_3C(O)$—.

"Acylamino" refers to the groups —$NR^{47}$C(O)alkyl, —$NR^{47}$C(O)substituted alkyl, —$NR^{47}$C(O)cycloalkyl, —$NR^{47}$C(O)substituted cycloalkyl, —$NR^{47}$C(O)cycloalkenyl, —$NR^{47}$C(O)substituted cycloalkenyl, —$NR^{47}$C(O) alkenyl, —$NR^{47}$C(O)substituted alkenyl, —$NR^{47}$C(O)alkynyl, —$NR^{47}$C(O)substituted alkynyl, —$NR^{47}$C(O)aryl, —$NR^{47}$C(O)substituted aryl, —$NR^{47}$C(O)heteroaryl, —$NR^{47}$C(O)substituted heteroaryl, —$NR^{47}$C(O)heterocyclic, and $NR^{47}$C(O)substituted heterocyclic wherein $R^{47}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O) O—, aryl-C(O)O—, substituted aryl-C(O)O—, cycloalkyl-C(O)O—, substituted cycloalkyl-C(O)O—, cycloalkenyl-C (O)O—, substituted cycloalkenyl-C(O)O—, heteroaryl-C (O)O—, substituted heteroaryl —C(O)O, heterocyclic-C(O) O—, and substituted heterocyclic-C(O)O— wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group $NH_2$.

"Substituted amino" refers to the group —$NR^{48}R^{49}$ where $R^{48}$ and $R^{49}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, $SO_2$ alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-cycloalkenyl, —$SO_2$-substituted cylcoalkenyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic and wherein $R^{48}$ and $R^{49}$ are optionally joined, together with the nitrogen bound thereto to form a heterocyclic or substituted heterocyclic group, provided that $R^{48}$ and $R^{49}$ are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When $R^{48}$ is hydrogen and $R^{49}$ is alkyl, the substituted amino group is sometimes referred to herein as alkylamino. When $R^{48}$ and $R^{49}$ are alkyl, the substituted amino group is sometimes referred to herein as dialkylamino. When referring to a monosubstituted amino, it is meant that either $R^{48}$ or $R^{49}$ is hydrogen but not both. When referring to a disubstituted amino, it is meant that neither $R^{48}$ nor $R^{49}$ are hydrogen.

"Pharmaceutically acceptable salt" may refer to physiologically acceptable salts of treprostinil, as well as non-physiologically acceptable salts of treprostinil. Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p toluenesulfonic acid) or acidic amino acids (such as aspartic acid and glutamic acid). When the compound of the present technology (treprostinil, an ester, prodrug, or derivative thereof) has an acidic group, such as for example, a carboxylic acid group, it can form salts with metals, such as alkali and earth alkali metals (e.g., $Na^+$, $Li^+$, $K^+$, $Ca^{2+}$, $Mg^{2+}$, $Zn^{2+}$), ammonia or organic amines (e.g., dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

ILD may include a range of diseases and disorders, for example, idiopathic pulmonary fibrosis (IPF), desquamative interstitial pneumonia (DIP), acute interstitial pneumonia (AIP), nonspecific interstitial pneumonia (NSIP), respiratory bronchiolitis-associated interstitial lung disease (RB-ILD), cryptogenic organizing pneumonia (COP), lymphoid interstitial pneumonia (LIP), sarcoidosis, rheumatoid arthritis, systemic lupus erythematosus, systemic sclerosis, polymyositis, dermatomyositis, antisynthetase syndrome, silicosis, asbestosis, occupational lung disease, chronic hypersensitivity pneumonitis, idiopathic interstitial pneumonia (IIP), an autoimmune ILD, lymphangioleiomyomatosis (LAM), Langerhans cell histiocytosis (LCH), drug associated ILD, vasculitis, granulomatosis, and berylliosis.

"Pulmonary function" as used herein, refers to the ability of the lungs to absorb oxygen and expand and contract. Pulmonary function, decline thereof, or reduction of the decline, may be assessed using medically recognized tools known to those having ordinary skill in the art. Methods include pulmonary function testing (PFT), spirometry, lung volumes, maximal respiratory pressure, diffusing capacity, oxygen desaturation, and arterial blood gas evaluation.

"Forced vital capacity" as used herein, refers to the amount of air that can be forcibly exhaled from the lungs after taking the deepest breath possible, as measured by spirometry.

Further aspects of the present invention are concerned with the use of treprostinil or its derivatives, prodrugs, esters, or pharmaceutically acceptable salts thereof, in the manufacture of a medicament for the treatment or prevention of interstitial lung disease or a condition associated with interstitial lung disease. In some embodiments, the medicament is formulated for inhalation. When administered by inhalation, the formulation can be nebulized or formulated for a dry powder inhaler (DPI).

The amount of treprostinil or its derivative, or a pharmaceutically acceptable salt thereof, that is required in methods may depend on a number of factors, such as the specific indication it is being used for, the nature of the particular compound used, the mode of administration, the concentration, and the weight and condition of the subject. A daily dose per subject for ILD, or conditions associated with ILD may be in the range 25 μg to 250 mg or 7 μg to 285 μg, per day per kilogram bodyweight. In some embodiments, the daily dose may be in the range of about 150 μg to about 350 μg per day, about 200 μg to about 300 μg per day, or about 225 μg to about 275 μg per day. Intravenous doses in the range 0.5 μg to 1.5 mg per kilogram bodyweight per day may be administered as an infusion of from 0.5 ng to 1.0 μg per kilogram bodyweight per minute.

The treprostinil or its derivative, prodrug, ester, or a pharmaceutically acceptable salt thereof, can be administered using any suitable treatment schedule. In some embodiments, the drug will be administered multiple times a day (1, 2, 3, 4, or 5), and in other embodiments, the drug can be continuously administered, such as by using an infusion pump. The duration of treatment can vary depending on the severity of disease, treatment goals, or individual circumstances. In some embodiments, the duration of treatment is at least one week, at least two weeks, at least four weeks, at least eight weeks, or at least sixteen weeks. In some embodiments, the duration of treatment is indefinite, e.g., treatment can continue for the life of the subject or until disease symptoms decrease below some threshold.

Pharmaceutical compositions described herein or administered to subjects, hereinafter referred to as a "formulation" or "composition," of treprostinil and/or its prodrugs, esters, derivatives, and/or pharmaceutically acceptable salts thereof, may be admixed with, inter alia, an acceptable carrier. The carrier may be compatible with any other ingredients in the formulation and not deleterious to the subject. The carrier may be a solid or a liquid, or both. One or more of treprostinil or its derivatives, esters, prodrugs, or pharmaceutically acceptable salts thereof, may be incorporated in the formulations of the invention. Formulations administered include those suitable for parenteral, oral, inhalation, rectal, topical, buccal and transdermal administration.

Parenterally administered compositions may be isotonic with the blood of the intended recipient. Subcutaneous injection, intravenous, intramuscular or intradermal injection may be used. Such preparations may conveniently be prepared by admixing the compound with water or a glycine or citrate buffer and rendering the resulting solution sterile and isotonic with the blood.

Formulations suitable for oral administration may be presented as capsules, cachets, lozenges, or tablets, each containing a specific amount of treprostinil or its derivative, prodrug, ester, or a pharmaceutically acceptable salt thereof; as a powder or granules; as a solution or a suspension in an aqueous or non-aqueous liquid; or as an oil-in-water or water-in-oil emulsion. Oral formulations that may be administered include those described in U.S. Pat. Nos. 7,384,978 and 8,747,897 (including the commercial product Orenitram® (treprostinil) Extended-Release Tablets), the entire disclosures of which are hereby incorporated by reference. In general, the formulations of the invention are prepared by uniformly and intimately admixing treprostinil, an ester, prodrug, or salt thereof with a liquid or finely divided solid carrier, or both, and then, if necessary, shaping the resulting mixture.

Formulations suitable for buccal (sub-lingual) administration include lozenges comprising treprostinil or its derivative, prodrug, ester, or a pharmaceutically acceptable salt thereof, in a flavored base, usually sucrose and acacia or tragacanth; and pastilles comprising the compound in an inert base such as gelatin and glycerin or sucrose and acacia.

Formulations suitable for rectal administration are preferably presented as unit dose suppositories. These may be prepared by admixing treprostinil or its derivative, prodrug, ester, or a pharmaceutically acceptable salt thereof, with one or more solid carriers.

Topical and transdermal formulations me be an ointment, cream, lotion, paste, gel, spray, aerosol, or oil. Carriers possible include vaseline, lanoline, polyethylene glycols, alcohols, and combinations thereof.

Treprostinil, prodrugs, esters, and salts thereof are conveniently prepared by methods the same as or analogous to those described in U.S. Pat. Nos. 4,306,075, 6,528,688 and 6,441,245, the disclosures of which are hereby incorporated by reference.

In some embodiments of the present methods, the treprostinil administered is provided as a kit with instructions for use in treating ILD. In certain kit embodiments, the treprostinil or its derivative, prodrug, ester, or a pharmaceutically acceptable salt thereof, is in a form suitable for subcutaneous administration, continuous subcutaneous infusion, intravenously administration or inhalation. Subcutaneous formulations administered to the subject may include any of those described in U.S. Pat. No. 7,999,007 (including the commercial product Remodulin® (treprostinil) Injection), the entire disclosure of which is hereby incorporated by reference. In other kit embodiments, the treprostinil or its derivative, or a pharmaceutically acceptable salt thereof, is in an orally available form selected from the group consisting of tablets and capsules.

The effects of the method on pulmonary fibroses (PF) can be ascertained via an animal model of PF such as bleomycin and vanadium pentoxide ($V_2O_5$) models as described in Bonner J C, Rice A B, Ingram J L, Moomaw C R, Nyska A, Bradbury A, Sessoms A R, Chulada P C, Morgan D L, Zeldin D C, and Langenbach R. Susceptibility of cyclooxygenase-2-deficient mice to pulmonary fibrogenesis. *Am J Pathol* 161: 459-470, 2002; 23; and Keerthisingam C B, Jenkins R G, Harrison N K, Hernandez-Rodriguez N A, Booth H, Laurent G J, Hart S L, Foster M L, and McAnulty R J. Cyclooxygenase-2 deficiency results in a loss of the anti-proliferative response to transforming growth 31 factor-beta in human fibrotic lung fibroblasts and promotes bleomycin-induced pulmonary fibrosis in mice. *Am J Pathol* 158: 1411-1422, 2001, incorporated herein by reference in their entirety.

In preferred embodiments, treprostinil is administered via inhalation. Inhaled compositions comprising treprostinil may include sprays, aerosols, and dry powder compositions. Said compositions may include a variety of excipients.

Inhalable compositions administered may include any of those described in U.S. Pat. No. 9,339,507 (including the commercial product Tyvaso® (treprostinil) Inhalation Solution), WO2017192993 and WO2014085813, the entire disclosures of which are hereby incorporated by reference.

The excipient or excipients of the pharmaceutical composition according to the invention may have water solubility greater than 5 g/l and often greater than 100 g/l and more. They are preferably chosen among sugars, salts or amino acids and have double function of minimizing the effect of the inhaled composition on the fluid's cellular outcome. Regarding the composition in its solid dry form, the excipient also forms the solid matrix in which the treprostinil, a prodrug, ester, salt, or derivative thereof is dispersed.

The composition may include excipients such as lactose, corn starch, or the like, glidants such as magnesium stearate, etc., emulsifying agents, suspending agents, stabilizers, and isotonic agents, etc. If desired, a sweetening agent and/or a flavoring agent may be added. Exemplary excipients include, without limitation, polyethylene glycol (PEG), hydrogenated castor oil (HCO), cremophors, carbohydrates, starches (e.g., corn starch), inorganic salts, antimicrobial agents, antioxidants, binders/fillers, surfactants, lubricants (e.g., calcium or magnesium stearate), glidants such as talc, disintegrants, diluents, buffers, acids, bases, film coats, combinations thereof, and the like. Other examples of soluble excipients that may be used in the composition according to the invention are alitame, acesulfame potassium, aspartame, saccharin, sodium saccharin, sodium cyclamate, sucralose, threalose, xylitol, citric acid, tartaric acid, cyclodextrins, dextrins, hydroxyethylcellulose, gelatine, malic acid, maltitol, maltodextrin, maltose, polydextrose, tartaric acid, sodium or potassium bicarbonate, sodium or potassium chloride, sodium or potassium citrate, phospholipids, lactose, sucrose, glucose, fructose, mannitol, sorbitol, natural aminoacids, alanine, glycine, serine, cysteine, phenylalanine, tyrosine, tryptophan, histidine, methionine, threonine, valine, isoleucine, leucine, arginine, lysine, aspartic acid, glutamic acid, asparagine, glutamine, proline, their salts, and their possible simple chemical modifications such as in N-acetylcysteine, and carbocysteine.

The preferred soluble excipients are alkaline metals salts such as sodium chloride or potassium chloride, and sugars, such as lactose. Specific carbohydrate excipients include, for example, monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

As far as the hollow morphology of the particles of the dry powder is concerned, the composition requires the presence of a soluble excipient, preferably a sugar like lactose, able to form in the beginning of the solvent evaporation phase during preparation of the composition, during spray-drying, the backbone of the particle, producing high porosity particles.

In some embodiments, the excipient comprises a surfactant. The surfactant of the composition can be chosen among different classes of surfactants of pharmaceutical use.

Surfactants suitable to be used in the present invention are all those substances characterized by medium or low molecular weight that contain a hydrophobic moiety, generally readily soluble in an organic solvent but weakly soluble or insoluble in water, and a hydrophilic (or polar) moiety, weakly soluble or insoluble in an organic solvent but readily soluble in water. Surfactants are classified according to their polar moiety. Therefore, surfactant with a negatively charged polar moiety are called anionic surfactants, while cationic surfactants have a positively charged polar moiety. Uncharged surfactant are generally called non-ionic, while surfactant charged both positively and negatively are called zwitterionic. Examples of anionic surfactants are salts of fatty acids (better known as soaps), sulfates, sulfate ethers and phosphate esters. Cationic surfactants are frequently based on polar groups containing amino groups. Most common non-ionic surfactants are based on polar groups containing oligo-(ethylene-oxide) groups. Zwitterionic surfactants are generally characterized by a polar group formed by a quaternary amine and a sulfuric or carboxylic group.

Specific examples of this application are the following surfactants: benzalkonium chloride, cetrimide, docusate sodium, glyceryl monolaurate, sorbitan esters, sodium lauryl sulfate, polysorbates, phospholipids, biliary salts.

Non-ionic surfactants, such as polysorbates and polyethylene and polyoxypropylene block copolymers, known as "Poloxamers," may be used. Polysorbates are described in the CTFA International Cosmetic Ingredient Dictionary as mixtures of sorbitol and sorbitol anhydride fatty acid esters condensed with ethylene oxide. Particularly preferred are non-ionic surfactants of the series known as "Tween," in particular the surfactant known as "Tween 80," a polyoxyethylensorbitan. Additional exemplary excipients include surfactants such as other polysorbates, e.g., "Tween 20" and pluronics such as F68 and F88 (both of which are available from BASF, Mount Olive, N.J.), sorbitan esters, lipids (e.g., phospholipids such as lecithin and other phosphatidylcholines, and phosphatidylethanolamines), fatty acids and fatty esters, steroids such as cholesterol, and chelating agents, such as EDTA, zinc and other such suitable cations.

The presence of a surfactant, and preferably of Tween 80, may be necessary to reduce electrostatic charges found in compositions without it, the flow of the powder and the maintenance of the solid state in a homogeneous way without initial crystallization. According to the present invention, phospholipids are included in the above-mentioned definition of surfactants or excipients.

The inhalatory formulation according administered can include a hydrophobic substance in order to reduce sensitivity to humidity. Such hydrophobic substance is preferably leucine, which makes the particle disaggregation easier.

In case of production of a solid product in powder form, this can occur using different techniques, well consolidated in the pharmaceutical industry. The preparation of fine particles through spray-drying represents a preferred method according to the invention. In case of industrial production, this technique is undoubtedly preferred to freeze-drying, which at the moment is the most expensive drying process, both for the apparatus used, and for the yield and production times.

The pharmaceutical composition according to the invention can include other components, such as pH buffers and preservatives. Buffers include, but are not limited to, citric acid, sodium chloride, potassium chloride, sodium sulfate, potassium nitrate, sodium phosphate monobasic, sodium phosphate dibasic, and combinations thereof.

Further, a composition administered may optionally include one or more acids or bases. Non-limiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof.

Non-limiting examples of suitable bases include bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The excipients may include an antioxidant, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

The term "dry powder" in reference to the composition of the invention, refers to a powder, granulate, tablet form composition, or any other solid form with a humidity content that assures to the composition chemical stability in time. More precisely, the term "dry" refers to a solid composition with water content lower than 10% w/w, normally less than 5% and preferably less than 3%.

The amount of any excipient in the dry powder composition of the invention can change within a wide range. The amount of any individual excipient in the composition will vary depending on the role of the excipient, the dosage requirements of the active agent components, and particular needs of the composition. Generally, however, the excipient will be present in the composition in an amount of about 1% to about 99% by weight, preferably from about 5% to about 98% by weight, more preferably from about 15% to about 95% by weight of the excipient. In general, the amount of excipient present in a composition of the disclosure is selected from the following: at least about 2%, 5%, 10%, 15%, 20%, 25%, 30%, 35%, 40%, 45%, 50%, 55%, 60%, 65%, 70%, 75%, 80%, 85%, 90%, or even 95% by weight.

The treprostinil composition administered may be provided as a kit that includes a metered dose inhaler containing a pharmaceutical composition comprising treprostinil or its derivative, ester, prodrug, or a pharmaceutically acceptable salt thereof. Such a kit can further include instructions on how to use the metered dose inhaler for inhaling treprostinil. Such instructions can include, for example, information on how to coordinate patient's breathing, and actuation of the inhaler. The kit can be used by a subject, such as human being, affected with ILD that can be treated by treprostinil. In some cases, the kit is a kit for treating ILD, that includes (i) a metered dose inhaler containing a pharmaceutical composition comprising treprostinil or its derivative, ester, prodrug, or a pharmaceutically acceptable salt thereof, and (ii) instructions for use of the metered dose inhaler containing treprostinil in treating pulmonary hypertension.

The present disclosure also provides a method of treating a pulmonary hypertension due to a condition selected from a chronic lung disease and/or hypoxia (low oxygen levels) by administering to a subject, such as a human being, with such the pulmonary hypertension an effective amount of treprostinil, its prodrug, its pharmaceutically acceptable salt or a pharmaceutically acceptable salt of its prodrug. Pulmonary hypertension due to a chronic lung disease and/or hypoxia belongs Group 3 pulmonary hypertension according to the World Health Organization (WHO) classification.

The chronic lung disease may include an obstructive lung disease in which the lung airways are narrow and make it difficult to exhale, such as chronic obstructive pulmonary disease (COPD) and emphysema; a restrictive lung disease in which the lungs have a difficult time expanding when one inhales, such as interstitial lung disease or pulmonary fibrosis; sleep apnea; living in an area of high altitude for a long period of time; and various combinations of the above conditions.

In some embodiments, the chronic lung disease may include idiopathic interstitial pneumonia, such as idiopathic pulmonary fibrosis, idiopathic nonspecific interstitial pneumonia, respiratory bronchiolitis (e.g. respiratory bronchiolitis associated with interstitial lung disease), desquamative interstitial pneumonia, acute interstitial pneumonia; chronic hypersensitivity pneumonitis, occupational lung disease, pulmonary fibrosis, emphysema, connective tissue disease or any combination of the above conditions.

In some embodiments, administering the effective amount of treprostinil, its prodrug, its pharmaceutically acceptable salt or a pharmaceutically acceptable salt of its prodrug may provide an increase, which may be statistically significant, in a six minute walk distance (6MWD) in a subject with a pulmonary hypertension due to a condition selected from a chronic lung disease and/or hypoxia compared to a baseline 6MWD value, i.e. a 6MWD value prior to the administering. For example, the 6MWD value may be statistically significantly increased after at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks or at least 16 weeks or at least 20 weeks or at least 24 weeks or at least 28 weeks or at least 32 weeks or at least 36 weeks or at least 40 weeks or at least 44 weeks or at least 48 weeks or at least 52 weeks of the administering. In some embodiments, the administering may provide an increase of at least 5 m, at least 10 m or at least 15 m in the 6MWD compared to the baseline 6MWD value after at least 8 weeks, at least 9 weeks, at least 10 weeks, at least 11 weeks, at least 12 weeks, at least 13 weeks, at least 14 weeks, at least 15 weeks or at least 16 weeks or at least 20 weeks or at least 24 weeks or at least 28 weeks or at least 32 weeks or at least 36 weeks or at least 40 weeks or at least 44 weeks or at least 48 weeks or at least 52 weeks of the administering. In some embodiments, the administering may provide an increase of at least 5 m, at least 10 m, at least 15 m, at least 18 m or at least 20 m in the 6MWD compared to the baseline 6MWD value after at least 12 weeks, at least 13 weeks, at least 14 weeks, at least 15 weeks or at least 16 weeks of the administering.

In some embodiments, administering the effective amount of treprostinil, its prodrug, its pharmaceutically acceptable salt or a pharmaceutically acceptable salt of its prodrug may provide an reduction, which may be statistically significant, in a plasma concentration of NT-proBNP in a subject with a pulmonary hypertension due to a condition selected from a chronic lung disease and/or hypoxia compared to a baseline NT-proBNP plasma concentration, i.e. a NT-proBNP plasma concentration value prior to the administering. For example, the NT-proBNP plasma concentration may be statistically significantly reduced after at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks or at least 16 weeks or at least 20 weeks or at least 24 weeks or at least 28 weeks or at least 32 weeks or at least 36 weeks or at least 40 weeks or at least 44 weeks or at least 48 weeks or at least 52 weeks of the administering. In some embodiments, the administering may provide a reduction of at least 50 pg/ml, at least 100 pg/ml, at least 150 pg/ml, at least 200 pg/ml, at least 250 pg/ml, at least 300 pg/ml or at least 350 pg/ml in the NT-proBNP plasma concentration compared to the baseline the NT-proBNP plasma concentration value after at least 8 weeks, at least 9 weeks, at least 10 weeks, at least 11 weeks, at least 12 weeks, at least 13 weeks, at least 14 weeks, at least 15 weeks or at least 16 weeks of the administering.

In some embodiments, administering the effective amount of treprostinil, its prodrug, its pharmaceutically acceptable salt or a pharmaceutically acceptable salt of its prodrug to a subject with a pulmonary hypertension due to a chronic lung disease may provide a reduction, which may be statistically significant, of a number of exacerbation(s) of the chronic lung disease. For example, a number of exacerbation(s) of the chronic lung disease may be lower in a patient subpopulation with the pulmonary hypertension due to the chronic lung disease, who was administered the effective amount of treprostinil, its prodrug, its pharmaceutically acceptable salt or a pharmaceutically acceptable salt of its prodrug for at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks or at least 16 weeks or at least 20 weeks or at least 24 weeks or at least 28 weeks or at least 32 weeks or at least 36 weeks or at least 40 weeks or at least 44 weeks or at least 48 weeks or at least 52 weeks, compared to a patient subpopulation with the same condition, which was administered a placebo instead of treprostinil. For example, the number of exacerbation(s) may be lowered by at least 10%, at least 20%, at least 30%, at least 40%, at least 50%, at least 60%, at least 70% or at least 80%. The exacerbation(s) may include an acute, clinically significant, respiratory deterioration characterized by evidence of new widespread alveolar abnormality.

In some embodiments, administering the effective amount of treprostinil, its prodrug, its pharmaceutically acceptable salt or a pharmaceutically acceptable salt of its prodrug to a subject with a pulmonary hypertension due to a chronic lung disease and/or hypoxia may provide a reduction, which may be statistically significant, of a number of clinical worsening event(s). For example, a number of clinical worsening event(s) may be lower in a patient subpopulation with the pulmonary hypertension due to the chronic lung disease and/or hypoxia, who was administered the effective amount of treprostinil, its prodrug, its pharmaceutically acceptable salt or a pharmaceutically acceptable salt of its prodrug for at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks or at least 16 weeks or at least 20 weeks or at least 24 weeks or at least 28 weeks or at least 32 weeks or at least 36 weeks or at least 40 weeks or at least 44 weeks or at least 48 weeks or at least 52 weeks compared to a patient subpopulation with the same condition, which was administered a placebo instead of treprostinil. For example, the number of clinical worsening event(s) may be lowered by at least 10%, at least 20%, at least 30%, at least 40%, at least 50%, at least 60%, at least 70% or at least 80%. The clinical worsening event(s) may include one or more of hospitalization due to a cardiopulmonary indication, a decrease in a 6MWD by more than 15% from a baseline 6MWD value, death or a lung transplantation.

In some embodiments, administering the effective amount of treprostinil, its prodrug, its pharmaceutically acceptable salt or a pharmaceutically acceptable salt of its prodrug may provide an improvement, which may be statistically significant, in forced vital capacity (FVC) in a subject with a pulmonary hypertension due to a condition selected from a chronic lung disease and/or hypoxia. For example, the FVC may be higher in a patient subpopulation with the pulmonary hypertension due to the chronic lung disease and/or hypoxia, who was administered the effective amount of treprostinil, its prodrug, its pharmaceutically acceptable salt or a pharmaceutically acceptable salt of its prodrug for at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks or at least 16 weeks, or at least 20 weeks or at least 24 weeks or at least 28 weeks or at least 32 weeks or at least 36 weeks or at least 40 weeks or at least 44 weeks or at least 48 weeks or at least 52 weeks, compared to a patient subpopulation with the same condition, which was administered a placebo instead of treprostinil. For example, the FVC value may be higher by at least 10 ml or at least 15 ml or at least 20 ml or at least 25 ml or at least 30 ml or at least 35 ml or at least 40 ml or at least 45 ml after at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks or at least 16 weeks of the administering in the patient subpopulation with the pulmonary hypertension due to the chronic lung disease and/or hypoxia, who was administered the effective amount of treprostinil, its prodrug, its pharmaceutically acceptable salt or a pharmaceutically acceptable salt of its prodrug compared to the patient subpopulation with the same condition, which was administered a placebo instead of treprostinil. In patients with a chronic lung disease, such as interstitial lung disease, and/or hypoxia, an FVC value usually decreases with time when untreated. Thus, administering the effective amount of treprostinil, its prodrug, its pharmaceutically acceptable salt or a pharmaceutically acceptable salt may increase an FVC value compared to an FVC value before the administering; maintain an FVC value within 5%, 10% or 20% within the FVC value prior to the administering; or reduce a decrease of an FVC value with time compared to a decrease in an FVC value with no administering the effective amount of treprostinil, its prodrug, its pharmaceutically acceptable salt or a pharmaceutically acceptable salt, such a decrease in an FVC value when placebo is administered instead of treprostinil, its prodrug, its pharmaceutically acceptable salt or a pharmaceutically acceptable salt.

In some embodiments, treprostinil, its prodrug, its pharmaceutically acceptable salt or a pharmaceutically acceptable salt of its prodrug may be administered by inhalation, which may be, for example, an oral inhalation or a nasal inhalation. In some embodiments, treprostinil, its prodrug, its pharmaceutically acceptable salt or a pharmaceutically acceptable salt of its prodrug may be administered by an inhalation device, which may be for example, a pulsed inhalation device, such as a metered dose inhaler and/or a pulsed nebulizer. Pulsed inhalation devices are disclosed, for example, in U.S. patent application publication No. 20080200449, U.S. Pat. Nos. 9,358,240; 9,339,507; 10,376,525; and 10,716,793, each of which is incorporated herein by reference in its entirety.

In some embodiments, the inhalation device, such as a pulsed inhalation device, may contain a solution or a suspension comprising treprostinil, its prodrug, its pharmaceutically acceptable salt or a pharmaceutically acceptable salt of its prodrug. For example, such solution or suspension may be used for aerosolizing or a nebulizing by an inhalation device, such as a nebulizer and/or a metered dose inhaler. One example of a solution may be a commercial product Tyvaso®. A concentration of treprostinil in such solution may vary. In some embodiments, the treprostinil concentration may be from 200 μg/ml to 2000 μg/ml or from 300 μg/ml to 1500 μg/ml or from 400 μg/ml to 1200 μg/ml or any value or subrange within these ranges. For example, in a certain embodiment, the treprostinil concentration may be 600 μg/ml.

In some embodiments, the inhalation device, such as a pulsed inhalation device, may be a dry powder inhaler, which may contain a dry powder composition or formulation comprising treprostinil, its prodrug, its pharmaceutically acceptable salt or a pharmaceutically acceptable salt of its prodrug. For example, a dry powder inhaler and a dry powder composition or formulation comprising treprostinil are disclosed in WO2019/237028, which incorporated herein by reference in its entirety. In some embodiments, in addition to treprostinil, its prodrug, its pharmaceutically acceptable salt or a pharmaceutically acceptable salt of its prodrug, the dry powder composition may further a diketopiperazine, such as (E)-3,6-bis[4-(N-carbonyl-2-propenyl) amidobutyl]-2,5-diketopiperazine (FDKP).

Treprostinil, its prodrug, its pharmaceutically acceptable salt or a pharmaceutically acceptable salt of its prodrug may be administered by inhalation in a single administering event which may involve a limited number of breaths (or inhalations) by the subject. For example, in some embodiments, a number of breaths in the single administering event may not exceed 20 breaths (or inhalations) or 19 breaths (or inhalations) or 18 breaths (or inhalations) or 17 breaths (or inhalations) or 16 breaths (or inhalations) or 15 breaths (or inhalations) or 14 breaths (or inhalations) or 13 breaths (or inhalations) or 12 breaths (or inhalations) or 11 breaths (or inhalations) or 10 breaths (or inhalations) or 9 breaths (or breaths (or inhalations) inhalations) or 8 breaths (or inhalations) or 7 breaths (or inhalations) or 6 breaths (or inhalations) or 5 breaths (or inhalations) or 4 breaths (or inhalations) or 3 breaths (or inhalations) or 2 breaths (or inhalations) or 1 breath (or inhalation).

A dose of treprostinil, its prodrug, its pharmaceutically acceptable salt or a pharmaceutically acceptable salt of its prodrug administered by inhalation in a single administering event may vary. In some embodiments, the single administering event dose may be from 7.5 μg to 100 μg or 10 μg to 100 μg or 15 μg to 100 μg from 15 μg to 90 μg or from 15 μg to 75 μg or from 30 μg to 75 μg or any value or subrange within these ranges.

A number of single administering events per day for administering treprostinil, its prodrug, its pharmaceutically acceptable salt or a pharmaceutically acceptable salt of its prodrug administered by inhalation may vary. For example, the number of single administering events per day may be 1, 2, 3, 4, 5 or 6 per day.

The table below provides exemplary doses of treprostinil in a dry powder formulation, which may be used in a dry powder inhaler, and how they may compare with treprostinil doses in Tyvaso® inhalation solution.

| DPI (treprostinil) Inhalation Powder Cartridge Strength (QID) | Tyvaso (treprostinil) Inhalation Solution Number of Breaths (QID) |
|---|---|
| 16 mcg | 2 to 4 (18 to 24 mcg) |
| 32 mcg | 5 to 7 (30 to 42 mcg) |
| 48 mcg | 8 to 10 (48 to 60 mcg) |
| 64 mcg | 11 to 13 (66 to 78 mcg) |

The disclosure of all publications cited above are expressly incorporated herein by reference in their entireties to the same extent as if each were incorporated by reference individually.

The examples described herein are illustrative of the present invention and are not intended to be limitations thereon. Different embodiments of the present invention have been described according to the present invention. Many modifications and variations may be made to the techniques described and illustrated herein without departing from the spirit and scope of the invention. Accordingly, it should be understood that the examples are illustrative only and are not limiting upon the scope of the invention.

EXAMPLES

Example 1: Inhaled Treprostinil Results on Underlying Lung Disease

An exacerbation of underlying lung disease is defined as an acute, clinically significant, respiratory deterioration characterized by evidence of new widespread alveolar abnormality (Collard et al., 2016). The present example shows that treatment with inhaled treprostinil resulted in significantly fewer exacerbations of underlying lung disease in patients.

Subjects having underlying lung disease were treated with inhaled treprostinil over 16 weeks. Subjects initiated inhaled treprostinil or placebo at a dose of 3 breaths (18 mcg) 4 times daily (during waking hours). Study drug doses were maximized throughout the study. Dose escalations (additional 1 breath 4 times daily) could occur up to every 3 days with a target dosing regimen of 9 breaths (54 mcg) 4 times daily and a maximum dose of 12 breaths (72 mcg) 4 times daily, as clinically tolerated. Subjects were assessed during Screening and Baseline to determine eligibility for the study. Once eligible, 5 Treatment Phase visits to the clinic were required at Week 4, Week 8, Week 12, Week 15, and Week 16 (final study visit). An Early Termination (ET) Visit was conducted for subjects who discontinued prior to Week 16; all assessments planned for the final Week 16 Visit were conducted during the ET Visit, if applicable. Subjects were contacted at least weekly by telephone or email to assess tolerance to study drug, adverse events (AEs), and changes to concomitant medications.

Efficacy assessments consisted of 6MWD, plasma NT-proBNP concentration, and time to clinical worsening. Exploratory endpoints included SGRQ, change in DSP, time to exacerbation of underlying disease, and pulmonary function tests. Safety assessments consisted of the development of AEs, vital signs, clinical laboratory parameters, ECG parameters, hospitalizations due to cardiopulmonary indications, exacerbations of underlying lung disease, and oxygenation.

Treatment resulted in significantly fewer exacerbations of underlying lung disease over the 16-week treatment period (26.4% in Inhaled Treprostinil group and 38.7% in placebo group; p=0.018) and decreased risk of an exacerbation of underlying lung disease (hazard ratio 0.66 or 34% reduction in risk) as shown in FIG. 1.

In addition, the following FVC suggestive data was obtained from this study. Among patients treated with inhaled treprostinil, overall results from intent to treat group were:

Overall ITT 28.47 mL and 44.40 mL in FVC at Weeks 8 and 16

Percent predicted FVC at Week 8 (1.79%; p=0.0139) and Week 16 (1.80%; p=0.0277).

Subset IIP Etiology:

46.48 mL and 108.18 mL (p=0.0229) at Weeks 8 and 16

Percent predicted FVC at Week 8 (1.95%, p=0.0373) and Week 16 (2.88%; p=0.0096)

Subset IPF Etiology:

84.52 mL and 168.52 mL (p=0.0108) at Weeks 8 and 16

Percent predicted FVC at Week 8 (2.54%; p=0.0380) and Week 16 (3.50%; p=0.0147)

Nintedanib: IPF~109 mL (3.2% predicted) at 52 weeks

Pirfenidone: IPF~153-193 mL at 52 weeks

Placebo Corrected, Rate of Decline (not Improvements)

In comparison to the known treatments for ILD (nintedanib and pirfenidone) shown above, inhaled treprostinil achieves comparable effects with shorter treatment duration.

Pulmonary function testing was initially conducted as a safety assessment (Safety Population) during the study. The results indicated that although most PFT parameters remained stable for subjects in the study, a notable improvement in FVC (% predicted) was observed at Week 16 in the inhaled treprostinil group (median improvement of 1.0% compared to a 1.0% reduction in the placebo group). As a result, post hoc MMRM analyses of FVC data were performed for the ITT Population and are presented in Table 1 (ITT Population), Table 2 (by PH ILD Etiology of IP) and Table 3 (for subjects with IPF), shown below.

TABLE 1

Analysis of FVC Data Using Mixed Model Repeated Measurement - ITT Population

| Visit | Treatment | N | LS Mean | Contrast | Estimated Difference | 95% CI | p-value |
|---|---|---|---|---|---|---|---|
| | | | | FVC (mL) | | | |
| Week 8 | Inhaled treprostinil | 142 | 5.49 | Inhaled treprostinil − Placebo | 28.47 | −30.81, 87.74 | 0.3453 |
| | Placebo | 141 | −22.98 | | | | |
| Week 16 | Inhaled treprostinil | 130 | 9.77 | Inhaled treprostinil − Placebo | 44.40 | −25.25, 114.05 | 0.2106 |
| | Placebo | 126 | −34.63 | | | | |
| | | | | FVC (% predicted) | | | |
| Week 8 | Inhaled treprostinil | 142 | 0.77 | Inhaled treprostinil − Placebo | 1.79 | 0.37, 3.21 | 0.0139 |
| | Placebo | 141 | −1.02 | | | | |
| Week 16 | Inhaled treprostinil | 130 | 1.07 | Inhaled treprostinil − Placebo | 1.80 | 0.20, 3.39 | 0.0277 |
| | Placebo | 126 | −0.72 | | | | |

Abbreviations:

CI, confidence interval;

FVC, forced vital capacity;

ITT, Intent-to-Treat;

LS, least square;

MMRM, mixed model repeated measurement

LSMean, p-values, estimated difference, and associated 95% CI were from the MMRM with the change from baseline in FVC/% predicted FVC as the dependent variable; treatment, week, treatment by week interaction as the fixed effects; baseline FVC/% predicted FVC as the covariate; and subject as the random effect. An unstructured variance/covariance structure shared across treatment groups was used to model the within-subject errors.

TABLE 2

Analysis of FVC Data Using Mixed Model Repeated Measurement for PH-ILD Etiology of IIP - ITT Population

| Visit | Treatment | N | LS Mean | Contrast | Estimated Difference | 95% CI | p-value |
|---|---|---|---|---|---|---|---|
| | | | | PH-ILD Etiology: IIP FVC (mL) | | | |
| Week 8 | Inhaled treprostinil | 58 | 9.27 | Inhaled treprostinil − Placebo | 46.48 | −32.55, 125.51 | 0.2467 |
| | Placebo | 71 | −37.21 | | | | |
| Week 16 | Inhaled treprostinil | 52 | 22.16 | Inhaled treprostinil − Placebo | 108.18 | 15.25, 201.10 | 0.0229 |
| | Placebo | 63 | −86.02 | | | | |
| | | | | FVC (% predicted) | | | |
| Week 8 | Inhaled treprostinil | 58 | 0.92 | Inhaled treprostinil − Placebo | 1.95 | 0.12, 3.79 | 0.0373 |
| | Placebo | 71 | −1.03 | | | | |
| Week 16 | Inhaled treprostinil | 52 | 1.66 | Inhaled treprostinil − Placebo | 2.88 | 0.72, 5.05 | 0.0096 |
| | Placebo | 63 | −1.23 | | | | |

Abbreviations:

CI, confidence interval;

CPFE, combined pulmonary fibrosis and emphysema;

CTD, connective tissue disease;

FVC, forced vital capacity;

ILD, interstitial lung disease;

IIP, idiopathic interstitial pneumonia;

ITT, Intent-to-Treat;

LS, least square;

MMRM, mixed model repeated measurement

LSMean, p-values, estimated difference, and associated 95% CI were from the MMRM with the change from baseline in FVC/% predicted FVC as the dependent variable; treatment, week, treatment by week interaction as the fixed effects; baseline FVC/% predicted FVC as the covariate; and subject as the random effect. An unstructured variance/covariance structure shared across treatment groups was used to model the within-subject errors.

Table 3: Analysis of FVC Data Using Mixed Model Repeated Measurement for Subjects with IPF - ITT for IIP Subjects

| | | | | | | | |
|---|---|---|---|---|---|---|---|
| | | | IPF FVC (mL) | | | | |
| Week 8 | Inhaled treprostinil | 31 | 41.69 | Inhaled treprostinil − Placebo | 84.522 | −20.409, 189.454 | 0.1128 |
| | Placebo | 47 | −42.83 | | | | |
| Week 16 | Inhaled treprostinil | 28 | 38.24 | Inhaled treprostinil − Placebo | 168.524 | 40.078, 296.970 | 0.0108 |
| | Placebo | 42 | −130.3 | | | | |
| | | | FVC (% predicted) | | | | |
| Week 8 | Inhaled treprostinil | 31 | 1.60 | Inhaled treprostinil − Placebo | 2.543 | 0.145, 4.941 | 0.0380 |
| | Placebo | 47 | −0.94 | | | | |
| Week 16 | Inhaled treprostinil | 28 | 1.62 | Inhaled treprostinil − Placebo | 3.504 | 0.712, 6.295 | 0.0147 |
| | Placebo | 42 | −1.88 | | | | |

Abbreviations:
CI, confidence interval;
FVC, forced vital capacity;
IPF, idiopathic pulmonary fibrosis;
ITT, Intent-to-Treat;
LS, least square; MMRM, mixed model repeated measurement
LSMean, p-values, estimated difference, and associated 95% CI were from the MMRM with the change from baseline in FVC/% predicted FVC as the dependent variable; treatment, week, treatment by week interaction as the fixed effects; baseline FVC/% predicted FVC as the covariate; and subject as the random effect. An unstructured variance/covariance structure shared across treatment groups was used to model the within-subject errors.

Treatment with inhaled treprostinil resulted in improvements of 28.47 mL and 44.40 mL in FVC at Weeks 8 and 16, respectively; significant when presented as % predicted FVC at Week 8 (1.79%; p=0.0139) and Week 16 (1.80%; p=0.0277).

When FVC was analyzed by PH-ILD etiology of IIP, treatment with inhaled treprostinil resulted in improvements of 46.48 mL and 108.18 mL (p=0.0229) when compared to placebo at Weeks 8 and 16, respectively. The between group differences for % predicted FVC were statistically significant at Week 8 (1.95%, p=0.0373) and Week 16 (2.88%; p=0.0096).

Further analysis of FVC for subjects with an IPF etiology (using only the IIP subjects in the ITT Population), showed that treatment with inhaled treprostinil resulted in improvements of 84.52 mL and 168.52 mL (p=0.0108) compared to placebo at Weeks 8 and 16, respectively. The between group differences for % predicted FVC were statistically significant at Week 8 (2.54%; p=0.0380) and Week 16 (3.50%; p=0.0147).

Example 2

The following prophetic example will assess efficacy of treprostinil as indicated for the treatment of chronic fibrosing interstitial lung diseases (CF-ILDs) including Idiopathic Interstitial Pneumonias (IIPs) including IPF, chronic hypersensitivity pneumonitis (CHP), and environmental/occupational fibrosing lung disease.

Patients may be treated with inhaled treprostinil up to 15 breaths QID based upon tolerability. Change from baseline to Week 24 of treatment in FVC (absolute or percent predicted) as primary efficacy endpoint will be assessed. Parameters that may be assessed include time to exacerbation of underlying lung disease, 6 meter walk distance test (6MWD), all-cause mortality/survival, time to death, additional analyses of FVC (e.g. absolute and relative change), changes from baseline in $SpO_2$, diffusing capacity of the lungs for carbon monoxide (DLCO), NT-proBNP, and King's Brief Interstitial Lung Disease Questionnaire.

REFERENCES

1. Collard et al., *American Journal of Respiratory and Critical Care Medicine*, Volume 194 Number 3, pg. 265.
2. Meyer et al., (2017 Apr. 3). *Therapeutics and Clinical Risk Management.* 13: 427-437.

Example 3: Inhaled Treprostinil in Pulmonary Hypertension Due to Interstitial Lung Disease No therapies are currently approved for the treatment of pulmonary hypertension in patients with interstitial lung disease. The safety and efficacy of inhaled treprostinil for patients with this condition are unclear.

Methods

We enrolled patients with interstitial lung disease and pulmonary hypertension (documented by right heart catheterization) in a multicenter, randomized, double-blind, placebo-controlled, 16-week trial. Patients were assigned in a 1:1 ratio to receive inhaled treprostinil, administered by means of an ultrasonic, pulsed-delivery nebulizer in up to 12 breaths (total, 72 μg) four times daily, or placebo. The primary efficacy end point was the difference between the two treatment groups in the change in peak 6-minute walk distance from baseline to week 16. Secondary end points included the change in N-terminal pro-B-type natriuretic peptide (NT-proBNP) level at week 16 and the time to clinical worsening.

Results

A total of 326 patients underwent randomization, with 163 assigned to inhaled treprostinil and 163 to placebo. Baseline characteristics were similar in the two groups. At week 16, the least-squares mean difference between the treprostinil group and the placebo group in the change from baseline in the 6-minute walk distance was 31.12 m (95% confidence interval [CI], 16.85 to 45.39; P<0.001). There was a reduction of 15% in NT-proBNP levels from baseline with inhaled treprostinil as compared with an increase of 46% with placebo (treatment ratio, 0.58; 95% CI, 0.47 to 0.72; P<0.001). Clinical worsening occurred in 37 patients (22.7%) in the treprostinil group as compared with 54 patients (33.1%) in the placebo group (hazard ratio, 0.61; 95% CI, 0.40 to 0.92; P=0.04 by the log-rank test). The most frequently reported adverse events were cough, headache, dyspnea, dizziness, nausea, fatigue, and diarrhea.

Conclusions

In patients with pulmonary hypertension due to interstitial lung disease, inhaled treprostinil improved exercise capacity from baseline, assessed with the use of a 6-minute walk test, as compared with placebo.

Precapillary pulmonary hypertension is defined as an elevation in mean pulmonary arterial pressure and pulmonary vascular resistance.[1] In the World Health Organization (WHO) classification of pulmonary hypertension, precapillary pulmonary hypertension due to lung disease is classified as group 3. The most common lung diseases associated with group 3 pulmonary hypertension are chronic obstructive pulmonary disease and interstitial lung disease.

Pulmonary hypertension has been reported in up to 86% of patients with interstitial lung disease and is associated with reduced exercise capacity, greater need for supplemental oxygen, decreased quality of life, and earlier death.[2-4] Despite the global prevalence and poor clinical course of pulmonary hypertension due to interstitial lung disease, there are currently no approved therapies for these patients. Although data are limited, therapies approved for group 1 pulmonary hyper-tension (pulmonary arterial hypertension) have been used to treat group 3 pulmonary hypertension.[5] Previous studies of vasodilator therapies have shown conflicting results. The largest trial to date evaluated the soluble guanylate cyclase stimulator riociguat in a patient population with group 3 pulmonary hypertension and was stopped early owing to serious harm.[6]

Treprostinil is a stable analogue of prostacyclin, which promotes direct vasodilation of pulmonary and systemic arterial vascular beds and inhibits platelet aggregation.[7] An inhaled formulation of treprostinil was previously shown to improve exercise capacity after 12 weeks of therapy in patients with group 1 pulmonary hypertension.[8] Data from previously completed pilot studies suggest that inhaled treprostinil can improve hemodynamics and functional capacity in patients with group 3 pulmonary hypertension.[9-12] Therefore, the objective of the INCREASE trial was to evaluate the safety and efficacy of inhaled treprostinil in patients with pulmonary hypertension due to interstitial lung disease.

Trial Design and Oversight

INCREASE was a multicenter, randomized, double-blind, placebo-controlled trial. The trial was monitored by an independent data and safety monitoring committee and was conducted in accordance with Good Clinical Practice guidelines.

Trial Population

The trial population consisted of patients 18 years of age or older in whom interstitial lung disease was diagnosed on the basis of evidence of diffuse parenchymal lung disease on computed tomography of the chest (not centrally adjudicated) performed within 6 months before randomization. Confirmation of group 3 pulmonary hypertension by right heart catheterization within 1 year before randomization was required. Group 3 pulmonary hypertension was defined by pulmonary vascular resistance of more than 3 Wood units, pulmonary capillary wedge pressure of 15 mm Hg or lower, and mean pulmonary arterial pressure of 25 mm Hg or higher. Patients with group 3 pulmonary hypertension due to connective tissue disease were also required to have a baseline forced vital capacity of less than 70%. Eligible patients also had to walk at least 100 m during a 6-minute walk test. Patients receiving drug treatment (i.e., pirfenidone or nintedanib) for their underlying lung disease were required to have been receiving a stable dose for at least 30 days before undergoing randomization. Patients receiving approved therapy for pulmonary arterial hypertension within 60 days before randomization were not eligible for enrollment. Written informed consent was obtained from all the patients.

TABLE 4

Characteristics of the Patients at Baseline.*

| Characteristic | Inhaled Treprostinil (N = 163) | Placebo (N = 163) | All Patients (N = 326) |
|---|---|---|---|
| Female sex—no. (%) | 85 (52.1) | 68 (41.7) | 153 (46.9) |
| Mean age at randomization (range)—yr | 65.6 (26-90) | 67.4 (36-85) | 66.5 (26-90) |
| Age distribution—no. (%) | | | |
| <65 yr | 64 (39.3) | 48 (29.4) | 112 (34.4) |
| 65 to <80 yr | 83 (50.9) | 100 (61.3) | 183 (56.1) |
| ≥80 yr | 16 (9.8) | 15 (9.2) | 31 (9.5) |
| Race or ethnic group—no. (%)† | | | |
| White | 112 (68.7) | 126 (77.3) | 238 (73.0) |
| Black or African American | 41 (25.2) | 30 (18.4) | 71 (21.8) |
| American Indian or Alaska Native | 2 (1.2) | 1 (0.6) | 3 (0.9) |
| Asian | 7 (4.3 | 5 (3.1) | 12 (3.7) |
| Multiple | 0 | 1 (0.6) | 1 (0.3) |
| Unknown | 1 (0.6) | 0 | 1 (0.03) |
| Hispanic or Latino ethnic group—no. (%)† | | | |
| Yes | 11 (6.7) | 16 (9.8) | 27 (8.3) |
| No | 152 (93.3) | 146 (89.6) | 298 (91.4) |
| Data missing | 0 | 1 (0.6) | 1 (0.3) |
| Mean time since diagnosis—yr | 0.54 ± 1.16 | 0.54 ± 1.31 | 0.54 ± 1.23 |
| Cause of lung disease—no. (%) | | | |
| Idiopathic interstitial pneumonia | 65 (39.9) | 81 (49.7) | 146 (44.8) |
| Chronic hypersensitivity pneumonitis | 10 (6.1) | 9 (5.5) | 19 (5.8) |
| Occupational lung disease | 5 (3.1) | 1 (0.6) | 6 (1.8) |
| Combined pulmonary fibrosis and emphysema | 42 (25.8) | 40 (24.5) | 82 (25.2) |

TABLE 4-continued

Characteristics of the Patients at Baseline.*

| Characteristic | Inhaled Treprostinil (N = 163) | Placebo (N = 163) | All Patients (N = 326) |
|---|---|---|---|
| Connective tissue disease | 40 (24.5) | 32 (19.6) | 72 (22.1) |
| Other | 1 (0.6) | 0 | 1 (0.3) |
| Idiopathic interstitial pneumonia subcategory—no. (%) | | | |
| Idiopathic pulmonary fibrosis | 37 (22.7) | 55 (33.7) | 92 (28.2) |
| Idiopathic nonspecific interstitial pneumonia | 21 (12.9) | 16 (9.8) | 37 (11.3) |
| Respiratory bronchiolitis associated with interstitial lung disease | 2 (1.2) | 0 | 2 (0.6) |
| Desquamative interstitial pneumonia | 0 | 1 (0.6) | 1 (0.3) |
| Acute interstitial pneumonia | 0 | 1 (0.6) | 1 (0.3) |
| Unclassified idiopathic interstitial pneumonia | 5 (3.1) | 8 (4.9) | 13 (4.0) |
| Use of supplemental oxygen—no. (%) | 119 (73.0) | 114 (69.9) | 233 (71.5) |
| Background therapy—no (%) | | | |
| None | 133 (81.6) | 119 (73.0) | 252 (77.3) |
| Pirfenidone only | 19 (11.7) | 25 (15.3) | 44 (13.5) |
| Nintedanib only | 11 (6.7) | 19 (11.7) | 30 (9.2) |

*Plus-minus values are means ± SD. Additional patient characteristics at baseline are provided in Table S2 in the Supplementary Appendix. Percentages may not total 100 because of rounding.
†Race and ethnic group were reported by the patient.

Trial Procedures

Within 30 days after screening, eligible patients were randomly assigned in a 1:1 ratio to receive inhaled treprostinil (Tyvaso, United Therapeutics) or placebo in a double-blind manner. Randomization, based on permuted blocks, was stratified by baseline 6-minute walk distance (≤350 m vs. >350 m) and was implemented through an interactive Web-response system. Inhaled treprostinil (0.6 mg per milliliter) was administered by means of an ultrasonic, pulsed-delivery nebulizer at 6 μg per breath. Placebo was administered similarly as a visually identical solution. The first dose of trial drug (3 breaths) was administered in the clinic, followed by at least a 1-hour observation period. The dose of treprostinil or placebo was adjusted, with dose escalation (an additional 1 breath four times daily) occurring as often as every 3 days, with a target dose of 9 breaths four times daily and a maximum dose of 12 breaths four times daily. Investigators adjusted the dose on an individual patient basis to achieve the maximum tolerated dose leading to functional improvement.

Trial Assessments

The 6-minute walk test was performed and laboratory data were obtained at baseline and at weeks 4, 8, 12, and 16, or at the time of early discontinuation of treprostinil or placebo. Each 6-minute walk test was performed 10 to 60 minutes after the most recent dose of active drug or placebo, which is the time of peak plasma treprostinil exposure. A trough test was performed at week 15 at least 4 hours after the participant received a dose of treprostinil or placebo and at least 24 hours before the week 16 test. Pulse oximetry was performed immediately before, during, and after each 6-minute walk test. Measurement of N-terminal pro-B-type natriuretic peptide (NT-proBNP) levels and pulmonary function tests were performed at baseline and at weeks 8 and 16 (or at early discontinuation) after the patients recovered from the 6-minute walk test. The St. George's Respiratory Questionnaire (SGRQ), a quality-of-life measure, was completed at baseline and week 16 or at the time of early discontinuation.

Outcome Measures

The primary end point of the trial was the difference between the two groups in the change in peak 6-minute walk distance from baseline to week 16. Secondary efficacy end points were analyzed in the following hierarchical testing order: the change in NT-proBNP level from baseline to week 16, the time to clinical worsening, the change in 6-minute walk distance at peak plasma treprostinil level at week 12, and the change in 6-minute walk distance at trough treprostinil level at week 15. The time to clinical worsening was evaluated from the time of randomization until the patient's withdrawal from the trial and was defined as the time until the occurrence of any one of the following events: hospitalization for a cardiopulmonary indication, a decrease in 6-minute walk distance greater than 15% from baseline that was directly related to the disease under study at two consecutive visits and at least 24 hours apart, death from any cause, or lung transplantation.

Exploratory end points were the changes in peak 6-minute walk distance at weeks 4 and 8, quality of life as measured with the use of the SGRQ at week 16, and the distance-saturation product (calculated by multiplying the total distance walked by the lowest oxygen saturation measurement during the 6-minute walk) at week 16. Safety end points included adverse events, abnormal laboratory results, oxygenation as measured by pulse oximetry (Spo2) and supplemental oxygen requirement, changes in pulmonary function test results, hospitalization for a cardiopulmonary indication, and investigator-reported exacerbations of underlying lung disease, defined as acute, clinically significant respiratory deterioration characterized by evidence of new widespread alveolar abnormality.

Statistical Analysis

Original estimates suggested that with 266 patients randomly assigned in a 1:1 ratio to receive inhaled treprostinil or placebo, the trial would have at least 90% power at a significance level of 0.05 (two-sided) to detect a between-group difference of 30 m in the change in peak 6-minute walk distance from baseline at week 16, assuming a standard deviation of 75 m. To account for approximately 15% of participants discontinuing the trial, 314 patients would need to be enrolled.

For the primary efficacy analysis, the change in 6-minute walk distance was analyzed by mixed-model repeated-measures methods, under the assumption that missing data were missing at random. The model included the change from baseline to peak 6-minute walk distance as the dependent variable, with treatment, week, and treatment-by-week interaction as fixed effects, and the baseline 6-minute walk distance as a covariate. A sensitivity analysis for the primary end point was performed by means of a multiple imputation approach with a multivariate normal imputation model according to the Markov chain Monte Carlo method. The imputation model included treatment group, all scheduled visits, the patient's sex, and the patient's age at randomization. If the result for the primary efficacy end point was significant, secondary efficacy end points were to be evaluated according to a hierarchical testing procedure. Confidence intervals have not been adjusted for multiplicity and cannot be used to infer definitive treatment effects for secondary efficacy end points.

Results

Patients

Figure 2:
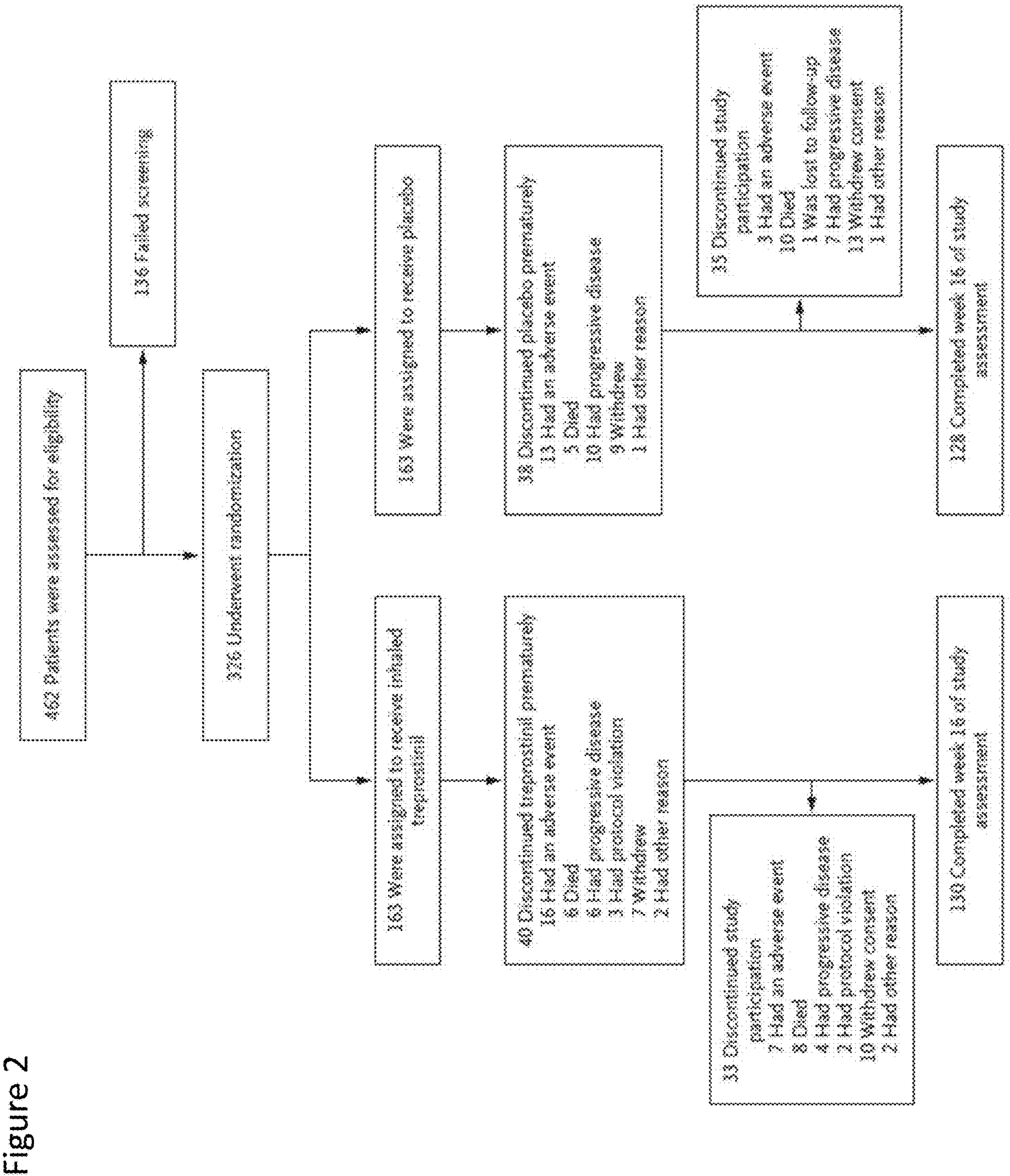
Figure 3:
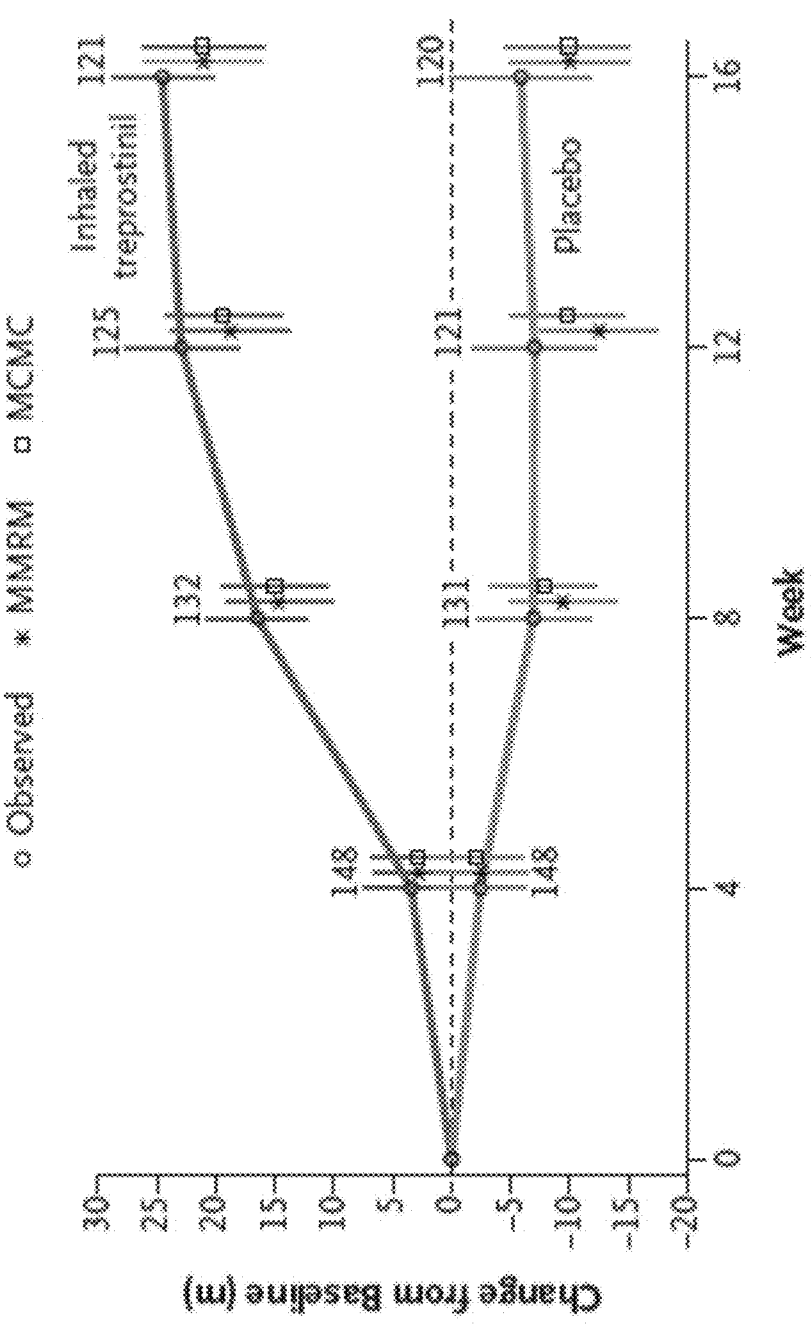

Of 462 patients screened for eligibility, 326 were enrolled at 93 centers and were randomly assigned to receive placebo (163 patients) or inhaled treprostinil (163 patients) (FIG. 2). Baseline characteristics were similar in the two groups (Table 4). The mean age of the patients was 66.5 years, 46.9% were female, and the most common diagnosis was idiopathic interstitial pneumonia (in 44.8%). At baseline, the mean 6-minute walk distance was 259.6 m, the mean pulmonary vascular resistance was 6.2 Wood units, and the mean NT-proBNP level was 1832.9 pg per milliliter.

Exposure and Follow-Up

Patients in the treprostinil group took a median of 11 breaths from the inhaler (66 μg) at each of four daily sessions at week 12 and 12 breaths (72 μg) per session at week 16. The percentage of patients in this group who took 10 to 12 breaths (60 to 72 μg) per session was 57.0% at week 12 and 57.8% at week 16. Patients in the placebo group took a median of 12 breaths from the inhaler per session at weeks 12 and 16.

Forty patients assigned to receive inhaled treprostinil (24.5%) and 38 assigned to placebo (23.3%) discontinued the assigned regimen pre-maturely. These patients were encouraged to remain in the trial and complete assessments through week 16; 33 patients in the treprostinil group and 35 in the placebo group discontinued participation in the trial. The reasons for discontinuation are shown in FIG. 2.

Primary End Point

Figure 4:
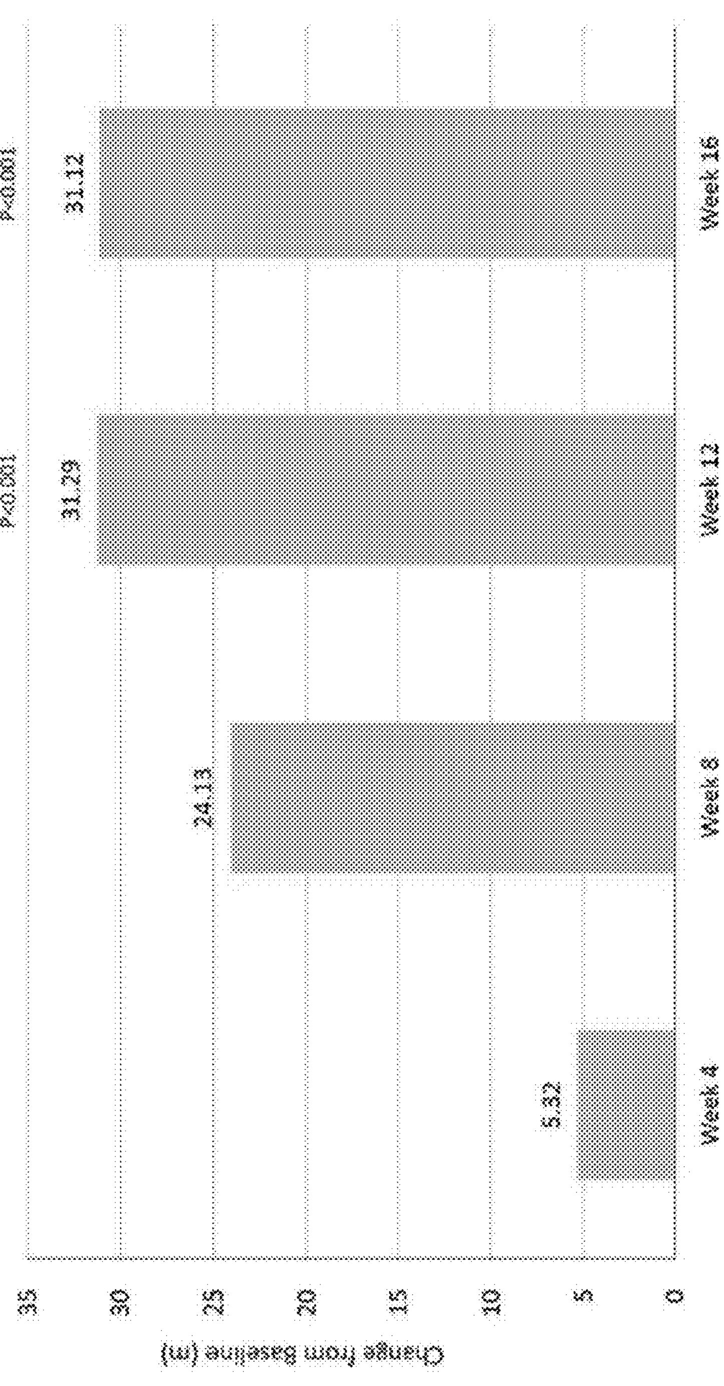
Figure 5:
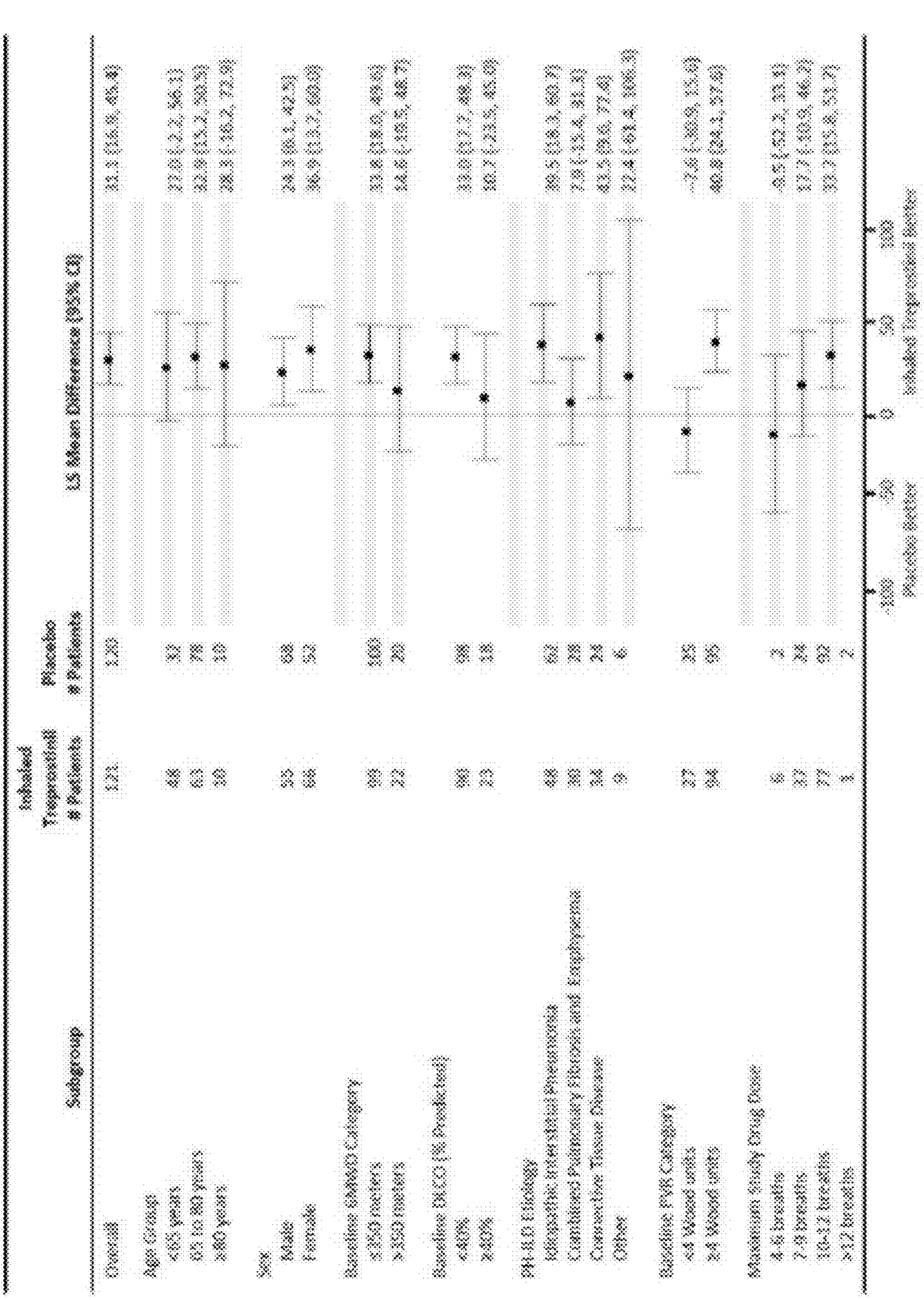

Mean within-group changes in the 6-minute walk distance are shown in FIG. 2. Mixed-model repeated-measures analysis showed that the least-squares mean difference between the treprostinil group and the placebo group in the change from baseline in peak 6-minute walk distance was 31.12 m (95% confidence interval [CI], 16.85 to 45.39; P<0.001) (Table 5 and FIG. 4). Similar effects were observed across subgroups, including subgroups defined by disease cause and severity (as measured by baseline 6-minute walk distance), baseline hemodynamics, and dose group (FIG. 5). In addition, the between-group difference in the change from baseline in peak 6-minute walk distance at week 16 was significant when analyzed with multiple imputation according to the Markov chain Monte Carlo method (30.97 m; 95% CI, 16.53 to 45.41; P<0.001) (FIG. 6).

TABLE 5

Summary of Primary and Secondary End Points.*

| End Point | Inhaled Treprostinil (N = 163) | Placebo (N = 163) | Treatment Effect (95% CI) | P Value |
|---|---|---|---|---|
| **Primary end point** | | | | |
| Change in peak 6-minute walk distance from baseline to wk 16—m† | 21.08 ± 5.12 | −10.04 ± 5.12 | 31.12 ± 7.25 (16.85 to 45.39)‡ | <0.001 |
| **Secondary end points§** | | | | |
| **Change in plasma concentration of NT-proBNP from baseline to wk 16¶** | | | | |
| Mean (±SD) change—pg/ml | −396.35 ± 1904.90 | 1453.95 ± 7296.20 | | |
| Median—pg/ml | −22.65 | 20.65 | | |
| Range—pg/ml | −11,433.0 to 5373.1 | −5483.3 to 87,148.3 | | |
| Ratio to baseline | 0.85 ± 0.06 | 1.46 ± 0.11 | ±0.58 ± 0.06 (0.47 to 0.72)‖ | <0.001 |
| Occurrence of clinical worsening—no. (%) | | | 0.61 (0.4 to 0.92)** | 0.04 |
| Any event | 37 (22.7) | 54 (33.1) | | |
| Hospitalization for cardiopulmonary indication | 18 (11.0) | 24 (14.7) | | |
| Decrease in 6 minute walk distance of >15% from baseline | 13 (8.0) | 26 (16.0) | | |
| Death from any cause | 4 (2.5) | 4 (2.5) | | |
| Lung transplantation | 2 (1.2) | 0 | | |
| Least-squares mean change in peak 6-minute walk distance from baseline to wk 12—m† | 18.77 ± 4.99 | −12.52 ± 5.01 | 31.29 ± 7.07 (17.37 to 45.21)‡ | <0.001 |

TABLE 5-continued

| Summary of Primary and Secondary End Points.* | | | | |
|---|---|---|---|---|
| End Point | Inhaled Treprostinil (N = 163) | Placebo (N = 163) | Treatment Effect (95% CI) | P Value |
| Least-squares mean change in trough 6-minute walk distance from baseline to wk 15—m | 9.3 ± 5.5 | −12.7 ± 5.5 | 21.99 ± 7.7 (6.85 to 37.14)‡ | 0.005†† |

*Plus-minus values are means ± SE, unless otherwise indicated. For secondary end points, the confidence intervals (CIs) have not been adjusted for multiplicity and cannot be used to infer definitive treatment effects. NT-proBNP denotes N-terminal pro-B-type natriuretic peptide.

†The effect of inhaled treprostinil as compared with placebo on the change in 6-minute walk distance was evaluated with the use of a mixed-model repeat measurement with the change from baseline in peak 6-minute walk distance as the dependent variable; treatment, week, and treatment-by-week interaction as the fixed effects; baseline 6-minute walk distance as the covariate; and subject as the random effect. Results are shown in Figures S1 and S3.

‡This is a least-squares mean difference between the groups.

§The effect of inhaled treprostinil as compared with placebo on the change in log-transformed NT-proBNP was evaluated with the use of a mixed-model repeat measurement with the change from baseline in log-transformed NT-proBNP as the dependent variable; treatment, week, and treatment-by-week interaction as the fixed effects; and log-transformed baseline NT-proBNP as the covariate. Ratio to baseline is the least-squares mean of the change from baseline in log-transformed data.

¶The change in plasma concentration of NT-proBNP from baseline to week 16 was assessed in 156 patients in the treprostinil group and 160 in the placebo group.

||This is the treatment ratio, which is the ratio of ratios between two treatment groups.

**This is a hazard ratio, calculated from a Cox proportional-hazards model. The P value was calculated with the use of a log-rank test stratified by the baseline 6-minute walk distance category.

††The P value was obtained from 100 multiple imputations with Markov chain Monte Carlo estimation with the use of analysis of covariance (ANCOVA) modeling, with the change from baseline in peak 6-minute walk distance as the dependent variable, treatment as a fixed effect, and baseline 6-minute walk distance as a covariate.

Secondary and Exploratory End Points

Figure 7:
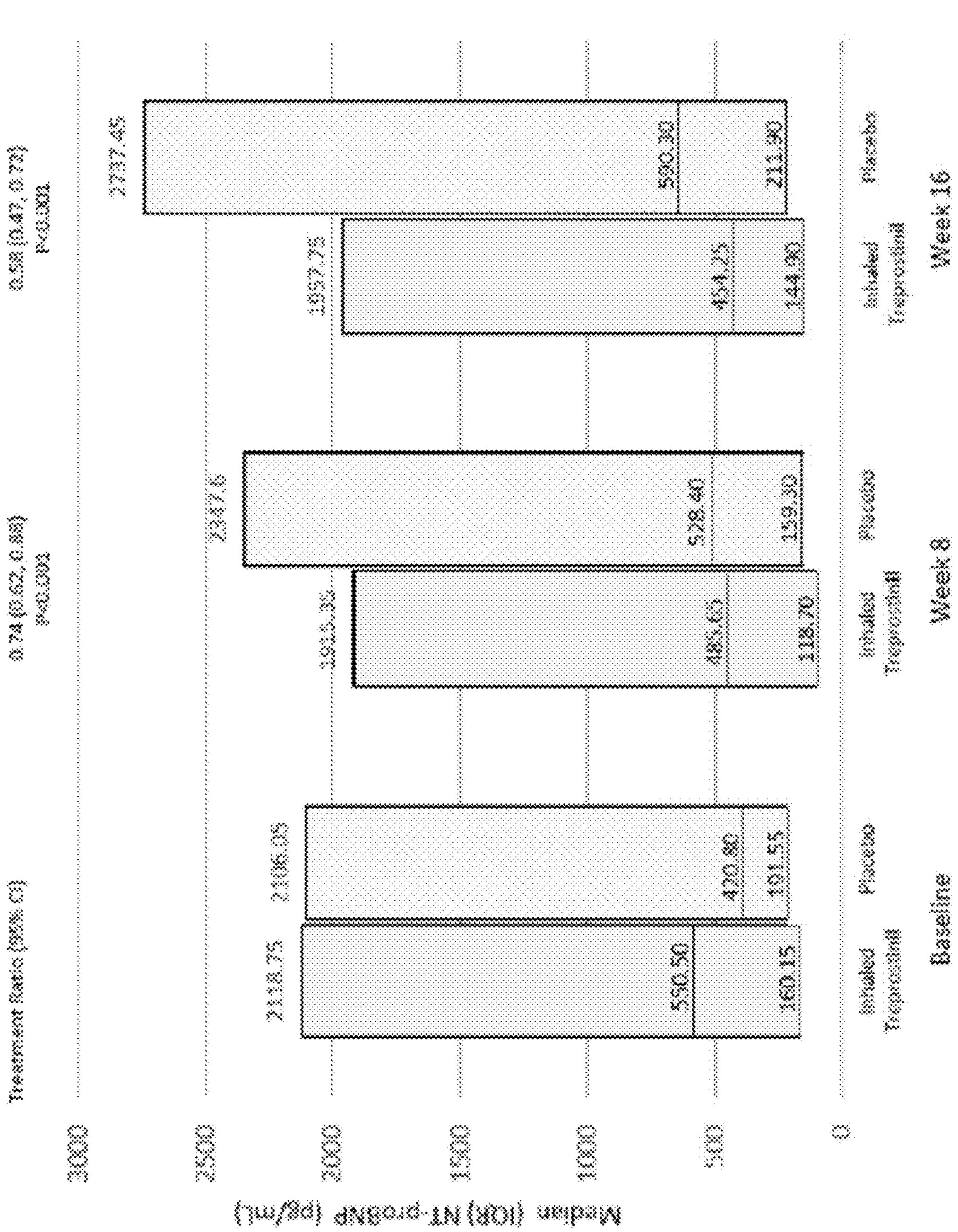
Figure 8:
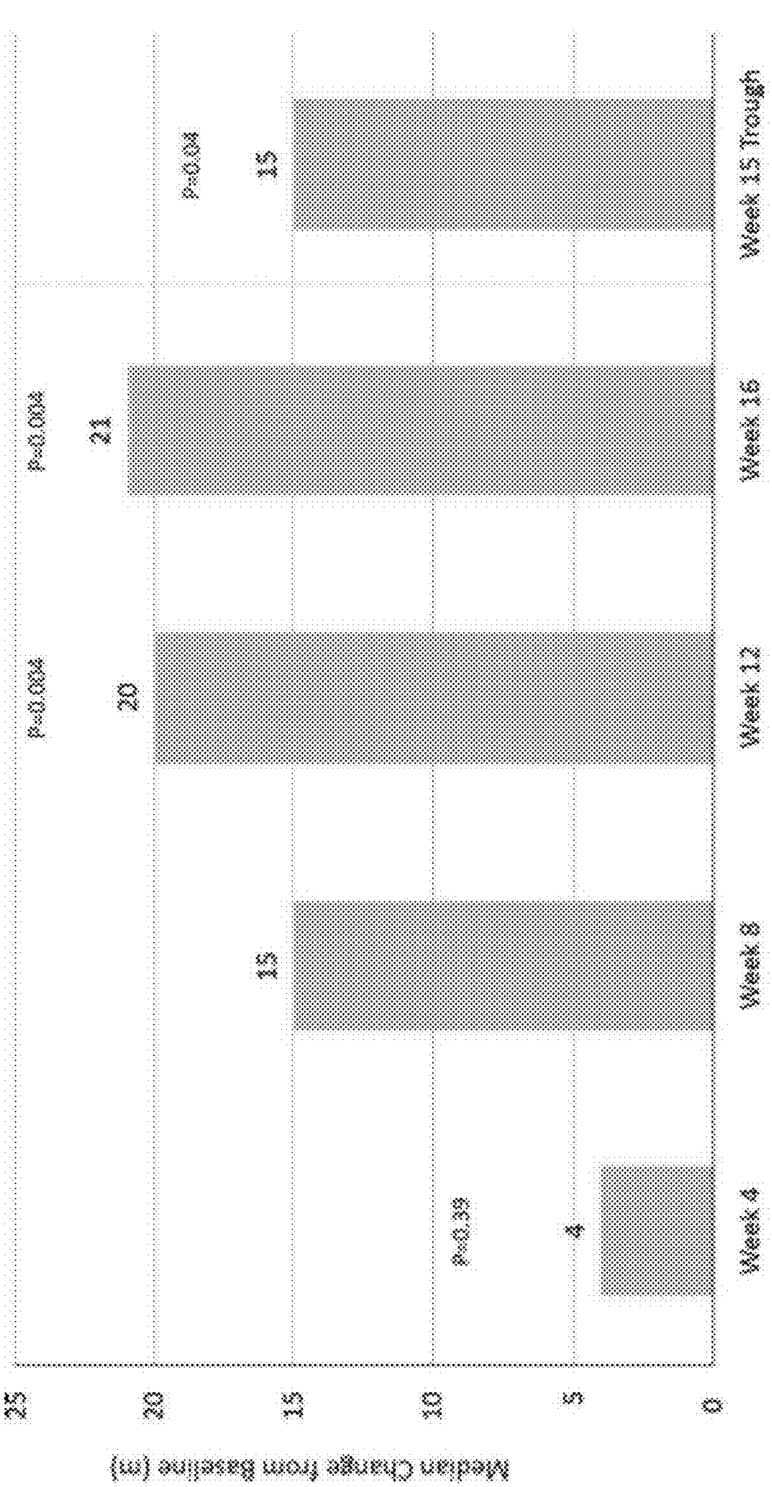

Patients assigned to inhaled treprostinil, as compared with those assigned to placebo, showed significant improvements in each of the secondary end points (Table 5). The NT-proBNP level decreased 15% from baseline with inhaled treprostinil and increased 46% from baseline with placebo, as assessed by the least-squares mean for the log-transformed ratio to the baseline level at week 16 (treatment ratio, 0.58; 95% CI, 0.47 to 0.72; P<0.001) (FIG. 7). Clinical worsening occurred in 37 patients (22.7%) in the treprostinil group, as compared with 54 patients (33.1%) in the placebo group (hazard ratio, 0.61; 9500 CI, 0.40 to 0.92; P=0.04 by the log-rank test) (FIG. 1). The least-squares mean change from baseline to week 12 in peak 6-minute walk distance was 31.29 m greater in the treprostinil group than in the placebo group (P<0.001), and the change from baseline to week 15 in trough 6-minute walk distance was 21.99 m greater in the treprostinil group (P=0.004). There was no significant between-group difference in patient-reported quality of life as assessed with the SGRQ or in the distance-saturation product at week 16.

Safety End Points

TABLE 6

| Summary of Adverse Events | | | |
|---|---|---|---|
| Variable | Inhaled Treprostinil (N = 163) | Placebo (N = 163) | P Value* |
| Total no. of adverse events | 890 | 793 | |
| Patients with ≥1 adverse event—no. (%) | 152 (93.3) | 149 (91.4) | 0.68 |
| Total no. of serious adverse events† | 53 | 89 | |
| Patients with ≥1 serious adverse event—no. (%) | 38 (23.3) | 42 (25.8) | 0.70 |
| Total no. of adverse events leading to withdrawal of treprostinil or placebo | 47 | 38 | |
| Most frequently occurring adverse events—no. of patients (%)‡ | | | |
| Cough | 71 (43.6) | 54 (33.1) | 0.07 |
| Headache | 45 (27.6) | 32 (19.6) | 0.12 |
| Dyspnea | 41 (25.2) | 51 (31.3) | 0.27 |
| Dizziness | 30 (18.4) | 23 (14.1) | 0.37 |
| Nausea | 25 (15.3) | 26 (16.0) | >0.99 |
| Fatigue | 23 (14.1) | 23 (14.1) | >0.99 |
| Diarrhea | 22 (13.5) | 19 (11.7) | 0.74 |
| Throat irritation | 20 (12.3) | 6 (3.7) | 0.007 |
| Oropharyngeal pain | 18 (11.0) | 4 (2.5) | 0.003 |
| NT-proBNP increased | 9 (5.5) | 25 (15.3) | 0.006 |

*P values were calculated with the use of Fisher's exact test.

‡Shown are the most frequently occurring adverse events occurring in more than 10% of patients in either group in the safety population, which comprised all patients who underwent randomization and received at least one dose of treprostinil or placebo.

The most frequently reported adverse events were cough, headache, dyspnea, dizziness, nausea, fatigue, and diarrhea (Table 6). Most of these events were of mild-to-moderate intensity. Serious adverse events occurred in 23.3% of the patients who received inhaled treprostinil and in 25.8% of those who received placebo. No serious adverse events were reported significantly more frequently in the treprostinil group than in the placebo group.

Significantly fewer patients in the treprostinil group than in the placebo group had exacerbations of underlying lung disease (43 [26.4%] vs. 63 [38.7%]; P=0.02 by Fisher's exact test). Fewer patients in the treprostinil group than in the placebo group had a first occurrence of clinical worsening that involved hospitalization for a cardiopulmonary indication (18 [11.0%] vs. 24 [14.7%]; P=0.41). Inhaled treprostinil had no deleterious effect on any pulmonary function test variable during the trial. There were no significant treatment-related changes in pulse oximetry or supplemental oxygen use in either group over the trial period.

DISCUSSION

Pulmonary hypertension frequently complicates the treatment of patients with interstitial lung disease and is associated with worse functional status, greater need for supplemental oxygen, and worse outcomes.[3,13] In the INCREASE trial, patients treated with inhaled treprostinil had significant improvements in exercise capacity, as evidenced by changes in the 6-minute walk distance. Treatment with inhaled treprostinil was also associated with a lower risk of clinical worsening than that in patients who received placebo, as well as reductions in NT-proBNP levels and fewer exacerbations of underlying lung disease, over the 16-week treatment period. The safety profile of inhaled treprostinil observed in this vulnerable patient population was similar to that reported in previous studies. The most frequently reported adverse events were cough, headache, dyspnea, dizziness, nausea, fatigue, and diarrhea. The use of inhaled treprostinil was not associated with any decrement in lung function.

Patients with group 3 pulmonary hypertension are often treated with systemic pulmonary vasodilators, which are currently approved only for treatment of group 1 pulmonary hypertension. However, there is concern that such agents could worsen ventilation-perfusion matching in patients with group 3 pulmonary hypertension. Inhaled agents have the advantage of preferentially redirecting blood flow to the best-ventilated lung units, thus reducing the risk of ventilation-perfusion mismatching.[9,14] Indeed, a retrospective study of inhaled treprostinil in patients with group 3 pulmonary hypertension showed that such patients had improvements in functional class and 6-minute walk distance without any adverse effect on peripheral oxygen saturation, reinforcing the concept of unchanged or even improved ventilation-perfusion matching with inhaled treprostinil.[10] Similarly, in the current trial, we found no evidence of worsened oxygenation, which further allays concerns about ventilation-perfusion mismatching.

The INCREASE trial was not without its limitations. The trial was of short duration, and 21% of the patients discontinued the trial prematurely (before week 16). In addition, events of clinical worsening and exacerbation of underlying lung disease were investigator-reported and not adjudicated by an independent review committee. Finally, the size of the favorable treatment effect on the 6-minute walk distance with inhaled treprostinil is similar to estimates of the minimum clinically important difference for this test in patients with pulmonary disease (21.7 to 37 m in a study by Nathan et al., and 24 to 45 m in a study by du Bois et al.).[15,16]

This study showed that among patients with pulmonary hypertension due to interstitial lung disease, treatment with inhaled treprostinil improved exercise capacity as shown by improvement in the 6-minute walk distance through the end of the 16-week treatment period. In addition, treatment with inhaled treprostinil was associated with a lower risk of clinical worsening than that with placebo, a reduction in NT-proBNP levels, and fewer exacerbations of underlying lung disease.

Supplemental Information

TABLE 7

Additional Baseline Patient Characteristics.

| | Inhaled Treprostinil (N = 163) | Placebo (N = 163) | All Patients (N = 326) |
|---|---|---|---|
| 6-minute walk distance, meters; mean (range) | 254.1 (100-538) | 265.1 (30-505) | 259.6 (30-538) |
| Median | 256.0 | 260.0 | 259.0 |
| Pulmonary vascular resistance, Woods units; mean (range) | 6.369 (3.11-8.05) | 6.013 (3.06-17.62) | 6.191 (3.06-18.05) |
| Median | 5.570 | 5.060 | 5.275 |
| NT-proBNP, pg/mL; mean (range) | 1857.53 (10.2-21942.0) | 1808.86 (23.0-16297.0) | 1832.88 (10.2-21942.0) |
| Median* | 550.50 | 420.80 | 503.85 |
| Pulmonary arterial pressure, mmHg; mean (range | 37.2 (25-74) | 36.0 (25-61) | 36.6 (25-74) |
| Median | 35.0 | 35.0 | 35.0 |
| Pulmonary capillary wedge pressure, mmHg; mean (range) | 10.1 (2-20) | 9.6 (0-15) | 9.8 (0-20) |
| Median | 10.0 | 10.0 | 10.0 |
| Pulmonary function tests | | | |
| FEV1% Predicted; mean (range) | 63.9 (23, 120) | 65.0 (22, 145) | |
| Median | 63.0 | 63.0 | |
| FVC % Predicted; mean (range) | 62.5 (24, 130) | 63.8 (20, 134) | |
| Median | 60.0 | 61.0 | |
| TLC % Predicted; mean (range) | 62.9 (25, 126) | 64.2 (30, 109) | |
| Median | 62.0 | 62.5 | |
| DLCO % Predicted; mean (range) | 30.0 (5, 86) | 28.1 (1, 86) | |
| Median | 29.0 | 26.0 | |

DLCO, lung diffusion capacity;
FEV1, forced expiratory volume in 1 second;
FVC, forced vital capacity;
NT-proBNP, N-terminal pro-brain natriuretic peptide;
TLC, total lung capacity
*N = 156 inhaled treprostinil; N = 160 placebo Table 8. St. George's Respiratory Questionnaire Results.

The St. George's Respiratory Questionnaire has a range of results from 0 to 100, with higher scores indicating greater impairment and with a minimum clinically important difference of 4 points.

TABLE 8

| | Inhaled Treprostinil N = 163 | | Placebo N = 163 | |
|---|---|---|---|---|
| Visit Statistic | Value | Change from Baseline | Value | Change from Baseline |
| Baseline | | | | |
| n | 143 | | 134 | |
| Mean (SD) | 57.17 (15.77) | | 57.67 (15.78) | |
| Median | 59.80 | | 56.30 | |
| Interquartile | 45.60, 67.90 | | 46.50 70.70 | |
| Min, Max | 14.7, 94.9 | | 18.4 88.6 | |
| Week 16 | | | | |
| n | 143 | 143 | 134 | 134 |
| Mean (SD) | 55.91 (17.07) | −1.25 (10.99) | 57.49 (15.33) | −0.18 (10.72) |
| Median | 56.30 | −0.70 | 55.50 | 0.10 |
| Interquartile | 40.50, 67.00 | −7.10, 5.20 | 46.80 69.70 | −6.50, 6.10 |
| Min, Max | 3.5, 92.0 | −40.4, 29.0 | 16.9 96.5 | −31.9, 33.3 |
| LS Mean (SE) | | −1.30 (0.87) | | −0.13 (0.90) |
| LS Mean Difference (SE) and (95% CI) | | −1.18, (1.25) (−3.63, 1.28) | | |

ANCOVA, analysis of covariance;
CI, confidence interval;
LS Mean, least squares mean;
SD, standard deviation;
SE, standard error The changes from baseline in Total Score and each of the 3 domain scores were analyzed by parametric ANCOVA with no imputation for missing data.

The confidence intervals have not been adjusted for multiplicity and cannot be used to infer definitive treatment effects.

TABLE S4

Distance Saturation Product Results by Study Visit (m %).

| Visit/Variable Statistic | Inhaled Treprostinil N = 163 | Placebo N = 163 |
|---|---|---|
| Baseline | | |
| n | 118 | 109 |
| Mean (SD) | 208.140 (81.130) | 218.247 (77.405) |
| Median | 201.320 | 215.760 |
| Interquartile | 150.060, 256.750 | 170.800, 268.800 |
| Min, Max | 77.04, 421.07 | 63.00, 417.35 |
| Week 16 Change from Baseline | | |
| n | 118 | 109 |
| Mean (SD) | 7.607 (45.680) | −4.803 (53.026) |
| Median | 8.385 | −1.950 |
| Interquartile | −12.960, 34.890 | −38.180, 32.000 |
| Min, Max | −217.26, 117.42 | −184.85, 129.28 |
| LS Mean (SE) | 7.2 (4.5) | −4.3 (4.7) |
| LS Mean Difference (SE) and 95% CI | 11.51 (6.5), 95% CI (−1.33, 24.35) | |

ANCOVA, analysis of covariance;
CI, confidence interval;
LS Mean, least squares mean;
SD, standard deviation;
SE, standard error;
$SpO_2$, saturation of peripheral capillary oxygenation Change in distance saturation product is the product of distance walked and lowest $SpO_2$ recorded during the 6-minute walk test.[7] Change from baseline to Week 16 in distance saturation product was analyzed by parametric ANCOVA with no imputation for missing distance saturation product values.

The confidence intervals have not been adjusted for multiplicity and cannot be used to infer definitive treatment effects.

TABLE 9

Serious Adverse Events by Preferred Term

| Serious Adverse Events | Inhaled treprostinil N = 163 n | Placebo N = 163 n |
|---|---|---|
| Any Serious Event | 53 events in 38 patients (23.3%) | 89 events in 42 patients (25.8%) |
| Acute respiratory failure | 4 | 5 |
| Death with unknown cause | 3 | 1 |
| Dyspnoea | 3 | 7 |
| Interstitial lung disease | 3 | 2 |
| Bronchitis | 2 | 1 |
| Chronic obstructive pulmonary disease | 2 | 2 |
| Chronic respiratory failure | 2 | 0 |
| Respiratory failure | 2 | 5 |
| Upper respiratory tract infection | 2 | 1 |
| Acute myocardial infarction | 1 | 2 |
| Acute right ventricular failure | 1 | 0 |
| Arrhythmia | 1 | 0 |
| B-cell lymphoma | 1 | 0 |
| Bronchopulmonary aspergillosis | 1 | 0 |
| Cardiac arrest | 1 | 2 |
| Cardiac failure congestive | 1 | 2 |
| Cardiopulmonary failure | 1 | 0 |
| Cellulitis | 1 | 0 |
| Cerebral haemorrhage | 1 | 0 |
| Chest pain | 1 | 1 |
| Combined pulmonary fibrosis and emphysema | 1 | 0 |
| Cor pulmonale | 1 | 0 |
| Haemoptysis | 1 | 0 |
| Hyperglycaemia | 1 | 0 |
| Hypervolaemia | 1 | 0 |

TABLE 9-continued

| Serious Adverse Events by Preferred Term | | |
|---|---|---|
| Serious Adverse Events | Inhaled treprostinil N = 163 n | Placebo N = 163 n |
| Hypoxia | 1 | 0 |
| Idiopathic pulmonary fibrosis | 1 | 4 |
| Influenza | 1 | 1 |
| Left ventricular failure | 1 | 0 |
| Pain in extremity | 1 | 0 |
| Pneumonia | 1 | 9 |
| Pneumothorax | 1 | 1 |
| Pulmonary hypertension | 1 | 1 |
| Pulmonary oedema | 1 | 0 |
| Rhinovirus infection | 1 | 0 |
| Right ventricular failure | 1 | 2 |
| Syncope | 1 | 1 |
| Tachycardia | 1 | 0 |
| Abdominal pain | 0 | 2 |
| Acute kidney injury | 0 | 1 |
| Aspiration | 0 | 1 |
| Atrial fibrillation | 0 | 1 |
| Bradycardia | 0 | 1 |
| Cardiac failure | 0 | 2 |
| Cardiac failure acute | 0 | 1 |
| Cardiogenic shock | 0 | 1 |
| Chronic right ventricular failure | 0 | 1 |
| Coagulopathy | 0 | 1 |
| Cor pulmonale acute | 0 | 1 |
| Coronary artery disease | 0 | 1 |
| Disease progression | 0 | 2 |
| Epistaxis | 0 | 1 |
| Fluid overload | 0 | 4 |
| Haematochezia | 0 | 1 |
| Hypertension | 0 | 1 |
| Lumbar vertebral fracture | 0 | 1 |
| Metabolic encephalopathy | 0 | 1 |
| Pain | 0 | 1 |
| Pneumonia influenzal | 0 | 1 |
| Post procedural infection | 0 | 1 |
| Presyncope | 0 | 2 |
| Pulmonary congestion | 0 | 1 |
| Respiratory distress | 0 | 1 |
| Scleroderma | 0 | 1 |
| Sepsis | 0 | 2 |
| Transplant dysfunction | 0 | 1 |
| Urosepsis | 0 | 1 |

TABLE 10

Analysis of Lung Function Test Parameters Using Mixed Model Repeated Measurement.

| Variable Visit Treatment | N | LS Mean | Contrast: Inhaled treprostinil - Placebo Estimated Difference (95% CI) | P-value |
|---|---|---|---|---|
| FVC (mL) | | | | |
| Week 8 | | | | |
| Inhaled treprostinil | 142 | 5.49 | 28.47 | 0.35 |
| Placebo | 141 | −22.98 | (−30.81, 87.74) | |
| Week 16 | | | | |
| Inhaled treprostinil | 130 | 9.77 | 44.40 | 0.21 |
| Placebo | 126 | −34.63 | (−25.25, 114.05) | |
| FVC (% predicted) | | | | |
| Week 8 | | | | |
| Inhaled treprostinil | 142 | 0.77 | 1.79 | |
| Placebo | 141 | −1.02 | (0.37, 3.21) | 0.01 |
| Week 16 | | | | |
| Inhaled treprostinil | 130 | 1.07 | 1.80 | 0.03 |
| Placebo | 126 | −0.72 | (0.20, 3.39) | |
| FEV1 (mL) | | | | |
| Week 8 | | | | |
| Inhaled treprostinil | 142 | −21.34 | −8.95 | 0.72 |
| Placebo | 141 | −12.39 | (−57.16, 39.26) | |
| Week 16 | | | | |
| Inhaled treprostinil | 130 | −32.18 | −2.56 | 0.93 |
| Placebo | 126 | −29.62 | (−57.67, 52.55) | |
| FEV1 (% predicted) | | | | |
| Week 8 | | | | |
| Inhaled treprostinil | 142 | −0.18 | 0.57 | 0.43 |
| Placebo | 141 | −0.75 | (−0.83, 1.96) | |
| Week 16 | | | | |
| Inhaled treprostinil | 130 | −0.24 | 0.38 | 0.65 |
| Placebo | 126 | −0.62 | (−1.25, 2.01) | |
| TLC (mL) | | | | |
| Week 8 | | | | |
| Inhaled treprostinil | 135 | −38.75 | −16.23 | 0.80 |
| Placebo | 136 | −22.51 | (−141.9, 109.41) | |
| Week 16 | | | | |
| Inhaled treprostinil | 127 | 45.43 | 17.37 | 0.85 |
| Placebo | 116 | 28.06 | (−158.9, 193.61) | |
| TLC (% predicted) | | | | |
| Week 8 | | | | |
| Inhaled treprostinil | 135 | −0.05 | 0.28 | 0.76 |
| Placebo | 136 | −0.32 | (−1.49, 2.05) | |
| Week 16 | | | | |
| Inhaled treprostinil | 127 | 2.52 | 1.49 | 0.34 |
| Placebo | 116 | 1.03 | (−1.57, 4.54) | |
| DLCO (mL/min/mmHg) | | | | |
| Week 8 | | | | |
| Inhaled treprostini | 136 | −0.27 | 0.19 | 0.56 |
| Placebo | 136 | −0.47 | (−0.45, 0.84) | |
| Week 16 | | | | |
| Inhaled treprostinil | 128 | −0.61 | 0.02 | 0.96 |
| Placebo | 112 | −0.63 | (−0.73, 0.76) | |
| DLCO (% predicted) | | | | |
| Week 8 | | | | |
| Inhaled treprostinil | 136 | −0.13 | 1.07 | 0.13 |
| Placebo | 136 | −1.20 | (−0.32, 2.47) | |
| Week 16 | | | | |
| Inhaled treprostinil | 128 | −1.14 | 0.60 | 0.44 |
| Placebo | 112 | −1.74 | (−0.93, 2.14) | |

CI, confidence interval;
DLCO, diffusing capacity of the lungs for carbon monoxide;
FEV1, forced expiratory volume in 1 second;
FVC, forced vital capacity;
TLC, total lung capacity;;
LS Mean, least squares mean;
SE, standard error;
TLC, total lung capacity
LS Mean (SE), P-values, estimated difference (SE), and associated 95% CIs are from the mixed model repeated measurement with the change from Baseline in pulmonary function test parameter as the dependent variable; treatment, week, treatment by week interaction as the fixed effects; Baseline measurement as the covariate; and subject as the random effect. An unstructured variance/covariance structure shared across treatment groups was used to model the within-subjects errors.

The confidence intervals and p-values have not been adjusted for multiplicity and cannot be used to infer definitive treatment effects.

TABLE 11

$SpO_2$ (%) Measured by Pulse Oximetry Results at Baseline and Week 16.

| | Inhaled Treprostinil N = 163 | | Placebo N = 163 | | |
|---|---|---|---|---|---|
| Visit Statistic | Value | Change from Pre-walk | Value | Change from Pre-Walk | P-value* |
| Baseline Pre-walk $SpO_2$ (%) | | | | | |
| n | 163 | | 162 | | |
| Mean (SD) | 95.3 (3.95) | | 94.5 (4.81) | | |
| Median | 96.0 | | 96.0 | | |
| Min, Max | 72, 100 | | 68, 100 | | |
| Baseline During Walk $SpO_2$ (%) | | | | | |
| n | 154 | 154 | 153 | 153 | 0.13 |
| Mean (SD) | 80.3 (8.22) | −15.0 (7.87) | 78.5 (8.20) | −16.1 (7.76) | |
| Median | 81.0 | −14.0 | 78.0 | −15.0 | |
| Min, Max | 53, 99 | −41, 2 | 53, 98 | −39, 4 | |
| Baseline Post-walk $SpO_2$ (%) | | | | | |
| n | 163 | 163 | 162 | 162 | 0.17 |
| Mean (SD) | 85.3 (7.31) | −9.9 (6.50) | 83.7 (8.74) | −10.9 (8.06) | |
| Median | 86.0 | −10.0 | 83.5 | −11.0 | |
| Min, Max | 59, 100 | −26, 5 | 57, 99 | −39, 7 | |
| Week 16 Pre-walk $SpO_2$ (%) | | | | | |
| n | 130 | | 122 | | |
| Mean (SD) | 94.5 (4.35) | | 94.5 (4.22) | | |
| Median | 95.0 | | 95.0 | | |
| Min, Max | 74, 100 | | 78, 100 | | |
| Week 16 During Walk $SpO_2$ (%) | | | | | |
| n | 123 | 123 | 114 | 114 | 0.27 |
| Mean (SD) | 76.8 (7.70) | −17.6 (7.01) | 78.2 (9.28) | −16.6 (9.04) | |
| Median | 77.0 | −17.0 | 79.0 | −16.0 | |
| Min, Max | 46, 99 | −38, −1 | 28, 98 | −61, −1 | |
| Week 16 Post-walk $SpO_2$ (%) | | | | | |
| n | 128 | 128 | 122 | 122 | 0.07 |
| Mean (SD) | 82.1 (9.24) | −12.4 (8.05) | 83.7 (7.75) | −10.8 (7.09) | |
| Median | 83.0 | −13.0 | 84.0 | −11.5 | |
| Min, Max | 51, 100 | −29, 3 | 65, 100 | −31, 6 | |

SD, standard deviation;

$SpO_2$, saturation of peripheral capillary oxygenation

*P-values are calculated from analysis of covariance with change from pre-walk as dependent variable, treatment as fixed effect, and baseline $SpO_2$ as covariate.

TABLE 12

Supplemental Oxygen Use (L/min) at Baseline and Week 16.

| | Inhaled Treprostinil N = 163 | | Placebo N = 163 | | |
|---|---|---|---|---|---|
| Visit Statistic | Value | Change from Baseline | Value | Change from Baseline | P-value* |
| Baseline Pre-walk (L/min) | | | | | |
| n | 163 | | 163 | | |
| Mean (SD) | 2.7 (2.2) | | 2.4 (2.0) | | |
| Median | 3.0 | | 2.0 | | |
| Min, Max | 0, 10 | | 0, 8 | | |
| Baseline During Walk (L/min) | | | | | |
| n | 163 | | 163 | | |
| Mean (SD) | 4.9 (4.0) | | 4.5 (3.8) | | |
| Median | 4.0 | | 4.0 | | |
| Min, Max | 0, 25 | | 0, 15 | | |

TABLE 12-continued

| Supplemental Oxygen Use (L/min) at Baseline and Week 16. | | | | | |
|---|---|---|---|---|---|
| | Inhaled Treprostinil N = 163 | | Placebo N = 163 | | |
| Visit Statistic | Value | Change from Baseline | Value | Change from Baseline | P-value* |
| Week 16 Pre-walk (L/min) | | | | | |
| n | 131 | 131 | 129 | 129 | 0.18 |
| Mean (SD) | 3.0 (2.5) | 0.4 (1.4) | 2.9 (2.4) | 0.6 (1.3) | |
| Median | 3.0 | 0.0 | 3.0 | 0.0 | |
| Min, Max | 0, 10 | −3, 6 | 0, 10 | −3, 5 | |
| Baseline During Walk (L/min) | | | | | |
| n | 129 | 129 | 123 | 123 | 0.39 |
| Mean (SD) | 4.9 (4.0) | 0.1 (0.8) | 4.6 (3.7) | 0.1 (0.3) | |
| Median | 4.0 | 0.0 | 4.0 | 0.0 | |
| Min, Max | 0, 25 | −2, 8 | 0, 15 | 0, 3 | |

SD, standard deviation

*P-values are calculated from analysis of covariance with change from baseline as dependent variable, treatment as fixed effect, and baseline oxygen use as covariate.

Subjects who did not use supplemental oxygen were coded as 0 in the summaries.

Subjects who received supplemental oxygen during the Baseline 6-minute walk test continued to receive the same flow rate at all subsequent 6-minute walk test assessments.

REFERENCES

1. Simonneau G, et al Eur Respir J 2019; 53: 1801913.
2. Nathan S D. Int J Clin Pract Suppl 2008; 160:21-8.
3. Nathan S D, et al. Clin Chest Med 2013; 34:695-705.
4. King C S, et al. Chest 2020; 158:1651-64.
5. Trammell A W, et al. Pulm Circ 2015; 5:356-63.
6. Nathan S D, et al. Lancet Respir Med 2019; 7:780-90.
7. Whittle B J, et al. Biochem Pharmacol 2012; 84:68-75.
8. McLaughlin V V, et al. J Am Coll Cardiol 2010; 55:1915-22.
9. Faria-Urbina M, et al. Lung 2018; 196:139-46.
10. Agarwal M, et al. J Heart Lung Transplant 2015; 34: Suppl:5343. abstract.
11. Bajwa A A, et al. Pulm Circ 2017; 7:82-8.
12. Wang L, et al. Int J Chron Obstruct Pulmon Dis 2017; 12:3353-60.
13. Lettieri C J, et al. Respir Med 2006; 100:1734-41.
14. Dernaika T A, et al. Respiration 2010; 79:377-82.
15. Nathan S D, et al. Respir Med 2015; 109:914-22.
16. du Bois R M, et al. Am J Respir Crit Care Med 2011; 183:1231-7.

Example 4. Aerosolized and Powder Inhaled Treprostinil

Randomized, 6-treatment, 6-period, 6-sequence, crossover study (6×6 Williams design) in 36 healthy volunteers was performed to compare nebulized inhaled treprostinil administered by Tyvaso® nebulizer and Treprostinil inhalation powder (TreT) administered via a dry powder inhaler (published US Patent Application 20190321290). 4 subjects discontinued the study early (COVID-19, n=2; withdrawal by subject, n=1; non-compliance with study requirements, n=1).

TABLE 13

| provides doses for Tyvaso and Tret administered treprosnil | |
|---|---|
| Tyvaso Dose | TreT Dose |
| 18 μg (3 nebulizer breaths) | 16 μg cartridge |
| 54 μg (9 nebulizer breaths) | 48 μg cartridge |
| 72 μg (12 nebulizer breaths) | 64 μg cartridge |

TABLE 14

Figure 9:
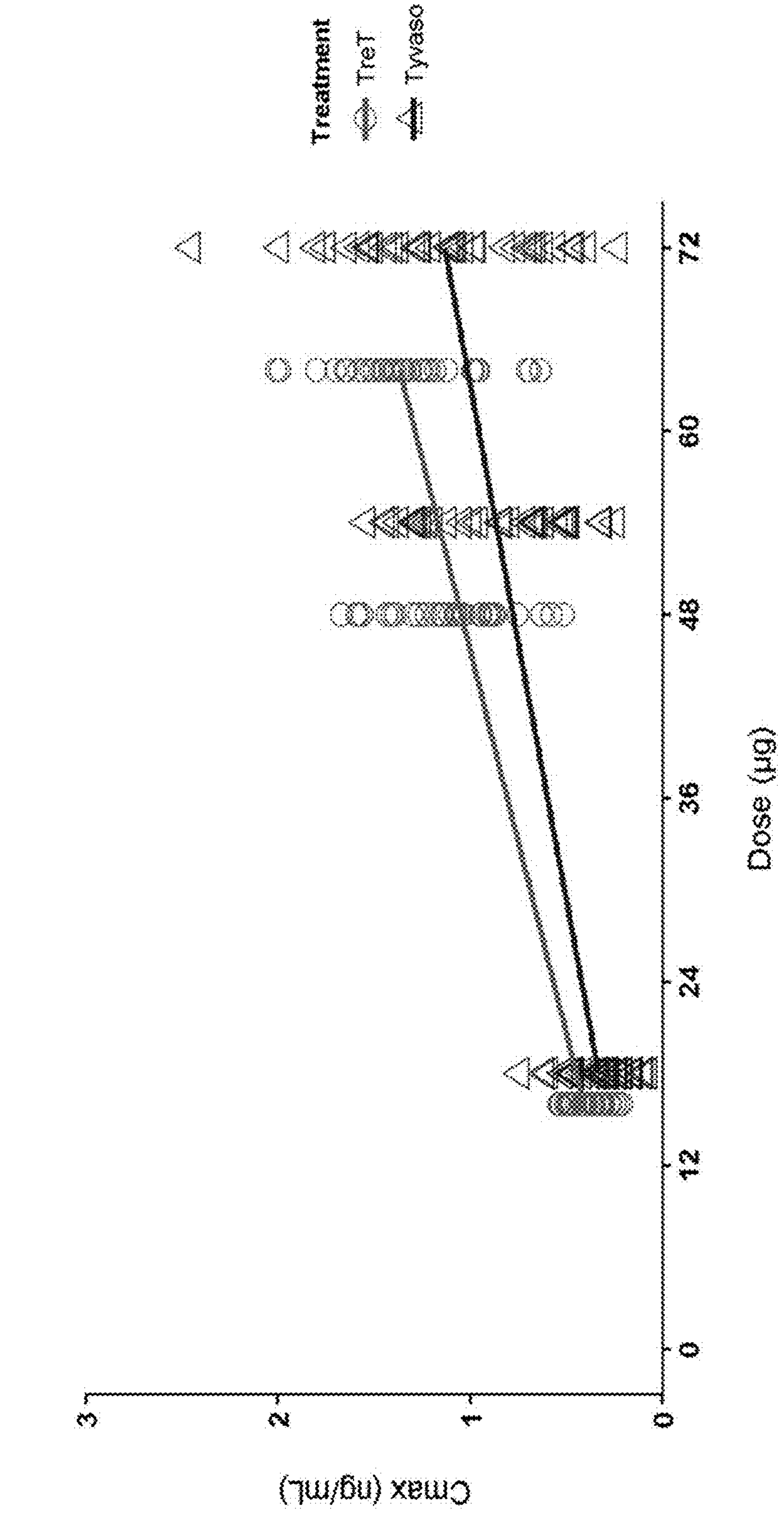
FIG. 9 is a plot showing a relationship between treprostinil AUC0-5 and dose for Treprostinil Inhalation Powder (TreT) administered by a dry powder inhaler and nebulized treprostinil administered by Tyvaso nebulizer.
Figure 10:
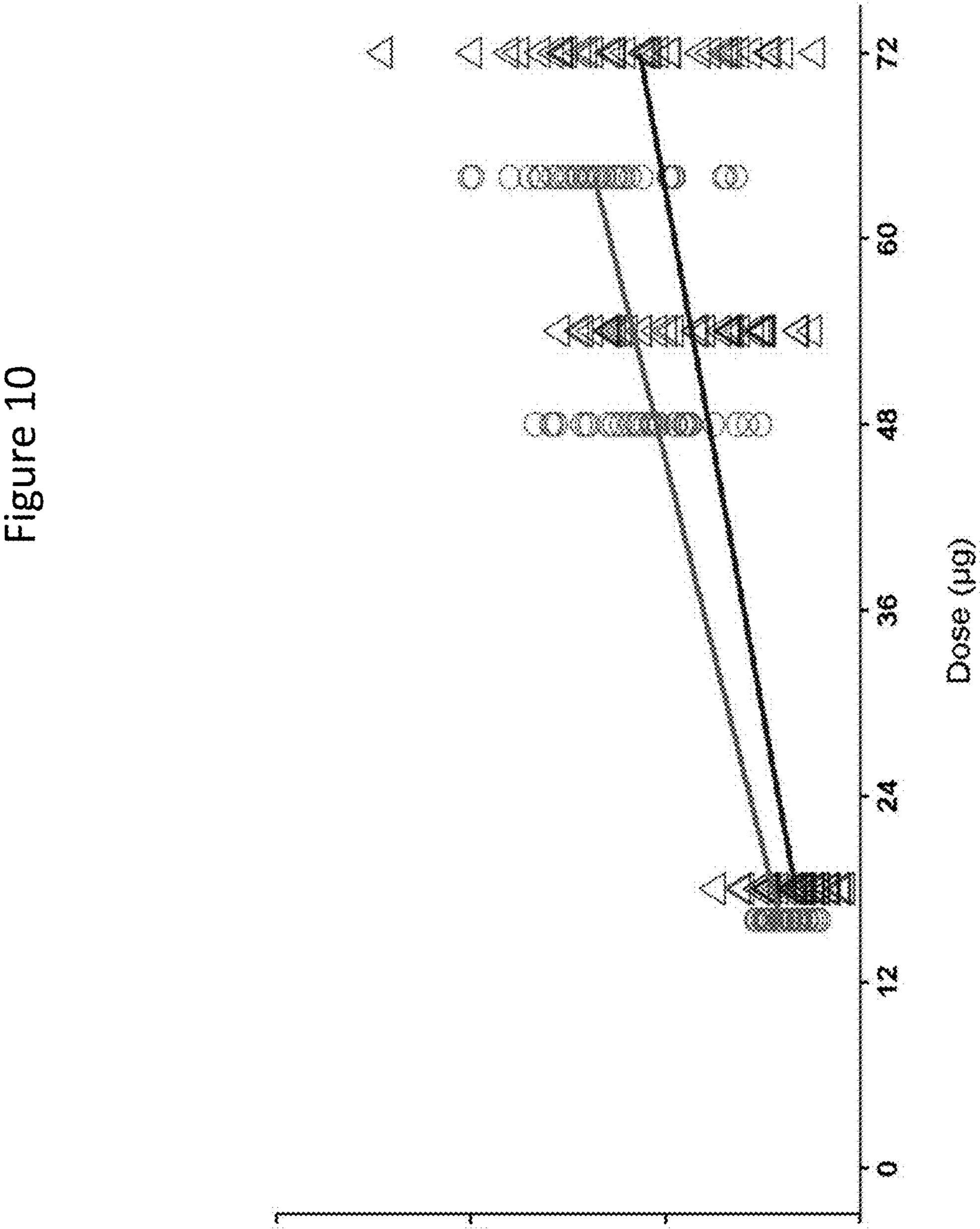
FIG. 10 is a plot showing a relationship between treprostinil Cmax and dose for Treprostinil Inhalation Powder (TreT) administered by a dry powder inhaler and nebulized treprostinil administered by Tyvaso nebulizer.

| Pharmacokinetic results for various doses for Tyvaso and TreT administered treprostinil. See also FIG. 9 and 10. | | | | | |
|---|---|---|---|---|---|
| Comparison | Parameter | Geometric LSM (TreT) [CV %] | Geometric LSM (Tyvaso) [CV %] | Geometric LSM Ratio (%) [TreT/Tyvaso] | 90% Confidence Interval |
| TreT 16 μg vs. Tyvaso 18 μg | AUC0-5 | 0.268 [24.1%] | 0.233 [44.1%] | 115 | (104.59, 127.42) |
| | Cmax | 0.377 [26.6%] | 0.291 [59.8%] | 130 | (115.55, 145.95) |
| TreT 48 μg vs. Tyvaso 54 μg | AUC0-5 | 0.766 [21.8%] | 0.757 [42.5%] | 101 | (91.63, 111.65) |
| | Cmax | 1.07 [28.9%] | 0.764 [53.4%] | 139 | (124.13, 156.73) |

TABLE 14-continued

| Pharmacokinetic results for various doses for Tyvaso and TreT administered treprostinil. See also FIG. 9 and 10. | | | | | |
|---|---|---|---|---|---|
| Comparison | Parameter | Geometric LSM (TreT) [CV %] | Geometric LSM (Tyvaso) [CV %] | Geometric LSM Ratio (%) [TreT/Tyvaso] | 90% Confidence Interval |
| TreT 64 μg vs. Tyvaso 72 μg | AUC0-5 | 0.937 [23.8%] | 1.02 [41.9%] | 91.5 | (83.16, 100.78) |
| | Cmax | 1.27 [28.5%] | 1.02 [54.7%] | 124 | (110.56, 139.61) |

TABLE 15

| Adverse events for various doses for Tyvaso and TreT administered treprostinil. | | | | | | |
|---|---|---|---|---|---|---|
| | TreT 16 μg N = 34 n (%) | Tyvaso 18 μg N = 34 n (%) | TreT 48 μg N = 34 n (%) | Tyvaso 54 μg N = 34 n (%) | TreT 64 μg N = 33 n (%) | Tyvaso 72 μg N = 35 n (%) |
| Adverse Events | 16 (47.1) | 13 (38.2) | 23 (67.6) | 21 (61.8) | 22 (66.7) | 25 (71.4) |
| Cough | 15 (44.1) | 11 (32.4) | 20 (58.8) | 18 (52.9) | 21 (63.6) | 24 (68.6) |
| Headache | 2 (5.9) | 3 (8.8) | 4 (11.8) | 7 (20.6) | 6 (18.2) | 6 (17.1) |
| Throat irritation | 1 (2.9) | 1 (2.9) | 3 (8.8) | 5 (14.7) | 3 (9.1) | 4 (11.4) |
| Dizziness | 1 (2.9) | 2 (5.9) | 1 (2.9) | 4 (11.8) | 2 (6.1) | 2 (5.7) |
| Nausea | 0 | 0 | 0 | 2 (5.9) | 2 (6.1) | 1 (2.9) |
| Chest discomfort | 1 (2.9) | 0 | 3 (8.8) | 2 (5.9) | 0 | 2 (5.7) |

Conclusions

AUC0-5 was generally comparable for each TreT and Tyvaso dose level. Cmax values for TreT were slightly higher than Tyvaso Cmax values across dose comparisons. AE profile consistent with known prostacyclin effects and previous studies of Tyvaso. Between-subject variability for both AUC0-5 and Cmax was approximately two-fold less for TreT compared to Tyvaso. AUC0-5 and Cmax for TreT and Tyvaso increased in an approximately dose-proportional manner. Median Tmax: ~10 minutes for TreT and ~10 to 15 minutes with Tyvaso.

Example 5. Aerosolized and Powder Inhaled Treprostinil. Safety Evaluation

Figure 11:
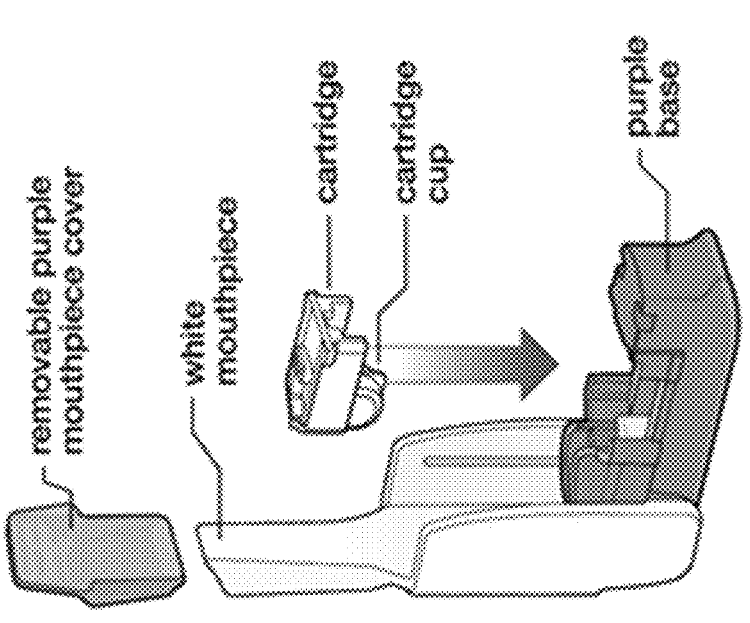
FIG. 11 shows a dry powder inhaler, which has a cartridge with a dose of Treprostinil Inhalation Powder (TreT).

Primary Objective:

To evaluate the safety and tolerability of Treprostinil Inhalation Powder (TreT) administered by a dry powder inhaler, such as the one shown in FIG. 11, in subjects with pulmonary arterial hypertension (PAH) currently treated with Tyvaso® (treprostinil inhalation solution administered via a nebulizer)

Secondary Objectives:

To evaluate systemic exposure and pharmacokinetics (PK) of treprostinil in subjects with PAH when delivered as Tyvaso® and TreT. To evaluate 6-Minute Walk Distance (6MWD) at study entry and after 3 weeks of treatment with TreT. To evaluate subject satisfaction with and preference for TreT with the Preference Questionnaire for Inhaled Treprostinil Devices (PQ-ITD). To evaluate patient reported PAH symptoms and impact with the PAH-Symptoms and Impact Questionnaire (PAH-SYMPACT).

Eligibility Criteria:

Diagnosis of WHO Group I PAH.

Subject must have started Tyvaso≥3 months prior to Baseline and on a stable regimen (no change in dose within 30 days of Baseline Visit) of Tyvaso (6 to 12 breaths QID).

Background therapy for PAH (eg, endothelin receptor antagonist or phosphodiesterase-5-inhibitor or both), on stable dose for a minimum of 30 days prior to Screening. Exclude other prostacyclin analogue or agonist (selexipag, epoprostenol, iloprost, or beraprost).

Excluding subjects with WHO Functional Class IV at Screening.

Subject is not able to perform inhalation maneuvers that meet inspiratory training criteria.

Exclude conditions which limits ambulation or ability to complete 6MWT (Baseline 6MWD>150 m).

Excluded initiation of pulmonary rehabilitation within 12 weeks prior to the Baseline Visit.

Figure 12:
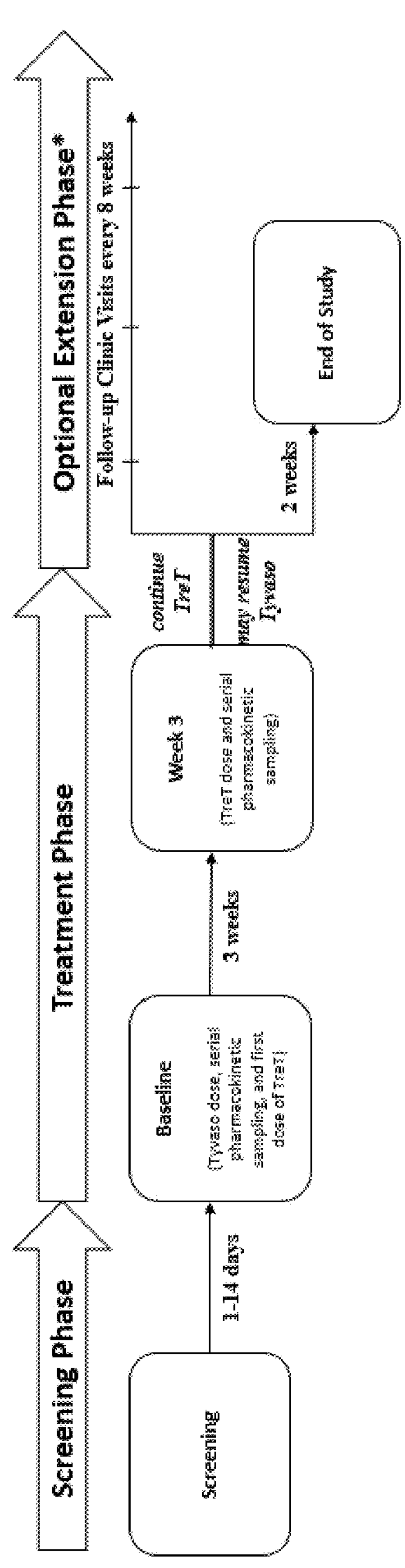
FIG. 12 shows a design of a study of Example 5. During the Optional Extension Phase (OEP), dosing titration is encouraged; the dose of TreT is titrated upward, as clinically tolerated, to identify a maximum stable dose in each subject.

FIG. 12 shows a design of the study. Table 16 presents information relating Tret and Tyvaso doses.

TABLE 16

| Tyvaso dose (QID) | TreT Dose (QID) | Device usage |
|---|---|---|
| 6 to 7 breaths | 32 μg | 32 μg cartridge |
| 8 to 10 breaths | 48 μg | 48 μg cartridge |
| 11 to 12 breaths | 64 μg | 32 μg + 32 μg cartridges |

TABLE 17

| Baseline demographics | |
|---|---|
| Age (years) | |
| Median | 57.0 (range: 23-82) |
| Sex, n (%) | |
| Female | 43 (84.3) |
| Male | 8 (15.7) |

TABLE 17-continued

| Baseline demographics | |
|---|---|
| **Current PAH Diagnosis, n (%)** | |
| Idiopathic/familial | 29 (56.9) |
| Associated with unrepaired/repaired congenital shunts | 4 (7.8) |
| Associated with collagen vascular disease | 14 (27.5) |
| Associated with HIV | 1 (2.0) |
| Associated with appetite suppressant/ other drug or toxin use | 3 (5.9) |
| **WHO Functional Class at Screening, n (%)** | |
| I | 6 (11.8) |
| II | 31 (60.8) |
| III | 14 (27.5) |

TABLE 12

Summary of Subject Accountability

| | TreT Dose in Treatment Phase | | | |
|---|---|---|---|---|
| | 32 mcg N = 2 n (%) | 48 mcg N = 27 n (%) | 64 mcg N = 22 n (%) | Overall N = 51 n (%) |
| Number of Subjects Enrolled | 2 | 27 | 22 | 51 |
| Received TreT | 2 (100.0) | 27 (100.0) | 22 (100.0) | 51 (100.0) |
| Enrolled in Optional Extension Phase | 2 (100.0) | 26 (96.3) | 21 (95.5) | 49 (96.1) |
| Subjects Who Discontinued Treatment Phase | 0 | 1 (3.7) | 1 (4.5) | 2 (3.9) |
| Adverse Event | 0 | 1 (3.7) | 1 (4.5) | 2 (3.9) |
| Subjects Who Discontinued OEP* | 0 | 3 (11.1) | 0 | 3 (5.9) |
| Adverse Event | 0 | 2 (7.4) | 0 | 2 (3.9) |
| Lost to Follow-up | 0 | 1 (3.7) | 0 | 1 (2.0) |

TABLE 13

Summary of background PAH medication

| | Overall N = 51; n (%) |
|---|---|
| ERA | 43 (84.3%) |
| Ambrisentan | 24 (47.1%) |
| Bosentan | 2 (3.9%) |
| Macitentan | 17 (33.3%) |
| PDE5-I | 41 (80.4%) |
| Sildenafil | 17 (33.3%) |

TABLE 13-continued

Summary of background PAH medication

| | Overall N = 51; n (%) |
|---|---|
| Tadalafil | 24 (47.1%) |
| sGC | 7 (13.7%) |
| Riociguat | 7 (13.7%) |

Figure 13:
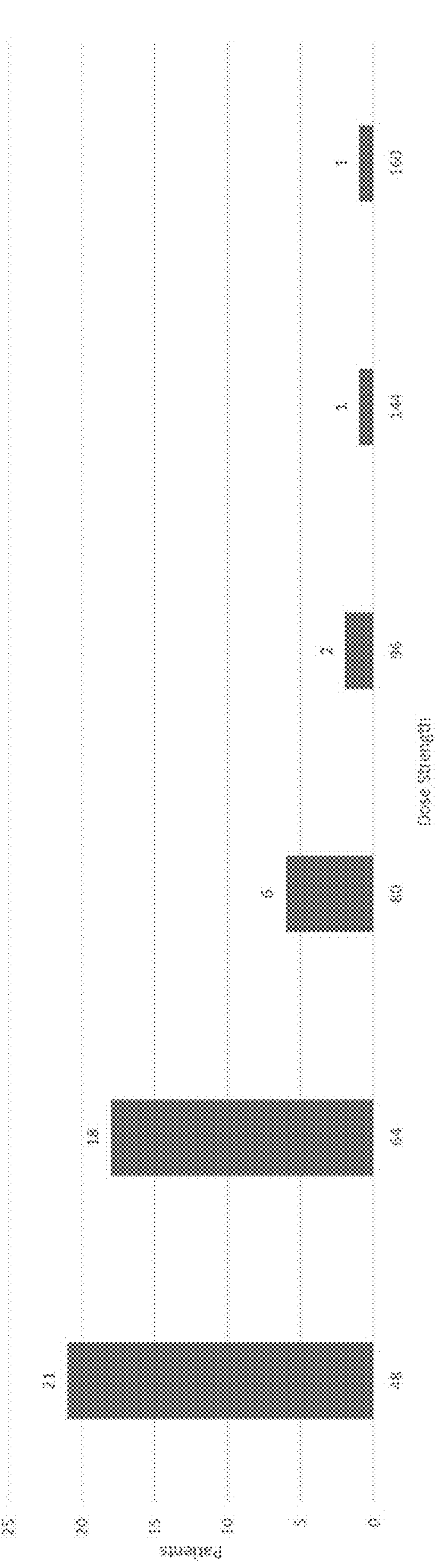
FIG. 13 shows a number of subjects for various maintenance TreT doses in the OEP.

Of the 51 subjects enrolled, assigned TreT doses for 3-week treatment period were 32 μg for 2 subjects; 48 μg for 27 subjects; 64 μg for 22 subjects. 49 subjects rolled into the Optional Extension Phase (OEP). FIG. 13 shows a number of subjects for various maintenance TreT doses in the OEP.

Figure 14:
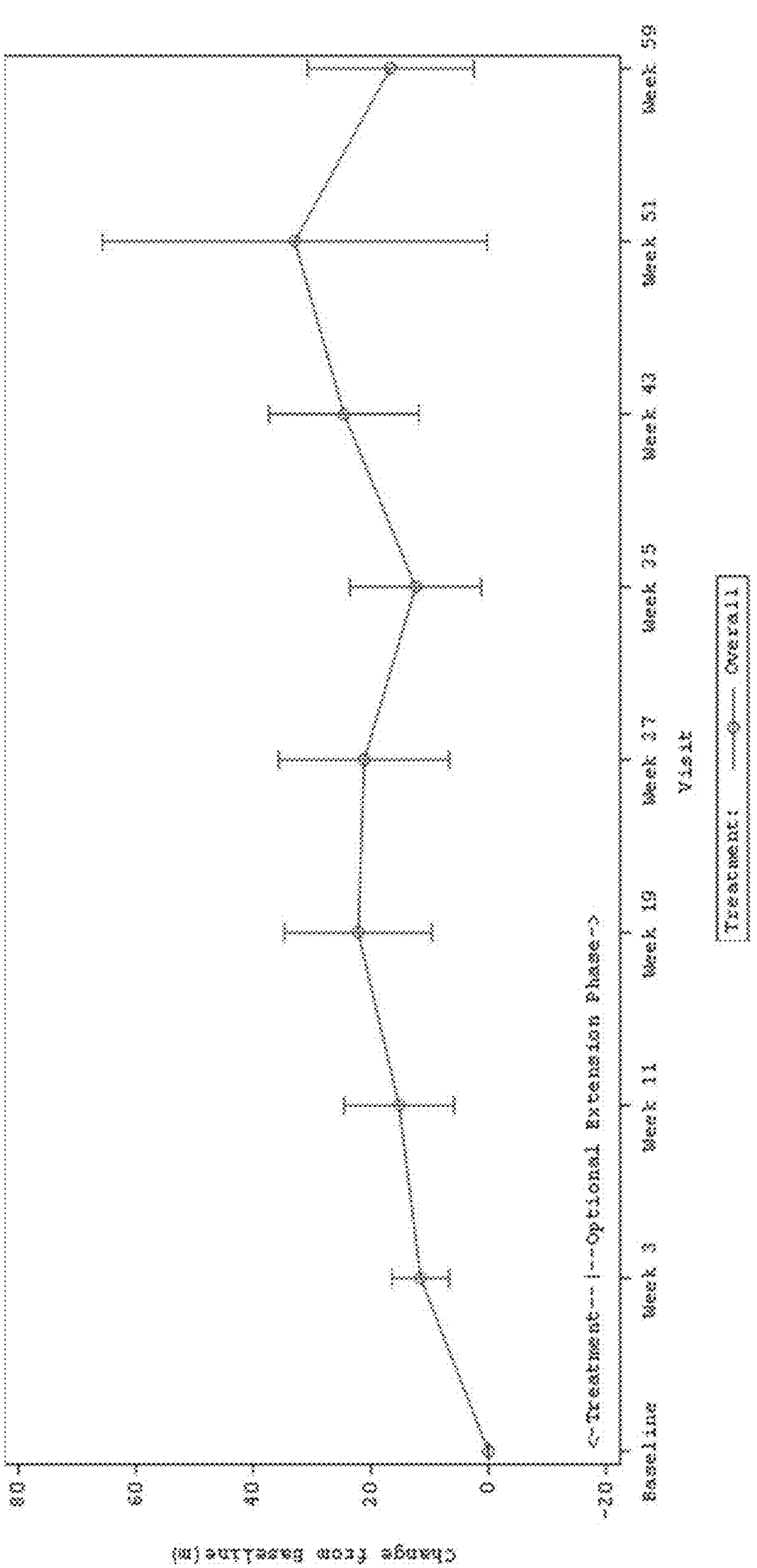
FIG. 14 shows a change in 6 minute walk distance (6MWD) with respect to a baseline 6MWD as a function of duration of TreT treatment.
Figure 15:
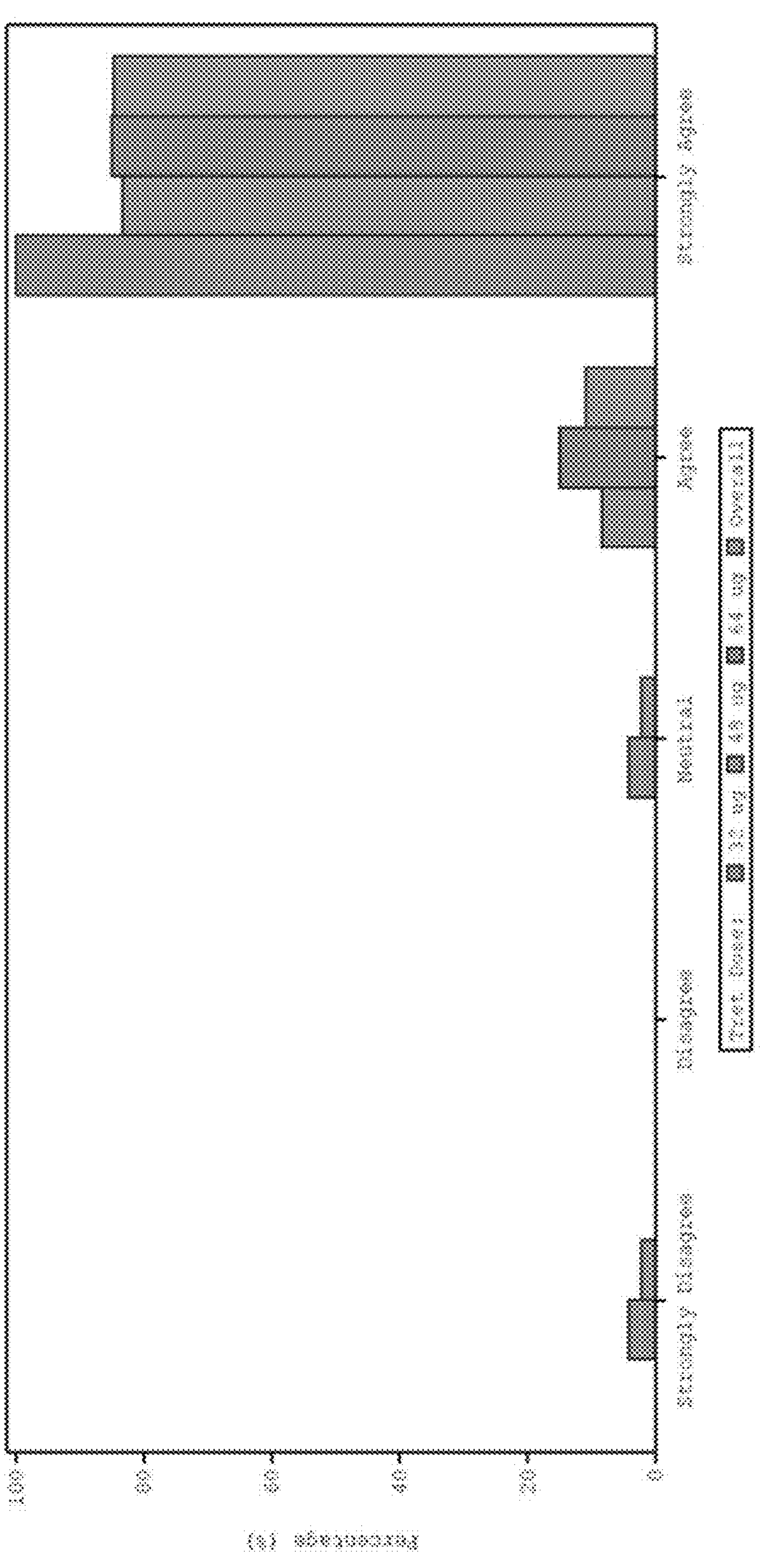
FIG. 15 is a plot reporting satisfaction of participants of the study of Example 5.

FIG. 14 shows a change in 6 minute walk distance (6MWD) with respect to a baseline 6MWD as a function of duration of TreT treatment. The change from Baseline in 6MWD for TreT overall demonstrated a significant improvement (11.5 m increase; $p=0.0217$) at Week 3. The improvements in 6MWD for TreT overall were sustained in the Optional Extension Phase.

Patient Reported Outcome Measures

The PQ-ITD is a patient-reported outcome questionnaire to evaluate subject satisfaction with and preference for inhaled treprostinil devices. The PQ-ITD was given at Baseline to evaluate the Tyvaso Inhalation System and at Week 3 to evaluate the TreT Inhaler.

The distribution of responses to each question on the PQ-ITD was significantly improved ($p\leq 0.0003$) between Baseline (Tyvaso nebulizer) and Week 3 (TreT inhaler). Overall satisfaction with the TreT inhaler was significantly improved at Week 3 (95.7%, $p<0.0001$) compared to satisfaction with the Tyvaso nebulizer at Baseline, FIG. 14.

PAH SYMPACT

The PAH-SYMPACT is a well validated patient-reported outcome questionnaire given to assess PAH symptoms and effects. The PAH-SYMPACT contains four domains (Cardiopulmonary Symptoms, Cardiovascular Symptoms, Physical Impacts, Cognitive/Emotional Impacts) and was given at Baseline, Week 3, and Week 11.

Analysis of patient-reported PAH SYMPACT data revealed a trend of improvement at both Week 3 and Week 11 for subjects receiving TreT.

Mean change from Baseline was lower for all domain scores of the PAH-SYMPACT at both weeks (range: −0.05 to −0.22), with significant improvements for physical impacts (range: −1.1 to 1.0; $p=0.0438$) and cognitive/emotional impacts (range: −1.3 to 0.5; $p=0.0048$) at Week 3.

TABLE 18

Overall Safety

| | TreT Dose in Treatment Phase | | | |
|---|---|---|---|---|
| Treatment Phase | 32 mcg N = 2 n (%) | 48 mcg N = 27 n (%) | 64 mcg N = 22 n (%) | Overall N = 51 n (%) |
| Total number of AEs | 0 | 37 | 22 | 59 |
| Total number of SAEs | 0 | 1 | 1 | 2 |
| AEs leading to withdrawal of study drug | 0 | 1 | 1 | 2 |
| Optional Extension Phase | 0 | | | |
| Total number of AEs | 2 | 51 | 29 | 82 |
| Total number of SAEs | 0 | 10 | 4 | 14 |
| AEs leading to withdrawal of study drug | 0 | 3 | 0 | 3 |

TABLE 19

Most frequent adverse events during the treatment phase

| Preferred Term | Treatment Phase Dose 32 mcg N = 2 n (%) | 48 mcg N = 27 n (%) | 64 mcg N = 22 n (%) | Overall N = 51 n (%) | TRIUMPH Tyvaso n (%) | Placebo n (%) |
|---|---|---|---|---|---|---|
| Cough | 0 | 9 (33.3) | 4 (18.2) | 13 (25.5) | 62 (54) | 35 (29) |
| Headache | 0 | 4 (14.8) | 4 (18.2) | 8 (15.7) | 47 (41) | 27 (23) |
| Dyspnoea | 0 | 2 (7.4) | 1 (4.5) | 3 (5.9) | 6 (5) | 6 (5) |
| Flushing | 0 | 1 (3.7) | 1 (4.5) | 2 (3.9) | 17 (15) | 1 (<1) |
| Nausea | 0 | 2 (7.4) | 0 | 2 (3.9) | 22 (19) | 13 (11) |
| Throat irritation | 0 | 1 (3.7) | 1 (4.5) | 2 (3.9) | 29 (25)* | 17 (14)* |

*TRIUMPH groups together Throat Irritation and Pharyngolaryngeal Pain.

TABLE 20

Most frequent adverse events during the treatment phase during the optional extension phase

| Preferred Term | TreT Dose in Treatment Phase 32 mcg N = 2 n (%) | 48 mcg N = 26 n (%) | 64 mcg N = 21 n (%) | Overall N = 49 n (%) |
|---|---|---|---|---|
| Cough | 0 | 3 (11.5) | 2 (9.5) | 5 (10.2) |
| Dyspnoea | 1 (50.0) | 2 (7.7) | 2 (9.5) | 5 (10.2) |
| Headache | 0 | 2 (7.7) | 2 (9.5) | 4 (8.2) |
| Diarrhoea | 0 | 1 (3.8) | 2 (9.5) | 3 (6.1) |
| Pneumonia | 0 | 2 (7.7) | 1 (4.8) | 3 (6.1) |
| Arthralgia | 0 | 2 (7.7) | 1 (4.8) | 3 (6.1) |
| Dizziness | 0 | 2 (7.7) | 1 (4.8) | 3 (6.1) |

Conclusions

Transition from Tyvaso to TreT was safe and well tolerated in this study. Most adverse effects (AEs) were mild to moderate in severity and occurred at severities and frequencies consistent with those seen in other inhaled treprostinil studies in patients with PAH.

Following 3 weeks of TreT administration, subjects switching from Tyvaso to TreT demonstrated:

Significant improvements in 6MWD (8.0 m increase; p=0.0217) at Week 3. As of 23 Dec. 2020 (data cut-off date), improvements in 6MWD for TreT overall were sustained in the OEP Significant satisfaction with and preference for the use of the TreT inhaler (PQ-ITD) Significant improvement in PAH impact scores, and a trend of improvement in PAH symptom scores (PAH SYMPACT).

Additional Embodiments

1. A method of treating interstitial lung disease (ILD) or pulmonary fibrosis in a subject in need, comprising administering to the subject a therapeutically effective amount of treprostinil, a prodrug, salt, or ester thereof.

2. A method of reducing pulmonary function decline in a subject with interstitial lung disease (ILD) or pulmonary fibrosis, comprising administering to the subject treprostinil, a prodrug, salt, or ester thereof.

3. A method of increasing forced vital capacity (FVC) in a subject suffering from ILD or pulmonary fibrosis, comprising administering to the subject treprostinil, a prodrug, salt, or ester thereof.

4. The method of any one of embodiments 1-3, wherein the ILD comprises one or more of idiopathic pulmonary fibrosis (IPF), desquamative interstitial pneumonia (DIP), acute interstitial pneumonia (AIP), nonspecific interstitial pneumonia (NSIP), respiratory bronchiolitis-associated interstitial lung disease (RB-ILD), cryptogenic organizing pneumonia (COP), lymphoid interstitial pneumonia (LIP), sarcoidosis, rheumatoid arthritis, systemic lupus erythematosus, systemic sclerosis, polymyositis, dermatomyositis, antisynthetase syndrome, silicosis, asbestosis, occupational lung disease, chronic hypersensitivity pneumonitis, idiopathic interstitial pneumonia (IIP), an autoimmune ILD, lymphangioleiomyomatosis (LAM), Langerhan's cell histiocytosis (LCH), drug associated ILD, vasculitis, granulomatosis, and berylliosis.

5. The method of embodiment 4, wherein the ILD comprises IPF.

6. The method of any one of embodiments 1-5, wherein the ILD comprises systemic sclerosis-associated interstitial lung disease (SSc-ILD).

7. The method of any one of embodiments 1-6, wherein the ILD was induced from antibiotics, chemotherapy, antiarrhythmic agents, coronavirus disease 2019, atypical pneumonia, *pneumocystis* pneumonia, tuberculosis (TB), *Chlamydia trachomatis*, respiratory syncytial virus, or lymphangitic carcinomatosis.

8. The method of any one of embodiments 1-7, wherein the subject has one or more of surfactant-protein-B deficiency, surfactant-protein-C deficiency, ABCA3-deficiency, brain lung thyroid syndrome, congenital pulmonary alveolar proteinosis, alveolar capillary dysplasia, mutations in telomerase reverse transcriptase, mutations in telomerase RNA component, mutations in the regulator of telomere elongation helicase 1, and mutations in poly(A)-specific ribonuclease.

9. The method of any one of embodiments 1-8, wherein the subject has one or more symptoms of shortness of breath, fatigue, weight loss, dry cough, chest pain, and lung hemorrhage.

10. The method of embodiment 9, wherein after administration the symptom is improved by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, as measured by a medically-recognized technique.

11. The method of embodiment 10, wherein the medically-recognized technique comprises one or more of Modified Medical Research Council (MMRC) Dyspnoea Scale, Modified Borg Dyspnoea Scale (0-10), Chalder Fatigue Scale, weight measurement scale, visual analogue scale (VAS) for cough, King's Brief Interstitial Lung Disease Questionnaire, Leicester Cough Questionnaire (LCQ), computed tomography (CT) scan, X-ray, multiple magnetic resonance imaging (MRI), pulmonary function testing (PFT), spirometry, lung volumes, maximal respiratory pressure, diffusing capacity, oxygen desaturation, and arterial blood gas evaluation.

12. The method of any one of embodiments 1-11, wherein treprostinil, a prodrug, salt, or ester thereof is administered in a pharmaceutical composition comprising treprostinil, a prodrug, salt, or ester thereof and a pharmaceutically acceptable carrier or excipient.

13. The method of claim any one of embodiments 1-12, wherein the administration comprises at least one of oral, inhalation, subcutaneous, nasal, intravenous, intramuscular, sublingual, buccal, rectal, vaginal, and transdermal administration.

14. The method of any one of embodiments 1-13, wherein the administration comprises inhalation.

15. The method of any one of embodiments 1-14, wherein a single inhalation administration event comprises from 1 to 20 breaths.

16. The method of any one of embodiments 1-15, comprising administration of at least one additional active agent to treat the ILD.

17. The method of embodiment 16, wherein the at least one additional active agent comprises a corticosteroid, mycophenolic acid, mycophenolate mofetil, azathioprine, cyclophosphamide, rituximab, pirfenidone, or nintedanib.

18. The method of embodiment 16 or 17, wherein the at least one additional active agent and treprostinil, a prodrug, salt, or ester thereof, are administered via a method selected from the group consisting of (a) concomitantly;

(b) as an admixture;

(c) separately and simultaneously or concurrently; and (d) separately and sequentially.

19. The method of any one of embodiments 1-18, wherein administration is once, twice, thrice, four times, five times, or six times per day.

20. The method of any one of embodiments 1-19, wherein administration is for a period selected from the group consisting of about 1 day, about 1 day to about 3 days, about 3 days to about 6 days, about 6 days to about 9 days, about 9 days to about 12 days, about 12 days to about 15 days, about 15 days to about 18 days, about 18 days to about 21 days, about 21 days to about 24 days, about 24 days to about 27 days, about 27 days to about 30 days, or about greater than 30 days.

21. The method of any one of embodiments 1-20, wherein the subject is a human.

22. The method of any one of embodiments 1-21, wherein the method results in an increased FVC compared to the FVC at the start of or prior to the start of administration.

23. The method of embodiment 22, wherein the administration results in an increased FVC at sixteen weeks after the start of administration compared to the FVC at the start of or prior to the start of administration.

24. The method of any one of embodiments 22-23, wherein the increase in FVC is at least 20%.

25. The method of embodiment 24, wherein the increase is FVC is at least 75%.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

What is claimed is:

1. A method of improving exercise capacity in a patient having pulmonary hypertension associated with interstitial lung disease, comprising administering by inhalation to the patient having pulmonary hypertension associated with interstitial lung disease an effective amount of at least 15 micrograms up to a maximum tolerated dose of treprostinil or a pharmaceutically acceptable salt thereof in a single administration event that comprises at least 6 micrograms per breath, wherein 4 single administration events are performed per day with a nebulizer comprising an inhalation solution comprising treprostinil or a pharmaceutically acceptable salt thereof.

2. The method of claim 1, wherein said administering provides a statistically significant increase of a 6 minutes walk distance in the patient after 8 weeks of the administering.

3. The method of claim 1, wherein said administering provides a statistically significant increase of a 6 minutes walk distance in the patient after 12 weeks of the administering.

4. The method of claim 1, wherein said administering provides a statistically significant increase of a 6 minutes walk distance in the patient after 16 weeks of the administering.

5. The method of claim 1, wherein said administering increases a 6 minutes walk distance of the patient by at least 10 m after 8 weeks of the administering.

6. The method of claim 1, wherein said administering increases a 6 minutes walk distance of the patient by at least 10 m after 12 weeks of the administering.

7. The method of claim 1, wherein said administering increases a 6 minutes walk distance of the patient by at least 10 m after 16 weeks of the administering.

8. The method of claim 1, wherein said administering reduces a plasma concentration of NT-proBNP in the patient by at least 200 pg/ml after 8 weeks of the administering.

9. The method of claim 1, wherein said administering reduces a plasma concentration of NT-proBNP in the patient by at least 200 pg/ml after 12 weeks of the administering.

10. The method of claim 1, wherein said administering reduces a plasma concentration of NT-proBNP in the patient by at least 200 pg/ml after 16 weeks of the administering.

11. The method of claim 1, wherein said administering provides a statistically significant reduction of at least one exacerbation of the interstitial lung disease.

12. The method of claim 1, wherein said administering provides a statistically significant reduction of clinical worsening events due to the interstitial lung disease.

13. The method of claim 12, wherein the clinical worsening events comprise at least one of hospitalization for cardiopulmonary indication and a decrease in a 6-minute walk distance by more than 15% compared to a baseline 6-minute walk distance prior to the administering.

14. The method of claim 1, wherein said administering provides a statistically significant improvement of forced vital capacity (FVC) in the patient after 8 weeks of the administering.

15. The method of claim 1, wherein said administering provides a statistically significant improvement of forced vital capacity (FVC) in the patient after 12 weeks of the administering.

16. The method of claim 1, wherein said administering provides a statistically significant improvement of forced vital capacity (FVC) in the patient after 16 weeks of the administering.

17. The method of claim 14, wherein said improvement is an improvement in the forced vital capacity (FVC) in the patient by at least 20 ml.

18. The method of claim 15, wherein said improvement is an improvement in the forced vital capacity (FVC) in the patient by at least 20 ml.

19. The method of claim 16, wherein said improvement is an improvement in the forced vital capacity (FVC) in the patient by at least 20 ml.

20. The method of claim 1, wherein the effective amount of treprostinil or a pharmaceutically acceptable salt administered to the patient in a single inhalation administration event is from 15 μg to 100 μg.

21. The method of claim 20, wherein the single inhalation administration event does not exceed 15 breaths by the patient.

22. The method of claim 1, wherein said administering increases a 6 minutes walk distance of the patient by at least 15 m after 8 weeks of the administering.

23. The method of claim 1, wherein said administering increases a 6 minutes walk distance of the patient by at least 15 m after 12 weeks of the administering.

24. The method of claim 1, wherein said administering increases a 6 minutes walk distance of the patient by at least 15 m after 16 weeks of the administering.

* * * * *